(12) United States Patent
Jin et al.

(10) Patent No.: US 10,227,315 B2
(45) Date of Patent: *Mar. 12, 2019

(54) MITOCHONDRIAL UNCOUPLERS FOR TREATMENT OF METABOLIC DISEASES AND CANCER

(71) Applicant: RUTGERS, THE STATE UNIVERSITY OF NEW JERSEY, New Brunswick, NJ (US)

(72) Inventors: Shengkan Jin, Belle Mead, NJ (US); David J. Augeri, Princeton, NJ (US); Bin Cao, Highland Park, NJ (US); Hanlin Tao, Branchburg, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/599,177

(22) Filed: May 18, 2017

(65) Prior Publication Data
US 2017/0334869 A1 Nov. 23, 2017

Related U.S. Application Data

(60) Provisional application No. 62/338,190, filed on May 18, 2016.

(51) Int. Cl.
| | | |
|---|---|---|
| *C07D 277/82* | (2006.01) | |
| *C07D 417/04* | (2006.01) | |
| *C07D 417/12* | (2006.01) | |
| *A61K 31/167* | (2006.01) | |
| *A61K 31/277* | (2006.01) | |
| *A61K 31/428* | (2006.01) | |
| *A61K 31/4545* | (2006.01) | |
| *A61K 31/496* | (2006.01) | |
| *A61K 31/536* | (2006.01) | |
| *A61K 31/5375* | (2006.01) | |
| *A61K 31/5377* | (2006.01) | |
| *A61K 31/675* | (2006.01) | |
| *A61K 45/06* | (2006.01) | |
| *C07C 235/64* | (2006.01) | |
| *C07C 255/60* | (2006.01) | |
| *C07D 241/20* | (2006.01) | |
| *C07D 295/205* | (2006.01) | |
| *C07F 9/6541* | (2006.01) | |

(52) U.S. Cl.
CPC .......... *C07D 277/82* (2013.01); *A61K 31/167* (2013.01); *A61K 31/277* (2013.01); *A61K 31/428* (2013.01); *A61K 31/4545* (2013.01); *A61K 31/496* (2013.01); *A61K 31/536* (2013.01); *A61K 31/5375* (2013.01); *A61K 31/5377* (2013.01); *A61K 31/675* (2013.01); *A61K 45/06* (2013.01); *C07C 235/64* (2013.01); *C07C 255/60* (2013.01); *C07D 241/20* (2013.01); *C07D 295/205* (2013.01); *C07D 417/04* (2013.01); *C07D 417/12* (2013.01); *C07F 9/6541* (2013.01)

(58) Field of Classification Search
CPC ... C07D 277/82; C07D 417/04; C07D 417/12
USPC ......................................................... 548/163
See application file for complete search history.

(56) References Cited

U.S. PATENT DOCUMENTS

| | | |
|---|---|---|
| 3,113,067 A | 12/1963 | Reimer et al. |
| 3,147,300 A | 9/1964 | Ernst et al. |
| 3,909,816 A | 9/1975 | Teeters |
| 4,405,616 A | 9/1983 | Rajadhyaksha |
| 4,659,738 A | 4/1987 | Miller et al. |
| 4,801,586 A | 1/1989 | Minaskanian et al. |
| 4,861,764 A | 8/1989 | Samour et al. |
| 4,886,783 A | 12/1989 | Minaskanian et al. |
| 4,983,396 A | 1/1991 | Bodor et al. |
| 5,118,845 A | 6/1992 | Peck et al. |
| 5,196,410 A | 3/1993 | Francoeur et al. |
| 8,486,374 B2 | 7/2013 | Tamarkin et al. |
| 8,741,265 B2 | 6/2014 | Tamarkin et al. |
| 2004/0138301 A1 | 7/2004 | Hansen et al. |
| 2005/0282862 A1 | 12/2005 | Beight et al. |
| 2006/0089395 A1 | 4/2006 | Muto et al. |
| 2006/0292146 A1 | 12/2006 | Dixon et al. |
| 2007/0299111 A1 | 12/2007 | Powers et al. |
| 2008/0039629 A1 | 2/2008 | Ramesh et al. |
| 2009/0062396 A1 | 3/2009 | Olesen et al. |
| 2009/0239919 A1 | 9/2009 | Wood et al. |
| 2010/0113770 A1 | 5/2010 | Muto et al. |
| 2010/0190832 A1 | 7/2010 | Surolia |
| 2013/0150399 A1 | 6/2013 | Koong et al. |
| 2013/0324555 A1 | 12/2013 | Wood et al. |
| 2014/0221411 A1 | 8/2014 | Kim et al. |
| 2016/0046560 A1 | 2/2016 | Sexton et al. |
| 2017/0319516 A1* | 11/2017 | Jin ...................... A61K 31/166 |

FOREIGN PATENT DOCUMENTS

| | | |
|---|---|---|
| EP | 1510207 A1 | 3/2005 |
| WO | 2000006143 A1 | 2/2000 |
| WO | 2004006906 A2 | 1/2004 |
| WO | 2009032749 B1 | 3/2009 |
| WO | 2009047584 A1 | 4/2009 |

(Continued)

OTHER PUBLICATIONS

Chemical Abstracts Registry No. 78417-51-3, indexed in the Registry file on STN CAS Online on Nov. 16, 1984.*

(Continued)

*Primary Examiner* — Laura L Stockton
(74) *Attorney, Agent, or Firm* — Pepper Hamilton LLP

(57) ABSTRACT

The present disclosure relates to benzamide compounds, prodrugs of the compounds, pharmaceutical compositions containing the compounds and/or the prodrugs and methods of using the compounds, prodrugs and pharmaceutical compositions in the treatment of diseases related to lipid metabolism including diabetes, Non-Alcholic Fatty Liver Disease (NAFLD), Non-Alcholic Steathohepatitis (NASH), diseases caused by abnormal cell proliferation including cancer, psoriasis, and infectious diseases.

15 Claims, 7 Drawing Sheets

(56) References Cited

FOREIGN PATENT DOCUMENTS

| | | | |
|---|---|---|---|
| WO | 2012025638 A1 | 3/2012 | |
| WO | 2012040223 B2 | 3/2012 | |
| WO | 2012068274 A1 | 5/2012 | |
| WO | 2013164769 A1 | 11/2013 | |
| WO | 2013169939 A2 | 11/2013 | |
| WO | 2015154169 A1 | 10/2015 | |
| WO | WO-2016/004513 A1 | * | 1/2016 |
| WO | WO-2016/081599 A1 | * | 5/2016 |

OTHER PUBLICATIONS

Chemical Abstracts Registry No. 1040019-73-5, indexed in the Registry file on STN CAS Online on Aug. 10, 2008.*
Chemical Abstracts Registry No. 1042515-02-5, indexed in the Registry file on STN CAS Online on Aug. 21, 2008.*
Chemical Abstracts Registry No. 78417-52-4, indexed in the Registry file on STN CAS Online on Nov. 16, 1984.*
Chemical Abstracts Registry No. 1036494-79-7, indexed in the Registry file on STN CAS Online on Jul. 27, 2008.*
Chemical Abstracts Registry No. 1350060-36-4, indexed in the Registry file on STN CAS Online on Dec. 7, 2011.*
Matyk et al., Farmaco (2005), 60(5), pp. 399-408.*
Chemical Abstracts Registry No. 1928758-63-7, indexed in the Registry file on STN CAS Online on Jun. 9, 2016 (Year: 2016).*
Chemical Abstracts Registry No. 1928758-62-6 {indexed in the Registry file on STN CAS Online on Jun. 9, 2016 (Year: 2016).*
Chemical Abstracts Registry No. 1928758-60-4 {indexed in the Registry file on STN CAS Online on Jun. 9, 2016 (Year: 2016).*
Chemical Abstracts Registry No. 1928758-58-0 {indexed in the Registry file on STN CAS Online on Jun. 9, 2016 (Year: 2016).*
Wallace et al. Mitochondrial Targets of Drug Toxicity, Annu. Rev. Pharmacol. Toxicol., 2000, vol. 40, pp. 353-388.
Stumvall et al. Type 2 diabetes: principles of pathogenesis and therapy, Lancet, 2005, vol. 365, pp. 1333-1346.
Andrews et al., The Biology and Toxicology of Molluscicides, Bayluscide, Pharmac. Ther., 19:245-295 (1983).
Kenwood et al., Structure-activity relationships of furazano[3,4-b]pyrazines as mitochondrial uncouplers, Bioorganic & Medicinal Chemistry Letters 25 (2015), 4858-4861.
International Search Report and Written Opinion of the International Searching Authority, for PCT/US2011/061028, dated Apr. 2, 2012.
Extended European Search Report for PCT/US2011/061028, dated Mar. 21, 2014.
Curnock, Adam P., et al., "Inhibition of stimulated Jurkat cell adenosine 3', 5'-cyclic monophosphate synthesis by the immunomodulatory compound HR325", Biochemical Pharmacology, vol. 61, No. 2, Jan. 1, 2001, pp. 227-235; XP055107261, ISSN: 0006-2952, DOI: 10.016/50006-2952(00)00552-9.
Samuel V.T., et al., Lancet, 2010, 375:2267-77.
Terada, H., Environ. Health Perspect. 1990, 87:213-218.
Design of Prodrugs, Notari, Robert E., edited by H. Bundgaard (Elsevier, 1985), and Methods in Enzymology, vol. 112, at pp. 309-396, edited by K. Widder et al. (Academic Press, 1985).

A textbook of Drug Design and Development, edited by Krosgaard-Larsen and H. Bundgaard, Chapter 5, Design and Application of Prodrugs, by H. Bundgaard, at pp. 113-191 (1991).
Tao H., et al. Niclosamide ethanolamine improves blood glycemic control and reduces hepatic steatosis in mice, Nat. Med. (2014), Nov:20(11): 1263-1269.
International Search Report and Written Opinion of the International Searching Authority, for PCT/US2015/061342, dated Jan. 28, 2016.
Reddy, PVG et al. Synthesis of novel benzothiazole compounds with an extended conjugated system. ARKIVOC, vol. xvi, 2007, pp. 113-112.
Perry RJ, Zhang D, Zhang XM, Boyer JL, Shulman GL, Science Mar. 13, 2015;347(6227):1253-6.
Vander Heiden MG, Cantley LC, Thompson CB. Science. May 22, 2009;324(5930):1029-33.
J. March, Advanced Organic Chemistry: Reactions, Mechanisms and Structure, 4th Ed. (New York: Wiley-Interscience, 1992.
Medicinal Chemistry: Principles and Practice, F.D. King, ed., The Royal Society of Chemistry, Cambridge, UK, 1994, Table of Contents Only.
Hydrolysis in Drug and Prodrug Metabolism. Chemistry, Biochemistry and Enzymology, B. Testa, J. M. Mayer, VCHA and Wiley—VCH, Zurich, Switzerland, 2003, Table of Contents Only.
The Practice of Medicinal Chemistry, C. G. Wermuth, 2nd ed., Academic Press, San Diego, CA, 1999, Cover Page Only.
Remington's Pharmaceutical Sciences, 18 Edition, Mack Publishing Company, Easton, PA, 1990, Cover Page Only.
Farmaco, 2005, vol. 60, #5 p. 399-408, only p. 309 provided.
Bioorganic and Medicinal Chemistry Letters, 2013, 23(6), 1748-1751, Abstract Only.
The Merck Index, Thirteenth Edition, Budavari et al., Eds., Merck & Co., Inc., Rahway, N.J. (2001), Citation Only.
CTFA (Cosmetic, Toiletry, and Fragrance Association) International Cosmetic Ingredient Dictionary and Handbook, Tenth Edition (2004).
Inactive Ingredient Guide, U.S. Food and Drug Administration (FDA) Center for Drug Evaluation and Research (CDER) Office of Management, http://www.accessdata.fda.gov/scripts/cder/iig/index.cfm, accessed Aug. 17, 2017.
Goodman and Gillman's: The Pharmacological Bases of Therapeutics, 8th Ed., Gilman et al. Eds. Pergamon Press (1990).
Diadone et al., Salicylanilide and its heterocyclic analogs. A Comparative study of their antimicrobial activity, DIE PHARMAZIE: An Internatioanl Journal of Pharmaceutical Sciences (Jan. 1, 1990), 45 (6):441-442.
Kang et al., Discovery of Novel 2-hydroxydiarylamide derivatives as TMPRSS4 inhibitors, Bioorganic & Medical Chemistry Letters (2013), 23(6):1748-1751.
Vinsova et al., Salicylanilide diethyl phophates: Synthesis, antimicrobial activity and cytotoxicity, Bioorganic & Medicinal Chemistry (Dec. 12, 2013), 22(2):728-737.
Extended European Search Report for PCT/US2015/061342, dated May 24, 2018.
Coburn et al., Potential Salicylamide Antiplaque Agents: In Vitro Antibacterial Activity against Actinomyces viscosus, J. Med. Chem. (1981), 24(10):1245-1249.

* cited by examiner

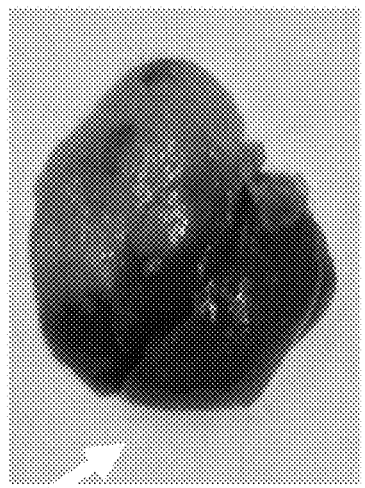
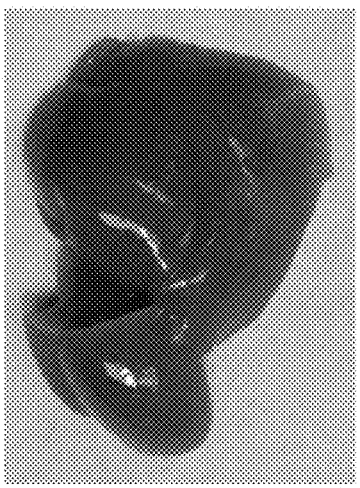
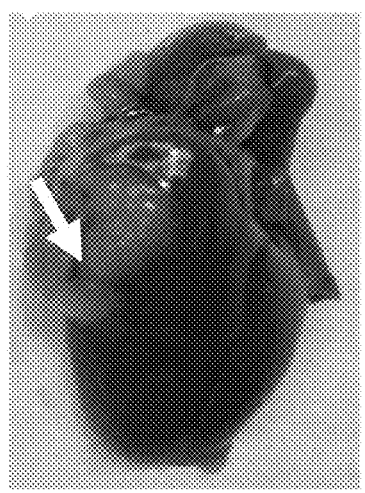
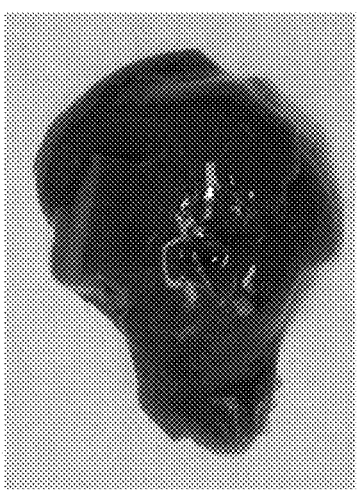
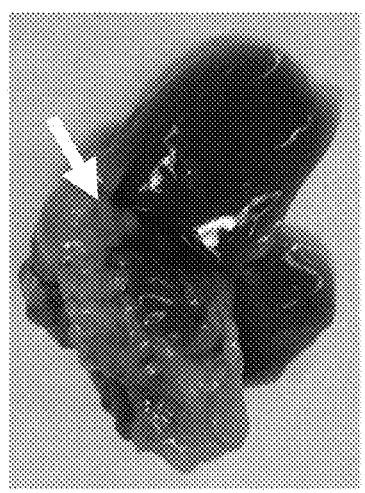
Fig. 5A
Fig. 5B

| | Gram positive bacteria | | Commonly used code | Gram Staining | Characteristic | Comp. 28 | Comp. 21 | Comp. 41 | Comp. 24 | Comp. 50 | Vancomycin |
|---|---|---|---|---|---|---|---|---|---|---|---|
| | Enterococcus faecalis | | ATCC 29212 | G+ | aerobic;QC | * | ** | 16(32) | * | *** | 2 (4) |
| | Enterococcus faecalis | | ATCC 51575 | G+ | aerobic | >64 | 32 | 32 | * | * | >64 |
| ESKAPE | Enterococcus faecium | | ATCC 700221 | G+ | aerobic | ** | * | * | ** | *** | 64 |
| ESKAPE | Enterococcus faecium | | ATCC 51559 | G+ | aerobic | * | * | * | ** | *** | >64 |
| ESKAPE | Staphylococcus aureus | | ATCC 29213 | G+ | aerobic;QC | * | ** | 64(1) | ** | *** | 1 |
| ESKAPE | Staphylococcus aureus | | NRS 384 | G+ | aerobic | * | *** | *** | *** | *** | 1 |
| ESKAPE | Staphylococcus aureus | | NRS 71 | G+ | aerobic | ** | *** | ** | ** | *** | 0.5 |
| ESKAPE | Staphylococcus aureus | | NRS 100 | G+ | aerobic | *** | *** | ** | *** | *** | 2 |
| ESKAPE | Staphylococcus aureus | | VR S1 | G+ | aerobic | *** | *** | ** | ** | *** | >64 |
| ESKAPE | Staphylococcus aureus | | VR S3a | G+ | aerobic | * | ** | ** | ** | *** | 16 |
| ESKAPE | Staphylococcus epidermidis | | ATCC 35984 | G+ | aerobic | *** | *** | ** | *** | *** | 2 |
| | Fastidious bacteria | | Commonly used code | Gram staining | Characteristic | Comp. 28 | Comp. 21 | Comp. 41 | Comp. 24 | Comp. 50 | Van |
| | Moraxella catarrhalis | | ATCC 43617 | G- | aerobic | *** | *** | *** | *** | *** | 16 |
| | Neisseria gonorrhoeae | | ATCC 700825 | G- | 5% CO2 | *** | *** | *** | *** | *** | 16 |

Fig. 7

MITOCHONDRIAL UNCOUPLERS FOR TREATMENT OF METABOLIC DISEASES AND CANCER

CROSS-REFERENCE TO RELATED APPLICATIONS

The present application claims benefit of and priority to U.S. Provisional No. 62/338,190 entitled "NOVEL MITOCHONDRIAL UNCOUPLERS FOR TREATMENT OF METABOLIC DISEASES AND CANCER," filed May 18, 2016, the contents of which is hereby incorporated by reference in its entirety.

FIELD OF INVENTION

The present disclosure relates to benzamide compounds, prodrugs of the compounds, pharmaceutical compositions containing the compounds and/or the prodrugs and methods of using the compounds, prodrugs and pharmaceutical compositions in the treatment of diseases related to lipid metabolism including diabetes, Non-Alcoholic Fatty Liver Disease (NAFLD), Non-Alcoholic Steathohepatitis (NASH), diseases caused by abnormal cell proliferation including cancer and psoriasis, and infectious diseases.

SUMMARY

Various embodiments provide compounds, compositions, and methods for prevention and treatment of metabolic diseases, cancer, psoriasis and infectious diseases. Compounds described herein exhibit activities of mitochondrial uncoupling, activation of AMPK, and inhibition of cell proliferation.

Some embodiments of the present disclosure are directed to a compound of formula (I):

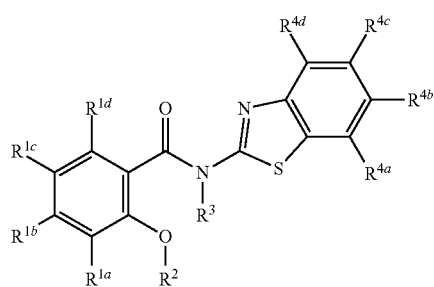

(I)

or a pharmaceutically acceptable salt, solvate, or prodrug thereof,
wherein,
$R^{1a}$ is selected from the group consisting of hydrogen; optionally substituted $C_1$-$C_6$ alkyl; optionally substituted $C_2$-$C_6$ alkenyl; optionally substituted $C_2$-$C_6$ alkynyl; optionally substituted $C_3$-$C_{10}$ cycloalkyl; (($C_1$-$C_6$ alkylsulfonyl)amino)$C_1$-$C_6$ alkyl; optionally substituted $C_3$-$C_{10}$ heterocyclyl; optionally substituted $C_3$-$C_{10}$ aryl; optionally substituted $C_3$-$C_{10}$ heteroaryl; $C_1$-$C_6$ perfluoroalkyl; halo; cyano; nitro; optionally substituted amino; —C(O)NHR$^5$; —C(O)NR$^5$R$^6$; —C(O)H; —C(O)R$^7$; —C(O)OH; and —C(O)OR$^5$;
each of $R^{1b}$, $R^{1c}$ and $R^{1d}$ is independently selected from the group consisting of: hydrogen; $C_1$-$C_6$ perfluoroalkyl; $C_1$-$C_6$ alkyl; $C_2$-$C_6$ alkenyl; $C_1$-$C_6$ alkynyl; $C_3$-$C_{10}$ cycloalkyl; cyano and halo;

$R^2$ is selected from the group consisting of hydrogen; mono-saccharide; di-saccharide; C(O)NR$^5$R$^6$; C(O)R$^7$; —P(O)(OH)$_2$; and —P(O)(ONa)$_2$; wherein the mono-saccharides and di-saccharide are attached to the phenolic oxygen at the anomeric center to form a glycosidic bond;
$R^3$ is hydrogen, or alternatively, $R^2$ and $R^3$ taken together are a carbonyl group and together with the atoms to which they are attached, form a six-membered heterocyclic carbamate; each of $R^{4a}$, $R^{4b}$, $R^{4c}$ and $R^{4d}$ is independently selected from the group consisting of hydrogen; $C_1$-$C_6$ perfluoroalkyl; cyano; nitro; —CHF$_2$, $C_1$-$C_6$ alkyl, —OC$_1$-$C_6$ alkyl, —OCF$_3$, $C_3$-$C_{10}$ cycloalkyl, —CF$_3$, —SO$_2$CH$_3$ and halo;
each of $R^5$ and $R^6$ is independently selected from the group consisting of optionally substituted $C_1$-$C_6$ alkyl; and $C_1$-$C_6$ alkylsulfonyl; alternatively $R^5$ and $R^6$ taken together with the nitrogen to which they are attached form an optionally substituted $C_3$-$C_6$ heterocyclyl; and
$R^7$ is selected from the group consisting of: optionally substituted (alkylamino) $C_1$-$C_6$ alkyl; and optionally substituted $C_3$-$C_6$ heterocyclyl.

Some embodiments are directed to a compound of formula (III)

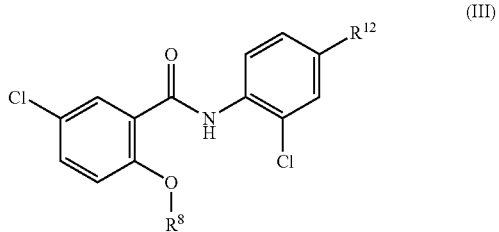

(III)

or a pharmaceutically acceptable salt, solvate, or prodrug thereof,
wherein,
$R^8$ is selected from the group consisting of: C(O)NR$^9$R$^{10}$ and C(O)R$^{11}$;
each of $R^9$ and $R^{10}$ is independently selected from the group consisting of optionally substituted $C_1$-$C_6$ alkyl; and $C_1$-$C_6$ alkylsulfonyl; alternatively $R^9$ and $R^{10}$ taken together with the nitrogen to which they are attached form an optionally substituted $C_3$-$C_6$ heterocyclyl;
$R^{11}$ is selected from the group consisting of: optionally substituted (alkylamino)$C_1$-$C_6$-alkyl; and optionally substituted $C_3$-$C_6$ heterocyclyl; and
$R^{12}$ is selected from the group consisting of: $C_{1-6}$ perfluoroalkyl; halo; cyano; and nitro.

Some embodiments are directed to a compound of formula (IV)

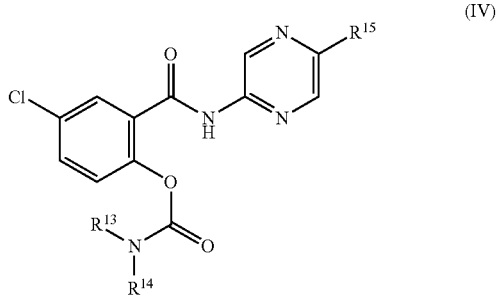

(IV)

or a pharmaceutically acceptable salt, solvate, or prodrug thereof, wherein, each of $R^{13}$ and $R^{14}$ is independently selected from the group consisting of optionally substituted $C_1$-$C_6$ alkyl; and $C_1$-$C_6$ alkylsulfonyl; alternatively $R^{13}$ and $R^{14}$ taken together with the nitrogen to which they are attached form an optionally substituted $C_3$-$C_6$ heterocyclyl; and $R^{15}$ is selected from the group consisting of $C_1$-$C_6$-perfluoroalkyl; nitro; halo and cyano.

Embodiments herein describe a pharmaceutical composition comprising: a compound according to any one of the preceding embodiments, or a pharmaceutically acceptable salt or prodrug thereof; and a pharmaceutically acceptable carrier or diluent.

Some embodiments describe a method of treating a metabolic disease or disorder characterized by hyperglycemia, or insulin resistance or by abnormal accumulation of lipid in tissue, a disease or a disorder in which hyperglycemia, or insulin resistance or abnormal accumulation of lipid in tissue is a symptom, in a subject, comprising administering to the subject a therapeutically effective amount of a compound or a pharmaceutical composition described herein.

Some embodiments describe a method of treating cancer or hyperplasia, in a subject, comprising administering to the subject a therapeutically effective amount of a compound or a pharmaceutical composition described herein.

Some embodiments describe a method for long-term disease management of a metabolic disease or disorder, or for long-term disease management of cancer, comprising administering to a subject in need of such long-term management an effective amount of a compound or a pharmaceutical composition described herein.

Some embodiments describe a method of treating or preventing a dermatological disorder in a subject, comprising administering to the subject a therapeutically effective amount of a compound or a pharmaceutical composition described herein.

Some embodiments describe a method of treating or preventing a bacterial infection in a subject, comprising administering to the subject a therapeutically effective amount of a compound or a pharmaceutical composition described herein.

Some embodiments describe the use of a compound described herein in the manufacture of a medicament for treatment of a metabolic disease or disorder. In some embodiments, the metabolic disease or disorder may be selected from diabetes, obesity, non-alcoholic fatty liver disease, alcoholic fatty liver disease, dyslipidemia, a disease where hyperglycemia, or insulin resistance or abnormal lipid accumulation in tissue is a symptom, or related disorders or complications. In some embodiments, the compounds described herein may be used in the manufacture of a medicament for the treatment of cancer, a disease where cell proliferation (hyperplasia) is a symptom, or cancer or hyperplasia related complications. In some embodiments, the compounds described herein may be used in the manufacture of a medicament for infectious diseases.

DESCRIPTION OF THE DRAWINGS

FIG. 4A is Panc 2, DMSO; FIG. 4B is Panc 2, compound 28. FIG. 4C is Panc 1, DMSO; and FIG. 4D is Panc 1, compound 28.

FIGS. 5A-5B show the effect of an example compound on hepatic metastasis of pancreatic cancer. 250,000 Panc 2 cells were injected at the site of spleen of NOD-scid-gamma mice. In FIG. 5A, the untreated mice had massive hepatic tumor metastasis. In FIG. 5B, the testing compound treated mice, showed little or no hepatic tumor metastasis.

FIG. 7 shows Table V the MIC (minimal inhibition concentration) of example compounds on a list of bacteria: MIC was either categorized by: *≤1.0 µg/ml; >1.0 µg/ml but <2.0 µg/ml; *≥2.0 µg/ml but ≤8.0 µg/ml, or with a MIC concentration (number in µg/ml). MIC for vancomycin is listed as a reference.

DETAILED DESCRIPTION

Figure 1:
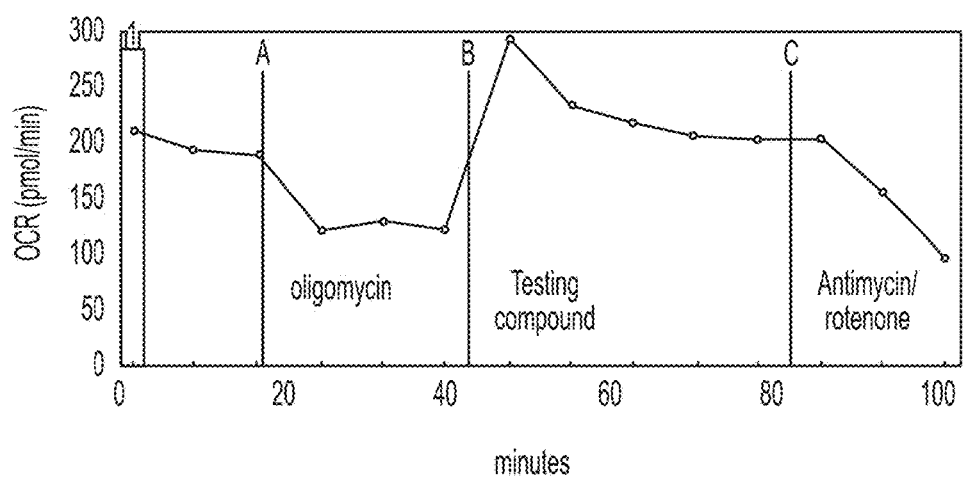
FIG. 1 shows a typical OCR (oxygen consumption rate) profile of a mitochondrial uncoupler in Seahorse cell-based assay. Line A indicating addition of oligomycin; Line B indicating addition of a testing compound. Line C indicating addition of electron transport chain inhibitor(s) antimycin/rotenone.

Mitochondria are central to cellular metabolism, which provides both energy to sustain biological activities and metabolic intermediates for biosynthesis of eukaryotic cells. Mitochondrial function is essential for cells to oxidize glucose and lipid and for cells to proliferate. Modification of mitochondrial function can effectively change lipid and glucose oxidation rates as well as affect cell proliferation in normal cells, abnormal cells such as cancer cells, and in cells of parasitic organisms of human and animals. Thus, compounds that modify mitochondrial activity can be used for treating diseases related to glucose or lipid metabolism, diseases related to cell proliferation, and diseases of infectious organisms.

Mitochondrial metabolism of glucose and lipid is described as follows. Glucose and lipids such as triglyceride are the most important fuels of cells. Glucose first metabolizes to pyruvate through glycolysis. In turn, pyruvate enters mitochondria, where it converts to acetyl-CoA. Similarly, triglyceride is first hydrolyzed to glycerol and fatty acid, which enter mitochondria, where they are oxidized to acetyl-CoA. In mitochondrial matrix, acetyl-CoA from glucose metabolism as well as lipid metabolism is then oxidized through TCA cycle. The energy released from the oxidation reactions is stored in the form of high energy electrons in the molecules of NADH and $FADH_2$. Electrons from NADH and $FADH_2$ are in turn fed into the mitochondrial electron transporter chain, which are localized on the inner membrane of mitochondria. As the electrons travel through the electron transporter chain and reach the electron donor, oxygen molecule, energy is released and used for pumping protons from mitochondrial matrix across the mitochondrial inner membrane, establishing a proton gradient across the membrane. Finally, protons travel across the mitochondrial inner membrane through the $F_oF_1$-ATP synthase and drive the synthesis of ATP, the energy molecule that can be directly used by the various cellular machineries. Under normal conditions, mitochondrial oxidation provides more than 90% of cellular ATP. In addition, mitochondrial oxidation provides and regulates the availability of metabolic intermediates required for biosynthesis of macromolecules such as RNA, DNA, lipids. Thus, mitochondrial metabolism plays a central role in glucose and lipid oxidation control, as well as in supporting proliferation of cells.

Under normal conditions, mitochondrial oxidation of acetyl-CoA and ATP synthesis are coupled in response to cellular energy needs. However, mitochondrial oxidation can be decoupled from ATP synthesis by mitochondrial uncouplers. Mitochondrial uncouplers facilitate the inward translocation of protons across mitochondrial inner membrane (not through the $F_oF_1$-ATP synthase), thus dissipate or reduce the proton gradient without generating ATP. Mitochondrial uncoupling could be mediated by protein mitochondrial uncouplers such as UCP1 protein, or chemical uncouplers such as DNP (dinitrophenol). As a result, mitochondrial uncouplers usually lead to the following effects: (1). reduction of mitochondrial energy efficiency, (2). increase of lipid and glucose oxidation, (3). activation of AMPK enzyme, (4). alteration of availability of metabolic intermediates for biomass biosynthesis required for cell proliferation. Consequently, mitochondrial uncoupling reduces intracellular lipid accumulation, and inhibits cell proliferation.

Metabolic diseases are a family of diseases characterized by symptoms of abnormal glucose and/or lipid metabolism, which share common causal factors of abnormal accumulation of intracellular lipid in cells of various tissues and insulin resistance. More specifically, the referred metabolic diseases include but are not limited to obesity (excessive fat accumulation in cells of adipose tissue), metabolic syndrome (insulin resistance in peripheral tissues, usually caused by ectopic fat accumulation in cells of liver, muscle, or adipose tissue), type 2 diabetes (insulin resistance in peripheral tissues usually caused by ectopic fat accumulation in cells of liver, muscle, or adipose tissue, and hyperglycemia caused by insulin resistance), the various known complications caused by type 2 diabetes, alcoholic fatty liver disease (ectopic lipid accumulation in liver cells), the various stages of non-alcoholic liver fatty liver disease (or NAFLD, caused by ectopic lipid accumulation in liver cells, the stages include hepatosteatosis, non-alcoholic steatohepatitis (NASH), cirrhosis, and NAFLD induced hepatocellular carcinoma (HCC)), and the various types of dyslipidemia (ectopic accumulation of lipid in cells of liver, muscle, heart, as a result of redistribution of lipid from adipose tissue to other tissues). Mitochondrial uncouplers, which reduce energy efficiency and boost futile lipid oxidation, would effectively reduce cellular accumulation of lipid. Moreover, recent studies have demonstrated that ectopic intracellular accumulation of lipid in liver and muscle, as well as excessive accumulation of lipid in adipose tissue are the fundamental cause of insulin resistance in various forms of metabolic diseases (Samuel V. T., et al., Lancet, 2010, 375:2267-77). Indeed, more recent studies have shown that chemical mitochondrial uncouplers are efficacious in preventing and treating metabolic diseases (Tao, H., Zhang, Y., Zeng, X., Shulman, G. I., and Jin, S. Nature Medicine 20: 1263-1269, 2014; Perry R J, Zhang D, Zhang X M, Boyer J L, Shulman G I., Science 2015 Mar. 13; 347(6227):1253-6), leading to: (1) reduction of lipid accumulation in various tissues, including adipose tissue, (2) reduction in insulin resistance, (3) reduction in blood glucose concentrations, (4) improvement in glycemic control and slowdown in disease progression. Importantly, using mitochondrial uncouplers for treating metabolic diseases has a number of appealing features; for example, since they correct the cause of insulin resistance (ectopic lipid accumulation), such an approach may provide a cure for some metabolic diseases. Despite the exciting advantage, currently no uncoupler drugs have been approved for clinical use or in clinical trials. Discovery of novel chemical mitochondrial uncouplers with a combination of favorable pharmamacokinetic and pharmacodynamic properties would be critical for developing mitochondrial uncoupling drugs for treatment of the above-mentioned metabolic diseases.

Cancer is a family of diseases characterized by uncontrolled growth and proliferation of cells of various tissue types, resulting from a combination of genetic mutations in oncogenes and tumor suppressor genes. It is well-accepted that one requirement of tumorigenesis is the alteration of cell metabolism. For rapid proliferation and growth, cancer cells require not only energy but also the building blocks (metabolic intermediates) for biosynthesis of macromolecules such as DNA and RNA. Metabolism in cancer cells is changed in such a way it could support both the energy need and the enormous need of the various metabolic intermediates (building blocks) for biosynthesis of macromolecules (Vander Heiden M G, Cantley L C, Thompson C B. Science. 2009 May 22; 324 (5930):1029-33). As a result, most cancers exhibit a unique cellular metabolic pattern called the Warburg effect, or aerobic glycolysis, which prevents the complete oxidation of glucose or lipid and allows for production of glucose metabolites for biosynthesis of macromolecules (Vander Heiden M G, et al., supra). Mitochondrial uncoupling reduces energy efficiency thereby undermining the energy requirement of cancer cells. In addition, mitochondrial uncoupling promotes the complete mitochondrial oxidation of glucose and lipid, thereby diminishing the production of metabolic intermediates essential for biosynthesis of macromolecules required for cell proliferation. Moreover, mitochondrial uncoupling could lead to AMPK activation, a known event for inhibiting cell growth. Indeed, prior documents showed that mitochondrial uncouplers exhibit anti-cancer activities (94697EP (315500)_WO_2004_006906)). Targeting cancer cells through mitochondrial uncoupling would deprive energy as well as biosynthetic metabolic intermediates that are absolutely essential for cancer cell growth and proliferation. Again, despite the appealing features of the new anti-cancer strategy, currently no mitochondrial uncoupling drug has been approved for cancer treatment and none are in clinical trials that are known to act by the mechanism of mitochondrial uncoupling. Discovery of new types of chemical mitochondrial uncouplers with a combination of favorable pharmacokinetic and pharmacodynamic properties is critical for the development of an anti-cancer drug for treating various types of cancers and other diseases.

Abnormal cell proliferation is also the underlying cause of a number of other pathological conditions, including but not limiting to skin diseases such as psoriasis and eczema. For example, psoriasis and eczema are immune diseases where immune cells infiltrate abnormally to skin, where they stimulate proliferation of surrounding epidermal stem cells. The symptoms of these diseases are characterized by excessive epidermal cell proliferation that is similar to wound healing. Thus, chemical uncouplers could be used to control abnormal cell proliferation, thereby treating these diseases.

In addition, mitochondrial uncoupling of cells of parasitic organisms can prevent the proliferation of these infected agents, thereby mitochondrial uncoupling is an effective way for treating infectious diseases in human and animals. In fact, mitochondrial uncoupler niclosamide is an FDA approved anthelmintic drug for treating flatworm infection in human. In addition, other types of mitochondrial uncouplers such as oxyclonazide are an anthelmintic drug for treating parasites in live stocks such as cow and horse. Thus, the compounds described in this patent could be effective in treating infectious diseases of non-viral parasites.

Mitochondria are ancient bacteria that formed a symbiotic relationship with host cells. Bacterial plasma membrane contains electron transport chain and ATP synthase that are similar to those of mitochondria, therefore compounds that impact mitochondrial uncoupling could be useful inhibitors of bacterial growth.

Various embodiments provide compounds with mitochondrial uncoupling activity. These compounds are useful for the prevention and treatment of bacterial infections; dermatological disorders; non-viral parasites; metabolic diseases or disorders and cancer, including, but not limited to, obesity, metabolic syndrome, type 2 diabetes, alcoholic fatty liver disease, non-alcoholic fatty liver diseases, dyslipidemia, primary cancer of various tissue origins, and metastatic cancer.

Compounds

In one embodiment, the present disclosure describes a compound of formula (I):

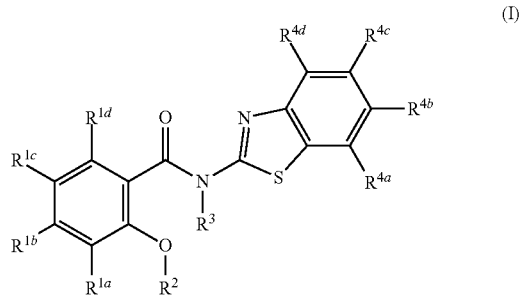

(I)

or a pharmaceutically acceptable salt, solvate, or prodrug thereof.

The substituent $R^{1a}$ of formula (I) is selected from the group consisting of hydrogen; optionally substituted $C_1$-$C_6$ alkyl; optionally substituted $C_2$-$C_6$ alkenyl; optionally substituted $C_2$-$C_6$ alkynyl; optionally substituted $C_3$-$C_{10}$ cycloalkyl; $((C_1$-$C_6$ alkylsulfonyl)amino)$C_1$-$C_6$alkyl; optionally substituted $C_3$-$C_{10}$ heterocyclyl; optionally substituted $C_3$-$C_{10}$ aryl; optionally substituted $C_3$-$C_{10}$ heteroaryl; $C_1$-$C_6$ perfluoroalkyl; halo; cyano; nitro; optionally substituted amino; —C(O)NHR$^5$; —C(O)NR$^5$R$^6$; —C(O)H; —C(O)R$^7$; —C(O)OH; and —C(O)OR$^5$.

Each of substituents $R^{1b}$, $R^{1c}$ and $R^{1d}$ of formula (I) is independently selected from the group consisting of: hydrogen; $C_1$-$C_6$ perfluoroalkyl; $C_1$-$C_6$ alkyl; $C_2$-$C_6$ alkenyl; $C_1$-$C_6$ alkynyl; $C_3$-$C_{10}$ cycloalkyl; cyano and halo.

Substituent $R^2$ of formula (I) is selected from the group consisting of hydrogen; mono-saccharide; di-saccharide; C(O)NR$^5$R$^6$; C(O)R$^7$; —P(O)(OH)$_2$; and —P(O)(ONa)$_2$; wherein the mono-saccharides and di-saccharide are attached to the phenolic oxygen at the anomeric center to form a glycosidic bond. Each of substituents $R^5$ and $R^6$ is independently selected from the group consisting of optionally substituted $C_1$-$C_6$ alkyl; and $C_1$-$C_6$ alkylsulfonyl. Alternatively $R^5$ and $R^6$ taken together with the nitrogen to which they are attached form an optionally substituted $C_3$-$C_6$ heterocyclyl. Substituent $R^7$ of formula (I) is selected from the group consisting of: optionally substituted (alkylamino) $C_1$-$C_6$ alkyl; and optionally substituted $C_3$-$C_6$ heterocyclyl.

Substituent $R^3$ of formula (I) is hydrogen, or alternatively, substituents $R^2$ and $R^3$ of formula (I) taken together are a carbonyl group and together with the atoms to which they are attached, form a six-membered heterocyclic carbamate.

Each of substituents $R^{4a}$, $R^{4b}$, $R^{4c}$ and $R^{4d}$ is independently selected from the group consisting of hydrogen; $C_1$-$C_6$ perfluoroalkyl; cyano; nitro; —CHF$_2$, $C_1$-$C_6$ alkyl, —OC$_1$-$C_6$-alkyl, —OCF$_3$, $C_3$-$C_{10}$ cycloalkyl, —CF$_3$, —SO$_2$CH$_3$ and halo.

Further embodiments describe the compound, according to formula (II):

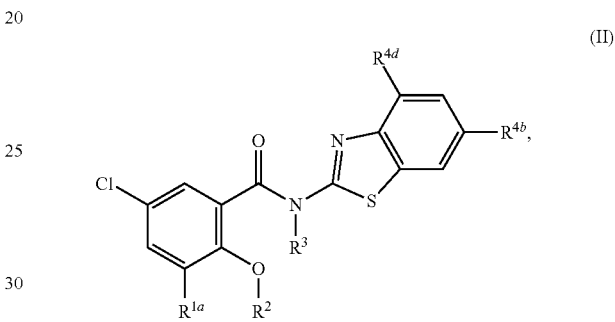

(II)

or a pharmaceutically acceptable salt, solvate, or prodrug thereof, wherein each of $R^{1a}$, $R^2$, $R^{4b}$, and $R^{4d}$ of formula (II) is as described previously for formula (I).

In some embodiments, $R^{1a}$ of formula (I) or (II) is selected from the group consisting of hydrogen; $C_1$-$C_6$ alkyl; $C_3$-$C_6$ cycloalkyl; cyano; hydroxyl $C_1$-$C_6$ alkyl; (N,N-dimethylamino)$C_1$-$C_6$ alkyl; halo; and ((C$_1$-$C_6$alkylsulfonyl)amino)$C_1$-$C_6$alkyl.

In some embodiments $R^2$ of formula (I) or formula (II) is selected from hydrogen; C(O)NR$^5$R$^6$; C(O)R$^7$; —P(O)(OH)$_2$; and —P(O)(ONa)$_2$. Substituents $R^5$ and $R^6$ taken together with the nitrogen to which they are attached form an optionally substituted $C_3$-$C_6$ heterocyclyl. Substituent $R^7$ is selected from the group consisting of (dimethylamino) methyl, and 2-pyrrolidinyl. Alternatively, $R^2$ and $R^3$ taken together are a carbonyl group and together with the atoms to which they are attached, form a six-membered heterocyclic carbamate.

In some embodiments, each of substituents $R^{4b}$ and $R^{4d}$ of formula (I) or formula (II) is independently selected from the group consisting of: hydrogen; trifluoromethyl; —OCF$_3$; —SO$_2$CH$_3$ and halo.

In some embodiments, $R^{1a}$ and $R^2$ of formula (I) or formula (II) are not both hydrogen.

Some embodiments describe the compounds of formula (I) wherein:

$R^{1a}$ is selected from the group consisting of hydrogen, methyl, ethyl, isopropyl, cyclopropyl, cyano, hydroxymethyl, halo, —CH$_2$N(CH$_3$)$_2$, —CH$_2$CH$_2$N(CH$_3$)$_2$, and —CH$_2$CH$_2$CH$_2$N(CH$_3$)$_2$, —CH$_2$CH$_2$CH$_2$NHS(O)$_2$CH$_3$;

each of $R^{1b}$, $R^{1c}$, and $R^{1d}$ is independently selected from the group selected from hydrogen and halo;

$R^2$ is selected from the group consisting of hydrogen, —P(O)(OH)$_2$, —P(O)(ONa)$_2$;

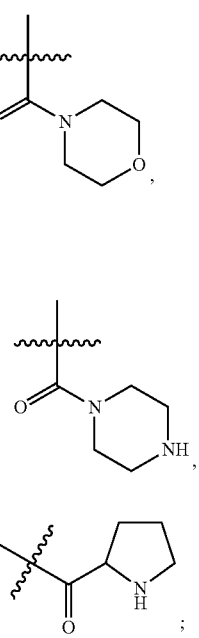

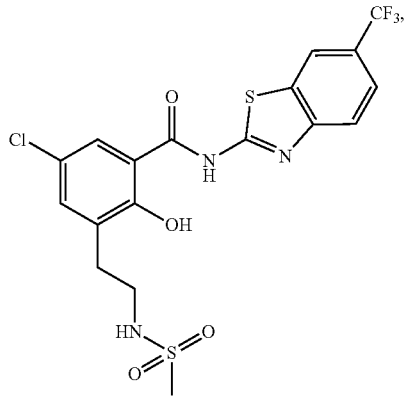

R³ is hydrogen, or alternatively, R² and R³ taken together are a carbonyl group and together with the atoms to which they are attached, form a six-membered heterocyclic carbamate; and each of $R^{4a}$, $R^{4b}$, $R^{4c}$, and $R^{4d}$ is independently selected from hydrogen, fluoro, OCF₃, —SO₂CH₃, and trifluoromethyl.

Some embodiments of the invention are directed to a compound of formula (I) selected from:

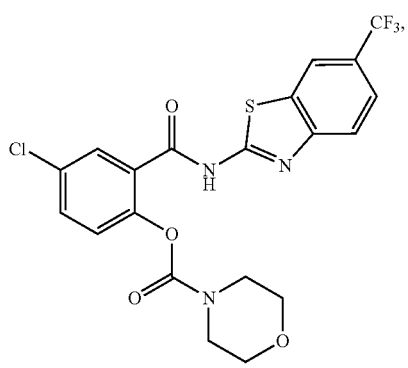

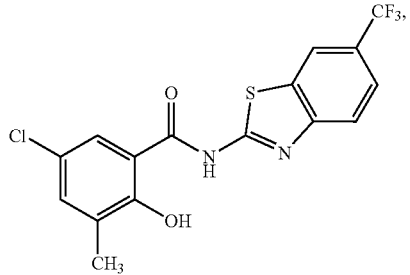

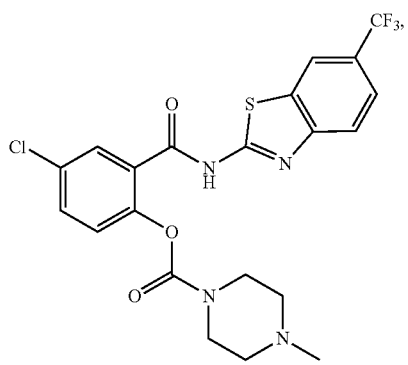

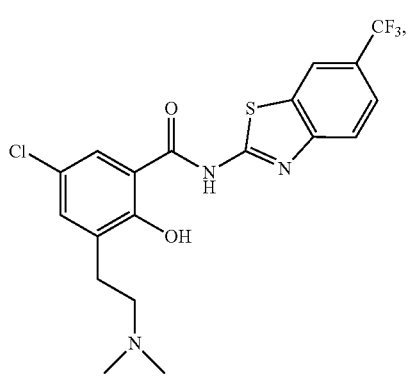

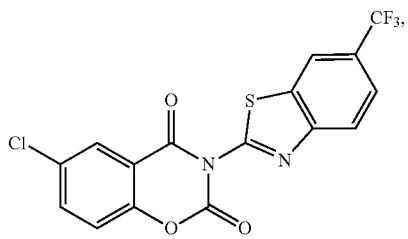

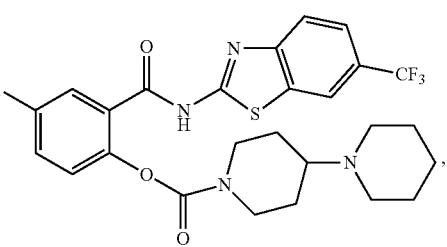

-continued
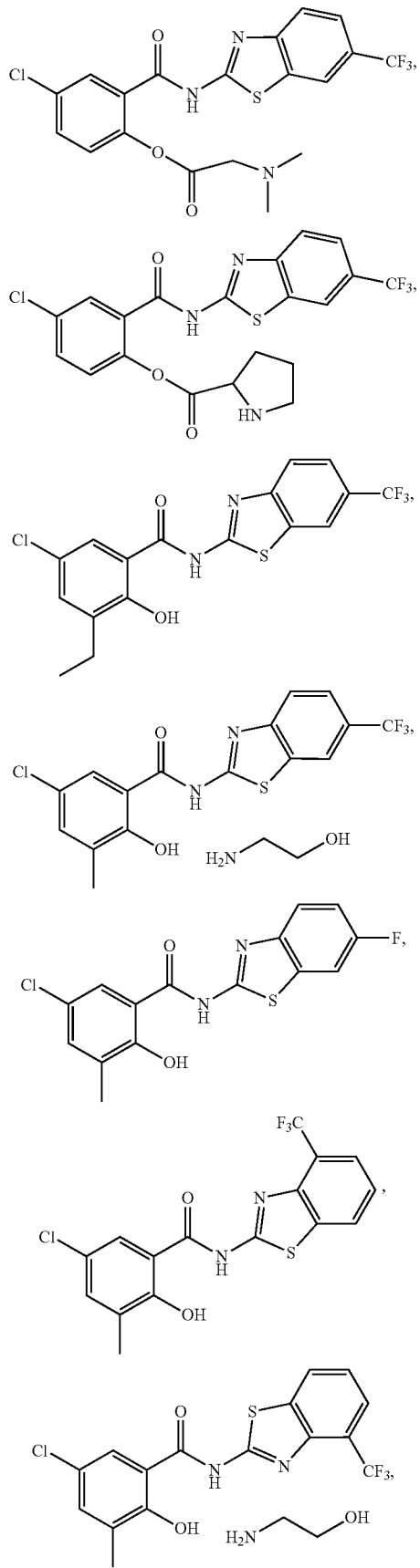
-continued
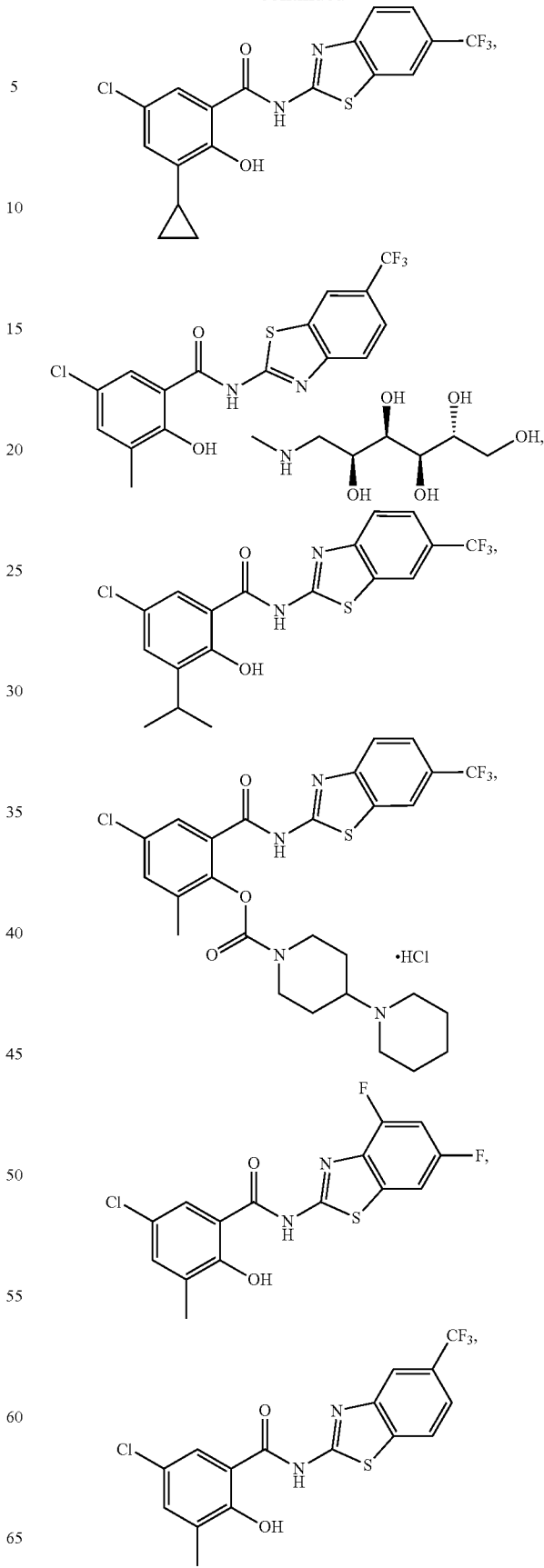

-continued
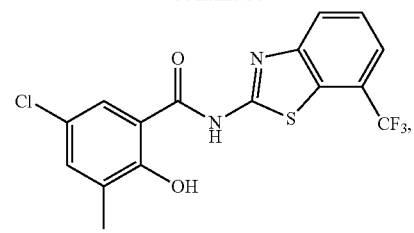
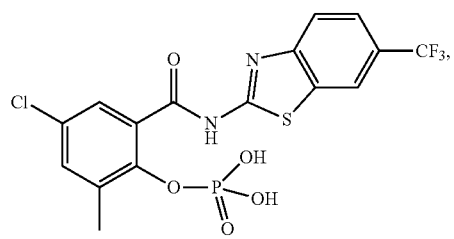
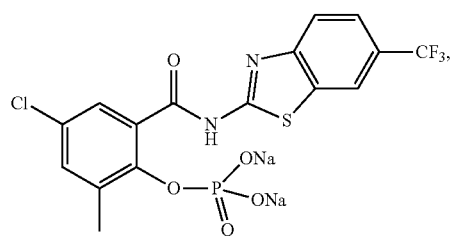
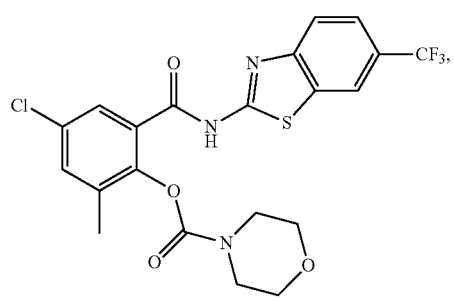
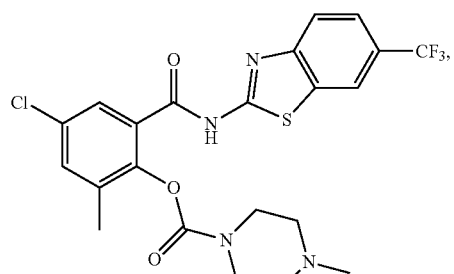
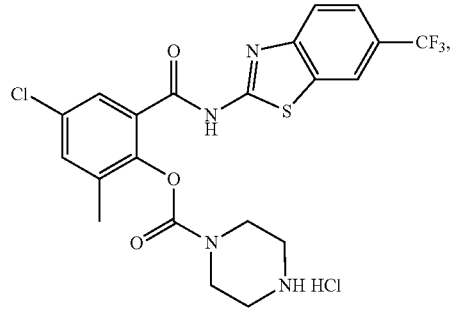
-continued
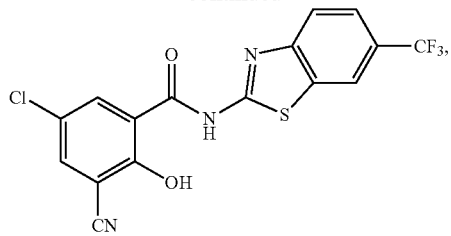
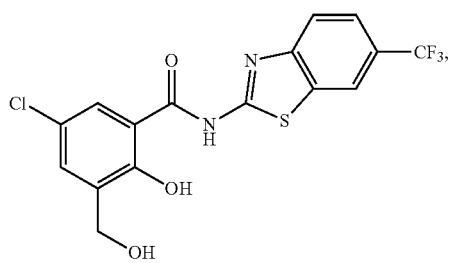
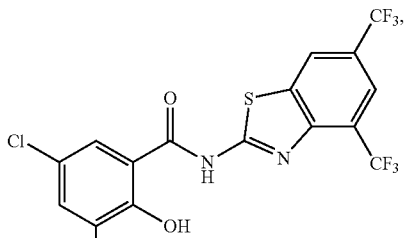
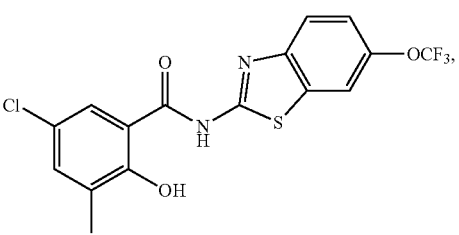
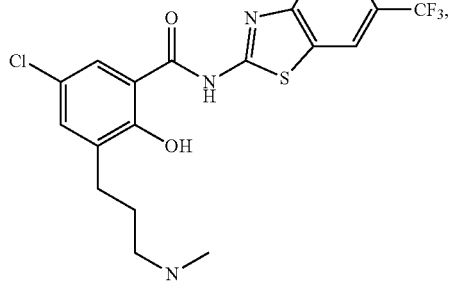
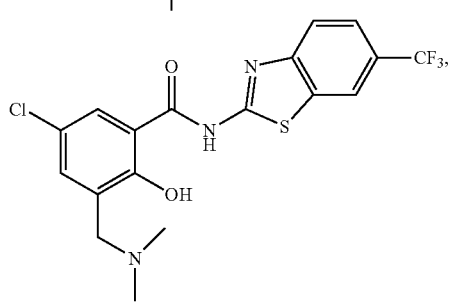

-continued

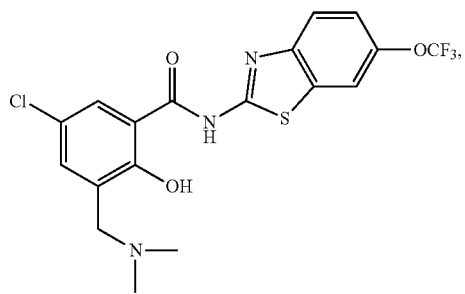

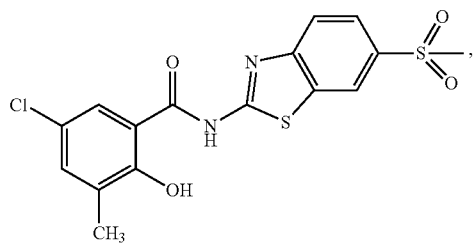

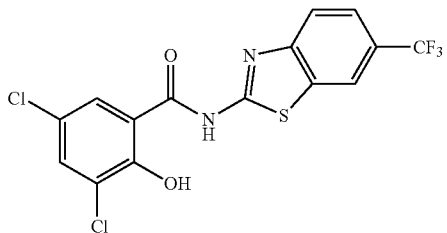

and a pharmaceutically acceptable salt, solvate, or prodrug thereof.

Some embodiments describe a compound of selected from the group consisting of

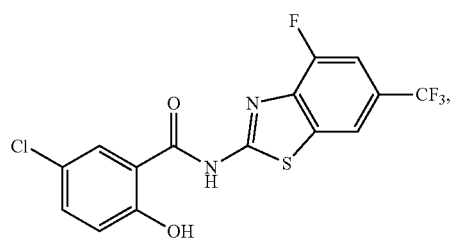

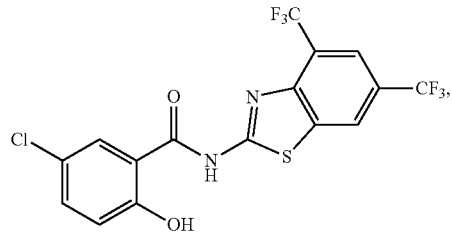

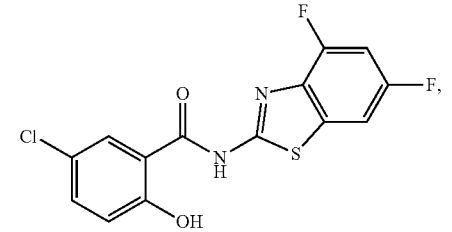

-continued

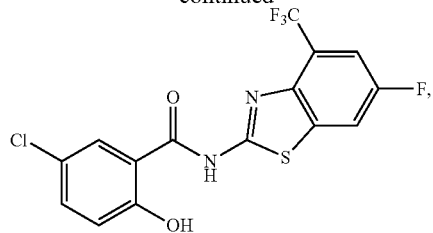

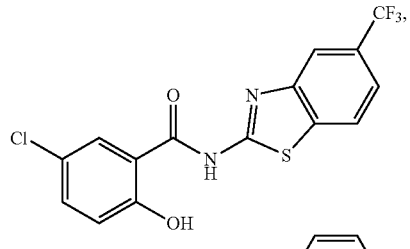

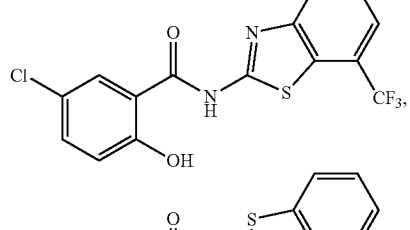

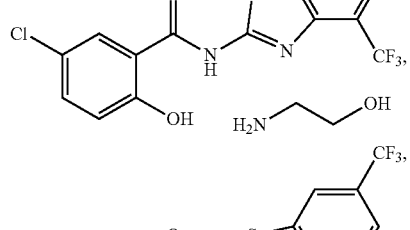

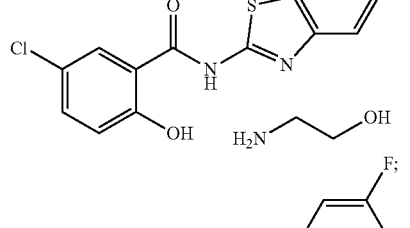

and a pharmaceutically acceptable salt, solvate, or prodrug thereof.

Some embodiments describe a compound of formula (III)

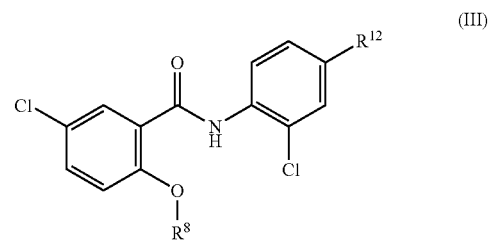

(III)

or a pharmaceutically acceptable salt, solvate, or prodrug thereof.

Substituent $R^8$ of formula (III) is selected from the group consisting of: $C(O)NR^9R^{10}$ and $C(O)R^{11}$.

Each of substituents $R^9$ and $R^{10}$ of formula(III) is independently selected from the group consisting of optionally substituted $C_1$-$C_6$ alkyl; and $C_1$-$C_6$ alkylsulfonyl. Alternatively $R^9$ and $R^{10}$ taken together with the nitrogen to which they are attached form an optionally substituted $C_3$-$C_6$ heterocyclyl.

Substituent of formula (III) is selected from the group consisting of: optionally substituted (alkylamino)$C_1$-$C_6$-alkyl; and optionally substituted $C_3$-$C_6$ heterocyclyl.

Substituent $R^{12}$ of formula (III) is selected from the group consisting of: $C_{1-6}$ perfluoroalkyl; halo; cyano; and nitro. In some embodiments $R^{12}$ of formula (III) is selected from the group consisting of $CF_3$; halo; cyano; and nitro.

In some embodiments $R^8$ of formula (III) is selected from the group consisting of $C(O)NR^9R^{10}$; and $C(O)R^{11}$. Substituent $R^9$ and $R^{10}$ taken together with the nitrogen to which they are attached form an optionally substituted $C_3$-$C_6$ heterocyclyl. Substituent $R^{11}$ is selected from the group consisting of (dimethylamino)methyl, and 2-pyrrolidinyl.

In some embodiments the compound of formula (III) is selected from

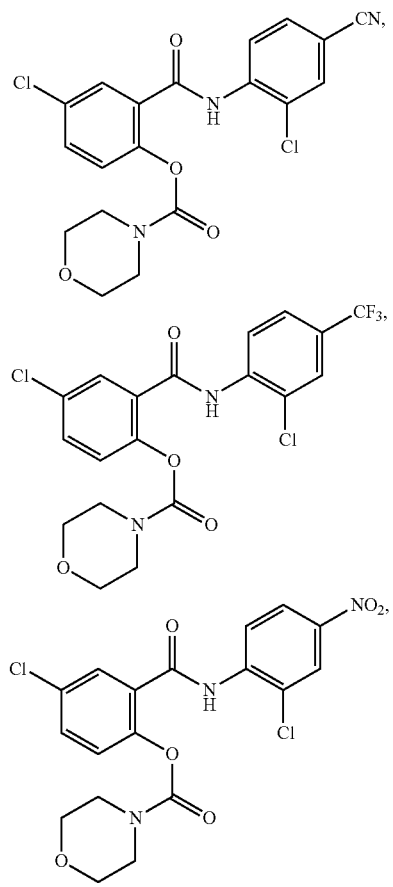

and a pharmaceutically acceptable salt, solvate, or prodrug thereof.

In one embodiment, the present disclosure describes compounds of the formula

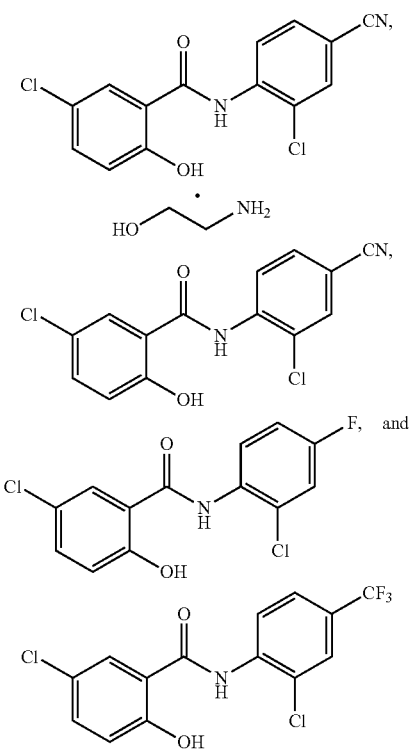

and a pharmaceutically acceptable salt, solvate, or prodrug thereof.

In one embodiment, the present disclosure describes a compound of formula (IV) or formula (V)

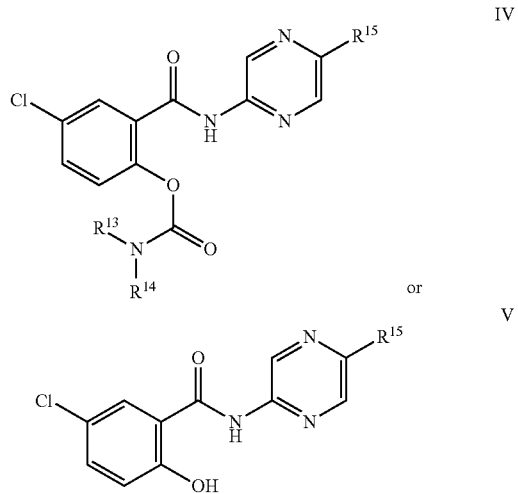

or a pharmaceutically acceptable salt, solvate, or prodrug thereof.

Each of substituents $R^{13}$ and $R^{14}$ of formula (IV) or formula (V) is independently selected from the group consisting of optionally substituted $C_1$-$C_6$ alkyl; and $C_1$-$C_6$ alkylsulfony. Alternatively $R^{13}$ and $R^{14}$ taken together with the nitrogen to which they are attached form an optionally substituted $C_3$-$C_6$ heterocyclyl.

Substituent $R^{15}$ is selected from the group consisting of $C_1$-$C_6$-perfluoroalkyl; nitro; and cyano.

In one embodiment, the compound of Formula (IV) is:

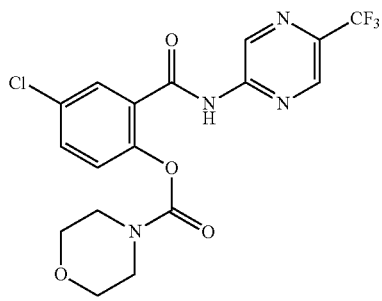 [SMILES: O=C(Nc1cnc(C(F)(F)F)cn1)c1cc(Cl)ccc1OC(=O)N1CCOCC1]

and a pharmaceutically acceptable salt, solvate, or prodrug thereof.

In one embodiment, the present disclosures describes a compound selected from the group consisting of

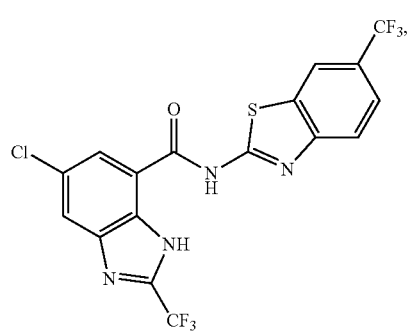

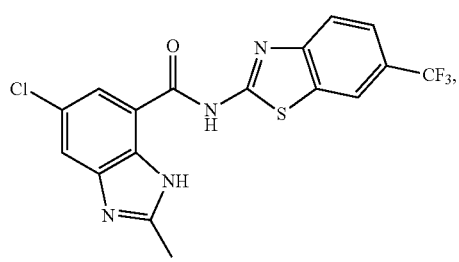

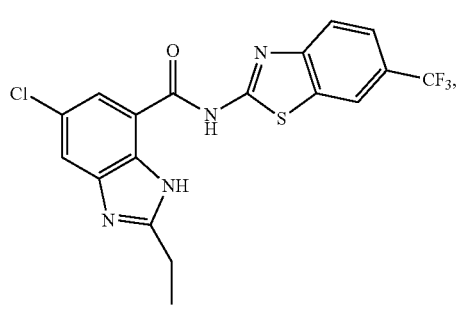

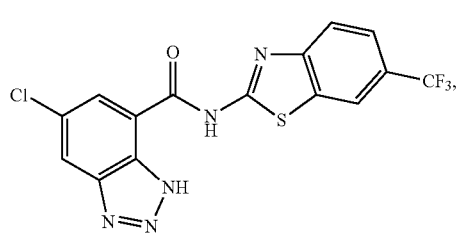

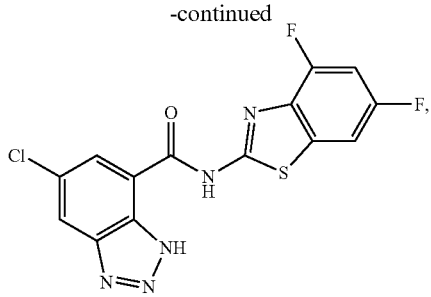

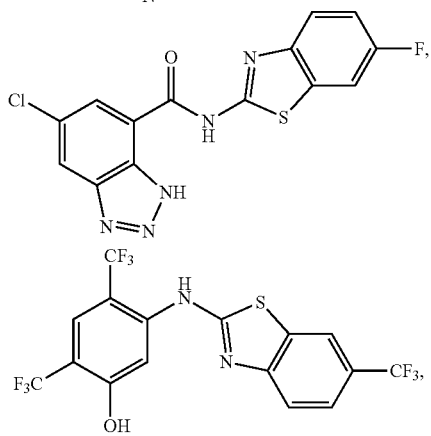

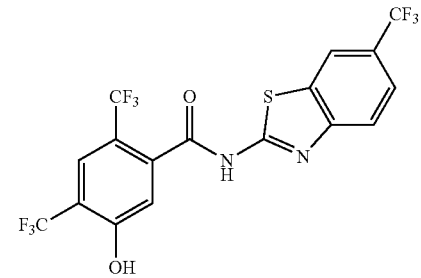

and a pharmaceutically acceptable salt, solvate, or prodrug thereof.

The compounds of the invention can possess one or more asymmetric carbon atoms and are thus capable of existing in the form of optical isomers as well as in the form of racemic or non-racemic mixtures thereof. The compounds of the invention (can be utilized in the present invention as a single isomer or as a mixture of stereochemical isomeric forms. Diastereoisomers, i.e., non-superimposable stereochemical isomers, can be separated by conventional means such as chromatography, distillation, crystallization or sublimation. The optical isomers can be obtained by resolution of the racemic mixtures according to conventional processes, for example by formation of diastereoisomeric salts by treatment with an optically active acid or base. Examples of appropriate acids include, without limitation, tartaric, diacetyltartaric, dibenzoyltartaric, ditoluoyltartaric and camphorsulfonic acid. The mixture of diastereomers can be separated by crystallization followed by liberation of the optically active bases from these salts. An alternative process for separation of optical isomers includes the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to obtain the enantiomerically pure compound. The optically active compounds of the invention can likewise be obtained by utilizing optically active starting materials. These isomers may be in the form of a free acid, a free base, an ester or a salt.

Compounds of the invention may be in the form of pharmaceutically acceptable salts. A pharmaceutically acceptable salt of the compounds of the invention includes acid addition salts and base addition salts. Pharmaceutically-acceptable salt embraces salts commonly used to form alkali metal salts and to form addition salts of free acids or free bases The nature of the salt is not critical, provided that it is pharmaceutically-acceptable. Suitable pharmaceutically-acceptable acid addition salts of the compounds of the invention may be prepared from an inorganic acid or an organic acid. Examples of such inorganic acids include, without limitation, hydrochloric, hydrobromic, hydroiodic, nitric, carbonic, sulfuric and phosphoric acid. Appropriate organic acids may be selected from aliphatic, cycloaliphatic, aromatic, arylaliphatic, heterocyclic, carboxylic and sulfonic classes of organic acids, examples of which include, without limitation, formic, acetic, propionic, succinic, glycolic, gluconic, maleic, embonic (pamoic), methanesulfonic, ethanesulfonic, 2-hydroxyethanesulfonic, pantothenic, benzenesulfonic, toluenesulfonic, sulfanilic, mesylic, cyclohexylaminosulfonic, stearic, algenic, β-hydroxybutyric, malonic, galactic, and galacturonic acid. Pharmaceutically-acceptable base addition salts for compounds described herein can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cyclo alkyl) amines, substituted cycloalkyl amines, disubstituted cycloalkyl amine, trisubstituted cycloalkyl amines, cycloalkenyl amines, di(cycloalkenyl) amines, tri (cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three sub stituents, together with the amino nitrogen, form a heterocyclic or heteroaryl group. Examples of suitable amines include, by way of example only, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like. It should also be understood that other carboxylic acid derivatives would be useful in the practice of this invention, for example, carboxylic acid amides, including carboxamides, lower alkyl carboxamides, dialkyl carboxamides, and the like.

Acceptable salts may be obtained using standard procedures well known in the art, for example by treating a sufficiently basic compound such as an amine with a suitable acid affording a physiologically acceptable anion. Alkali metal (for example, sodium, potassium or lithium) or alkaline earth metal (for example calcium) salts of organic (e.g., carboxylic) acids can also be made.

Compounds of the present invention may have prodrug forms. Any compound that will be converted in vivo to provide the bioactive agent is a prodrug within the scope and spirit of the invention. Various forms of prodrugs are well known in the art (see, for example, Medicinal Chemistry: Principles and Practice, F. D. King, ed., The Royal Society of Chemistry, Cambridge, UK, 1994; Hydrolysis in Drug and Prodrug Metabolism. Chemistry, Biochemistry and Enzymology, B. Testa, J. M. Mayer, VCHA and Wiley-VCH, Zurich, Switzerland, 2003; The Practice of Medicinal Chemistry, C. G. Wermuth, $2^{nd}$ ed., Academic Press, San Diego, Calif., 1999).

In some embodiments, a prodrug of the compounds of the present invention may take the form of a carbamate. For instance, a compound of formula (I) may have $R^2$ as $C(O)R_a$ wherein $R_a$ is amino (—$NH_2$), alkylamino, or arylamino. The alkylamino may be mono-substituted or di-substituted alkylamino groups. In some embodiments, the alkyl group has 1-10 carbons. In another example, $R_a$ maybe an optionally substituted $C_3$-$C_6$ heterocyclyl. Non-limiting examples of $R_a$ include —$NHCH_3$, —$NHCH_2CH_3$, —$NHCH_2CH_2CH_3$, —$N(CH_3)_2$, —$N(CH_2CH_3)$, and

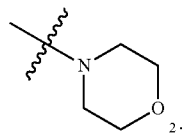

Scheme I illustrates suggested chemistry for the synthesis of ester and carbamate prodrugs of the benzamide compounds of the present disclosure:

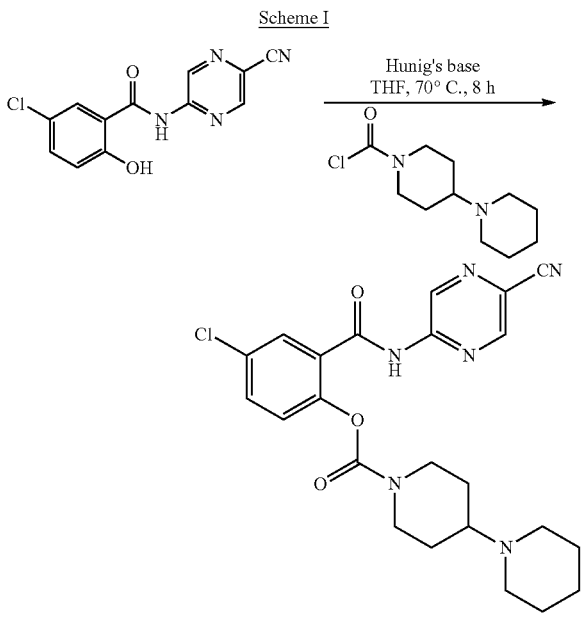

To an empty flask was added 5-chloro-N-(5-cyanopyrazin-2-yl)-2-hydroxybenzamide (200.0 mg, 0.728 mmol), followed by the addition of THF (5.0 mL) and Hunig's base (0.26 mL, 1.456 mmol). To this solution was added [1,4'-bipiperidine]-1'-carbonyl chloride (202 mg, 0.874 mmol). The reaction was stirred at 70° C. for 16 hours before silica gel was added. Solvent was then removed and the residue was purified via silica gel column chromatography to give 4-chloro-2-((5-cyanopyrazin-2-yl)carbamoyl)phenyl [1,4'-bipiperidine]-1'-carboxylate (183.0 mg, 54% yield).

Some embodiments describe a benzamide compound of embodiments herein, a pharmaceutically acceptable salt thereof, a hydrate thereof, or a prodrug thereof, wherein the benzamide compound contains a benzothiazole moiety. Scheme II illustrates suggested synthetic reactions relevant to benzothiazole synthesis.

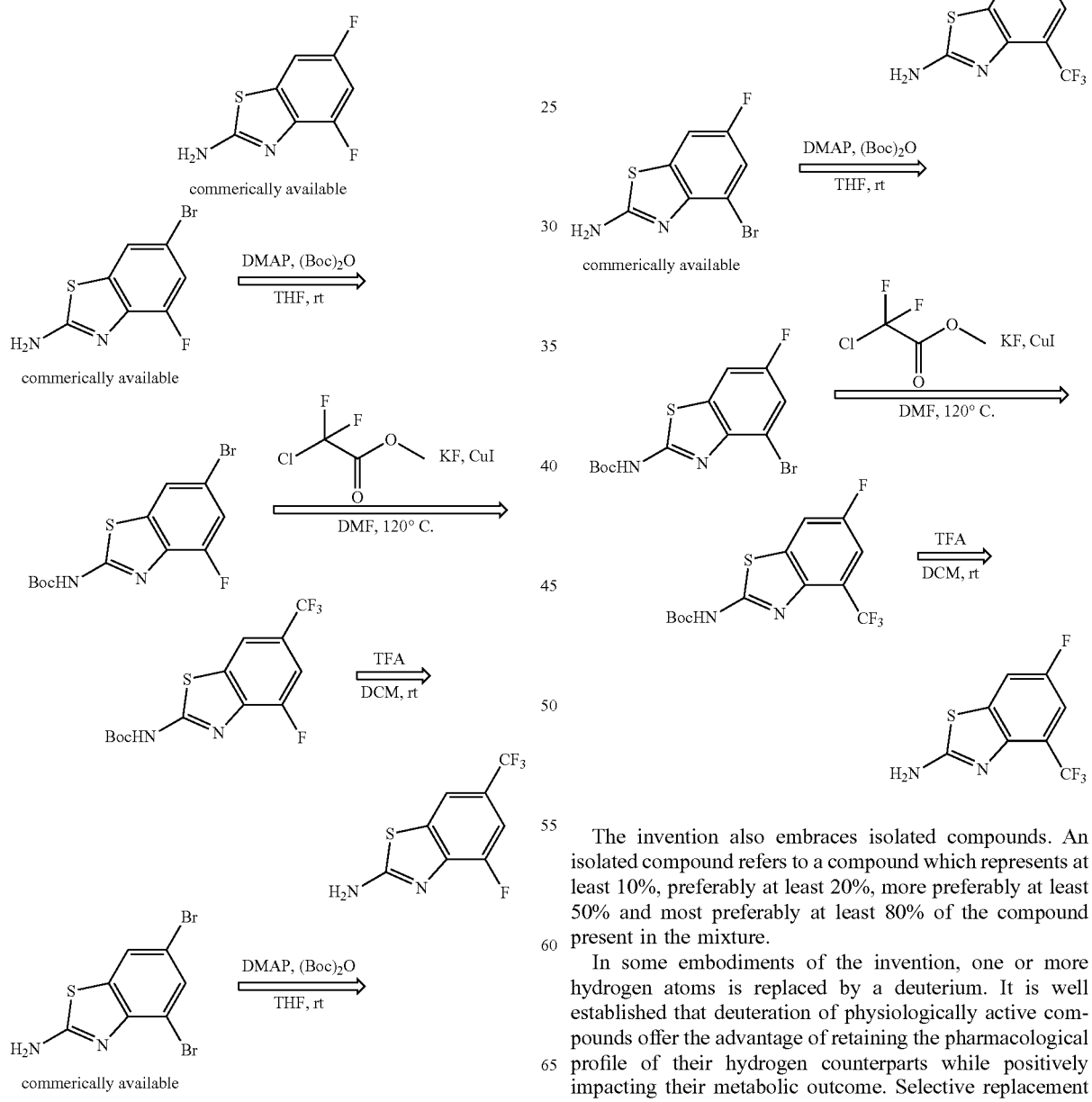

The invention also embraces isolated compounds. An isolated compound refers to a compound which represents at least 10%, preferably at least 20%, more preferably at least 50% and most preferably at least 80% of the compound present in the mixture.

In some embodiments of the invention, one or more hydrogen atoms is replaced by a deuterium. It is well established that deuteration of physiologically active compounds offer the advantage of retaining the pharmacological profile of their hydrogen counterparts while positively impacting their metabolic outcome. Selective replacement of one or more hydrogen with deuterium, in a compound of the present invention, could improve the safety, tolerability and efficacy of the compound when compared to its all hydrogen counterpart.

Methods for incorporation of deuterium into compounds is well established. Using metabolic studies establish in the art, the compound of the present invention can be tested to identify sites for selective placement of a deuterium isotope, wherein the isotope will not be metabolized. Moreover these studies identify sites of metabolism as the location where a deuterium atom would be placed.

Some embodiments describe a pharmaceutical composition comprising: a compound according to an embodiment described herein, a pharmaceutically acceptable salt thereof, a hydrate thereof, or a prodrug thereof; and a pharmaceutically acceptable carrier or diluent.

Compounds, or pharmaceutically acceptable salts thereof, can be formulated for oral, intravenous, intramuscular, subcutaneous or parenteral administration for the therapeutic or prophylactic treatment of diseases, disorders or infections described herein. For oral or parenteral administration, compounds of this invention can be mixed with conventional pharmaceutical carriers and excipients and used in the form of tablets, capsules, elixirs, suspensions, syrups, wafers and the like. The compositions comprising a compound of this invention will contain from about 0.1 to about 99% by weight of the active compound, and more generally from about 10 to about 30%.

The pharmaceutical preparations disclosed herein are prepared in accordance with standard procedures and are administered at dosages that are selected to reduce, prevent or eliminate the infection (See, e. g., Remington's Pharmaceutical Sciences, Mack Publishing Company, Easton, Pa. and Goodman and Gilman's. The Pharmaceutical Basis of Therapeutics, Pergamon Press, New York, N.Y., the contents of which are incorporated herein by reference, for a general description of the methods for administering various antimicrobial agents for human therapy). The compositions of the invention can be delivered using controlled (e.g., capsules) or sustained release delivery systems (e.g., bioerodable matrices).

The pharmaceutically acceptable compositions of the present invention comprise one or more compounds of the invention in association with one or more non-toxic, pharmaceutically acceptable carriers and/or diluents and/or adjuvants and/or excipients, collectively referred to herein as "carrier" materials, and if desired other active ingredients. The compositions may contain common carriers and excipients, such as corn starch or gelatin, lactose, sucrose, microcrystalline cellulose, kaolin, mannitol, dicalcium phosphate, sodium chloride and alginic acid. The compositions may contain croscarmellose sodium, microcrystalline cellulose, corn starch, sodium starch glycolate and alginic acid.

Tablet binders that can be included are acacia, methylcellulose, sodium carboxymethylcellulose, polyvinylpyrrolidone (Povidone), hydroxypropyl methylcellulose, sucrose, starch and ethylcellulose.

Lubricants that can be used include magnesium stearate or other metallic stearates, stearic acid, silicone fluid, talc, waxes, oils and colloidal silica.

Flavoring agents such as peppermint, oil of wintergreen, cherry flavoring or the like can also be used. It may also be desirable to add a coloring agent to make the dosage form more aesthetic in appearance or to help identify the product.

For oral use, solid formulations such as tablets and capsules are particularly useful. Sustained release or enterically coated preparations may also be devised. For pediatric and geriatric applications, suspensions, syrups and chewable tablets are especially suitable. For oral administration, the pharmaceutical compositions are in the form of, for example, a tablet, capsule, suspension or liquid. The pharmaceutical composition is preferably made in the form of a dosage unit containing a therapeutically effective amount of the active ingredient. Examples of such dosage units are tablets and capsules. For therapeutic purposes, the tablets and capsules which can contain, in addition to the active ingredient, conventional carriers such as binding agents, for example, acacia gum, gelatin, polyvinylpyrrolidone, sorbitol, or tragacanth; fillers, for example, calcium phosphate, glycine, lactose, maize-starch, sorbitol, or sucrose; lubricants, for example, magnesium stearate, polyethylene glycol, silica, or talc; disintegrants, for example, potato starch, flavoring or coloring agents, or acceptable wetting agents. Oral liquid preparations generally are in the form of aqueous or oily solutions, suspensions, emulsions, syrups or elixirs may contain conventional additives such as suspending agents, emulsifying agents, non-aqueous agents, preservatives, coloring agents and flavoring agents. Examples of additives for liquid preparations include acacia, almond oil, ethyl alcohol, fractionated coconut oil, gelatin, glucose syrup, glycerin, hydrogenated edible fats, lecithin, methyl cellulose, methyl or propyl parahydroxybenzoate, propylene glycol, sorbitol, or sorbic acid.

For intravenous (IV) use, a compound according to the invention can be dissolved or suspended in any of the commonly used intravenous fluids and administered by infusion. Intravenous fluids include, without limitation, physiological saline or Ringer's solution. Intravenous administration may be accomplished by using, without limitation, syringe, minipump or intravenous line.

Formulations for parenteral administration can be in the form of aqueous or non-aqueous isotonic sterile injection solutions or suspensions. These solutions or suspensions can be prepared from sterile powders or granules having one or more of the carriers mentioned for use in the formulations for oral administration. The compounds can be dissolved in polyethylene glycol, propylene glycol, ethanol, corn oil, benzyl alcohol, sodium chloride, and/or various buffers.

For intramuscular preparations, a sterile formulation of a compound or a suitable soluble salt form of the compound, for example the hydrochloride salt, can be dissolved and administered in a pharmaceutical diluent such as Water-for-Injection (WFI), physiological saline or 5% glucose. A suitable insoluble form of the compound may be prepared and administered as a suspension in an aqueous base or a pharmaceutically acceptable oil base, e.g., an ester of a long chain fatty acid such as ethyl oleate.

A dose of an intravenous, intramuscular or parental formulation of a compound may be administered as a bolus or by slow infusion. A bolus is a dose that is administered in less than 30 minutes. In a preferred embodiment, a bolus is administered in less than 15 or less than 10 minutes. In a more preferred embodiment, a bolus is administered in less than 5 minutes. In an even more preferred embodiment, a bolus is administered in one minute or less. An infusion is a dose that is administered at a rate of 30 minutes or greater. In a preferred embodiment, the infusion is one hour or greater. In another embodiment, the infusion is substantially constant.

For topical use the compounds of the present invention can also be prepared in suitable forms to be applied to the skin, or mucus membranes of the nose and throat, and can take the form of creams, ointments, liquid sprays or inhalants, lozenges, or throat paints. Such topical formulations further can include chemical compounds such as dimethylsulfoxide (DMSO) to facilitate surface penetration of the active ingredient.

For application to the eyes or ears, the compounds of the present invention can be presented in liquid or semi-liquid form formulated in hydrophobic or hydrophilic bases as ointments, creams, lotions, paints or powders.

For rectal administration the compounds of the present invention can be administered in the form of suppositories admixed with conventional carriers such as cocoa butter, wax or other glyceride.

Alternatively, the compounds of the present invention can be in powder form for reconstitution in the appropriate pharmaceutically acceptable carrier at the time of delivery. In another embodiment, the unit dosage form of the compound can be a solution of the compound or preferably a salt thereof in a suitable diluent in sterile, hermetically sealed ampoules or sterile syringes. The concentration of the compound in the unit dosage may vary, e.g. from about 1 percent to about 50 percent, depending on the compound used and its solubility and the dose desired by the physician.

Methods of Treatment

In some embodiments, a method of treating a metabolic disease or disorder characterized by insulin resistance or by abnormal accumulation of lipid in tissue, or a disease or a disorder in which insulin resistance or abnormal accumulation of lipid in tissue is a symptom, or treating cancer or hyperplasia, in a subject, comprises administering to the subject a therapeutically effective amount of a compound or a pharmaceutical composition according to an embodiment described herein. In some embodiments, the metabolic disease or disorder is type 2 diabetes, or a disease characterized by insulin resistance or hyperglycemia.

In some embodiments, the metabolic disease is a complication caused by type 2 diabetes, selected from the group consisting of diabetes-induced cardiovascular diseases, neurodegenerative disorders, atherosclerosis, hypertension, coronary heart diseases, nephropathy, retinopathy, neuropathy, and diabetic heart failure. In some embodiments, the metabolic disease or disorder is obesity or obesity related complications.

In some embodiments, the metabolic disease or disorder is non-alcoholic fatty liver disease (NAFLD), comprising at least one prognosis stage of this disease selected from the group consisting of hepatic steatosis, non-alcoholic steatohepatitis (NASH), cirrhosis, and NAFLD induced hepatocellular carcinoma (HCC). In some embodiments, the metabolic disease or disorder is alcoholic fatty liver disease, or a complication caused by alcoholic fatty liver diseases. In some embodiments, the complication of alcoholic fatty liver disease comprises alcoholic hepatitis, cirrhosis, or a combination thereof.

In some embodiments, the metabolic disease or disorder is dyslipidemia, or a complication caused by dyslipidemia. In some embodiments, the cancer is a primary cancer selected from the group consisting of hepatocellular carcinoma, colorectal carcinoma, pancreatic cancer, breast cancer, prostate cancer, leukemia, lymphoma, melanoma, ovarian cancer, and lung cancer. In some embodiments, the cancer is a metastatic cancer originated from a primary tumor of other tissue types. In some embodiments, the metastatic sites are selected from the group consisting of liver, lung and the intraperitoneal cavity.

In some embodiments, the compound of embodiments described herein is administered in combination with a second agent indicated for the above-mentioned disorders or diseases, either concomitant with, prior to, or after the administration of the second agent. In some embodiments, the second agent is an anti-diabetic agent selected from the group consisting of metformin, insulin, insulin analogs, sulfonylureas, biguanides, meglitinides, thiazolidinediones, alpha glucosidase inhibitors, GLP-1 agonists, SGLT2 inhibitors and DPP-4 inhibitors. In some embodiments, the second agent is an anti-obesity agent. In some embodiments, the second agent is an anti-nonalcoholic fatty liver disease agent. In some embodiments, the second agent is anti-alcoholic fatty liver disease agent. In some embodiments, the second agent is an anti-dyslipidemia agent.

In some embodiments, the mitochondrial uncoupling agent is administered in combination with a second anti-non-alcoholic fatty liver disease agent. In some embodiments, the mitochondrial uncoupling agent is administered in combination with a second anti-alcoholic fatty liver disease agent. In some embodiments, the mitochondrial uncoupling agent is administered in combination with a second anti-dyslipidemia agent.

In some embodiments, the compound may be administered in combination with a second anti-cancer agent or anti-cancer regimen. In some embodiments, the compound may be administered prior to, concomitantly with, or subsequently to administration of the second anti-metabolic disease or anti-cancer agent.

In some embodiments, the subject is a mammalian animal. In some embodiments, the subject is a human. In some embodiments, the compound described herein is used as a veterinarian drug to treat diabetes or a diabetes-associated disease, and the subject is a mammalian animal.

Some embodiments are directed to a method for long-term disease management of a metabolic disease or disorder comprising administering to a subject in need of such long-term management an effective amount of a compound or a composition described herein. In some embodiments, a method for long-term disease management of a metabolic disease or disorder, or for long-term disease management of cancer, comprises administering to a subject in need of such long-term management an effective amount of a compound or a pharmaceutical composition according to any of the embodiments described herein. In some embodiments, the metabolic disease or disorder is obesity, obesity-related complications, type 2 diabetes, or type 2 diabetes related complications. In some embodiments, the cancer is any primary tumor or metastatic tumor.

In some embodiments, the present disclosure describes the use of a compound according to any of the embodiments described herein in the manufacture of a medicament for treatment of diabetes, obesity, non-alcoholic fatty liver disease, alcoholic fatty liver disease, dyslipidemia, or a disease where insulin resistance or abnormal lipid accumulation in tissue is a symptom, or related disorders or complications, including, but not limited to, hepatic steatosis, non-alcoholic steatohepatitis (NASH), cirrhosis, or NAFLD induced hepatocellular carcinoma (HCC). In some embodiments, the compound of embodiments herein may be used to manufacture a medicament for the treatment of cancer, a disease where cell proliferation (hyperplasia) is a symptom, or cancer or hyperplasia related complications.

Some embodiments herein are directed to a method of treating or preventing a metabolic disease or disorder in a subject, comprising administering to the subject a therapeutically effective amount of a compound or pharmaceutical composition described herein.

Some embodiments herein provide for a method of treating and alleviating the symptoms of obesity (characterized by excessive accumulation of lipid in adipocytes), pre-type 2 diabetes (characterized by insulin resistance usually caused by ectopic accumulation of lipid in cells of liver and muscle), type 2 diabetes (characterized by insulin resistance and hyperglycemia), non-alcoholic fatty liver diseases or alcoholic fatty liver disease (characterized by abnormal accumulation of lipid in liver), dyslipidemia (characterized by abnormal lipid deposit in tissue other than adipose), and one or more complications of the above mentioned metabolic disorders, including, but not limited to, hypertension, cardiovascular diseases, nephropathy, and neuropathy comprising administering to the subject a therapeutically effective amount of a compound or pharmaceutical composition described herein. These diseases or disorders may be caused by dietary, environmental, medical and/or genetic factors. The methods described herein may also be used for prevention of the above-mentioned metabolic diseases for a subject with risk factors including, but not limited to, dietary, environmental, medical, and genetic predispositions. In addition, some embodiments provide a method for long-term chronic disease management and longevity management by reducing insulin resistance or reducing glucose levels in the blood.

In some embodiments, the metabolic disease or disorder is type 2 diabetes, or related diseases leading to insulin resistance or hyperglycemia. In some embodiments, the metabolic disease or disorder is obesity or one or more obesity related complications.

In some embodiments, the metabolic disease or disorder is non-alcoholic fatty liver disease, (NAFLD), including nonalcoholic steatohepatitis (NASH) and cirrhosis, or alcoholic fatty liver disease (AFLD). In some embodiments, the metabolic disease or disorder is hepatic steatosis, non-alcoholic steatohepatitis (NASH), cirrhosis, or NAFLD induced hepatocellular carcinoma (HCC).

In some embodiments, the metabolic diseases or disorder is one or more complications of type 2 diabetes including, but not limited to, type 2 diabetes induced hypertension, cardiovascular disease, nephropathy, atherosclerosis, dyslipidemia, retinopathy, neurodegenerative disorders, diabetic heart failure, and neuropathy. In some embodiments, the metabolic disease or disorder is pre-type 2 diabetes. In some embodiments, the metabolic disease or disorder is dyslipidemia.

In some embodiments, the disease to be treated may be a mitochondrial disorder. In some embodiments, the metabolic disorder may be LHON (leber heredity optic neuropathy), MELAS (mitochondrial myopathy, mitochondrial encephalomyopathy, lactic acidosis and stroke-like episodes), MERRF (myoclonic epilepsy and ragged red muscle fiber), Leigh Syndrome, MILS (maternally inherited Leigh Syndrome), NARP (neurogenic muscle weakness, ataxia and retinitis pigmentosa), FBSN (familial bilateral striatal necrosis), or KSS (Kearns Sayre Syndrome).

Some embodiments are directed to a method of treating or preventing cancer in a subject, comprising administering to the subject a therapeutically effective amount of a mitochondrial uncoupling agent or composition described herein. In some embodiments, the cancer may be primary cancer or metastatic cancer. In some embodiments, the cancer is primary cancer including but not limited to hepatocellular carcinoma, colorectal carcinoma, pancreatic cancer, breast cancer, prostate cancer, leukemia, lymphoma, melanoma, ovarian cancer, lung cancer. In some embodiments, the cancer is metastatic liver cancer originated from the primary tumor of other tissue types. In some embodiments, the cancer is metastatic lung cancer originated from the primary tumor of other tissue types. In some embodiments, the cancer is metastatic cancer to other sites including intraperitoneal cavity.

Some embodiments are directed to a method of treating or preventing a dermatological disorder in a subject, comprising administering to the subject a therapeutically effective amount of a mitochondrial uncoupling agent or composition described herein. In some embodiments, the dermatological disorder is eczema, dyshidrotic eczema, seborrheic eczema psoriasis, rosacea, dermatitis and atopic dermatitis.

Some embodiments are directed to a method of treating or preventing an infectious disease of non-viral parasites in a subject, comprising administering to the subject a therapeutically effective amount of a mitochondrial uncoupling agent or composition described herein.

In some embodiments, the disease to be treated may be a heart disorder comprising administering to the subject a therapeutically effective amount of a compound or pharmaceutical composition described herein. In some embodiments, the heart disorder may be hypertension or cardiovascular disease. In some embodiments, the disease to be treated may be a central nervous system (CNS) disease. In some embodiments, the CNS disease may be stroke, Alzheimer's, Parkinson's, Huntington's, or ALS (amyotropic lateral sclerosis).

In some embodiments, the disease to be treated may be a disorder associated with increased ROS (reactive oxygen species) production comprising administering to the subject a therapeutically effective amount of a compound or pharmaceutical composition described herein. Increased ROS has been associated with aging, Alzheimer's disease, Parkinson's disease, Huntington's disease, ALS (amyotropic lateral sclerosis), mitochondrial diseases, and various cancers.

The compounds and compositions described herein may be administered by oral, parenteral (e.g., intramuscular, intraperitoneal, intravenous, ICV, intracisternal injection or infusion, subcutaneous injection, or implant), by inhalation spray, ophthalmic, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. The compounds and compositions described herein may also be formulated as a controlled-release formulation.

The compounds described herein may be administered topically and can be formulated into a variety of topically administrable compositions comprising an active ingredient and a dermatologically acceptable base and/or an ophthalmically acceptable base. Such compositions can be formulated, e.g., as solutions, suspensions, spray, lotions, gels, pastes, medicated sticks, balms, shampoos, soap bars, liquid soaps, creams or ointments. In one embodiment, the composition is the form of an ointment that can be applied in or around the eye of a mammal, including a human.

In some embodiments, a dermatologically and/or ophthalmically acceptable base includes a pharmaceutically acceptable ointment base. Examples of suitable ointment bases include, but are not limited to oleaginous ointment bases such as petrolatum (e.g., liquid petrolatum or white petrolatum), plastibase, hard paraffin, white soft paraffin, yellow soft paraffin, liquid paraffin, emulsifying wax, microcrystalline wax, white bees wax, yellow bees wax, carnauba wax, wool wax (wool fat), mineral oil, olive oil, purified lanolin, anhydrous lanolin, and water soluble ointment bases such as polyethylene glycol (e.g., polyethylene glycol 400 or polyethylene glycol 3350), propylene glycol, polyoxyethylene, polyoxypropylene, or any combinations thereof.

In some embodiments, a dermatologically and/or ophthalmically acceptable base includes one or more polymers as suspending agents. Useful polymers include, but are not limited to, water-soluble polymers such as cellulosic polymers, e.g., hydroxypropyl methylcellulose, and water-insoluble polymers such as cross-linked carboxyl-containing polymers. A dermatologically and/or ophthalmically acceptable base can also include a dermatologically and/or ophthalmically acceptable mucoadhesive polymer, e.g., carboxymethylcellulose, carbomer (acrylic acid polymer), carbopol (copolymers or acrylic acid crosslinked with a polyakenyl polyether), poly(methylmethacrylate), polyacrylamide, polycarbophil, acrylic acid/butyl acrylate copolymer, sodium alginate, or dextran.

In some embodiments, a dermatologically and/or ophthalmically acceptable base includes one or more viscosity enhancing agents. Examples of suitable viscosity enhancing agents include, but are not limited to, methyl cellulose, xanthan gum, gum tragacanth, carboxymethyl cellulose, silica, silicone, hydroxypropyl cellulose, hydroxypropylmethyl cellulose, hydroxypropylmethyl cellulose acetate stearate, hydroxypropylmethyl cellulose phthalate, carbomer, polyvinyl alcohol, alginates, acacia, chitosans, acacia, corn starch, gelatin, or combinations thereof.

In some embodiments, a dermatologically and/or ophthalmically acceptable base includes one or more dermatologically and/or ophthalmically acceptable pH adjusting agents or buffering agents, including, but not limited to, acids such as acetic, boric, citric, lactic, phosphoric and hydrochloric acids; bases such as sodium hydroxide, sodium phosphate, sodium borate, sodium citrate, sodium acetate, sodium, lactate and tris-hydroxymethylaminomethane; and buffers such as citrate/dextrose, sodium bicarbonate and ammonium chloride. Such acids, bases and buffers are included in an amount required to maintain pH of the composition in a dermatologically and/or ophthalmically acceptable range.

In some embodiments, a dermatologically and/or ophthalmically acceptable base includes one or more dermatologically and/or ophthalmically acceptable salts in an amount required to bring osmolality of the composition into a dermatologically and/or ophthalmically acceptable range. Such salts include, but are not limited to, those having sodium, potassium or ammonium cations and chloride, citrate, ascorbate, borate, phosphate, bicarbonate, sulfate, thiosulfate or bisulfite anions; specific salts include, e.g., sodium chloride, potassium chloride, sodium thiosulfate, sodium bisulfite, and ammonium sulfate.

In some embodiments, a dermatologically and/or ophthalmically acceptable base includes one or more dermatologically and/or ophthalmically acceptable preservatives to inhibit microbial activity. Suitable preservatives include, but are not limited to, mercury-containing substances such as merfen and thiomersal; stabilized chlorine dioxide; and quaternary ammonium compounds such as benzalkonium chloride, cetyltrimethylammonium bromide and cetylpyridinium chloride.

In further embodiments, a dermatologically and/or ophthalmically acceptable base includes one or more dermatologically and/or ophthalmically acceptable surfactants to enhance physical stability, or for other purposes. Suitable nonionic surfactants include isohexadecane, cyclomethicone, copolymers of ethylene glycol and propylene glycol, polyoxyethylerie fatty acid glycerides and vegetable oils, e.g., polyoxyethylene (60) hydrogenated castor oil; and polyoxyethylerie alkylethers and alkylphenyl ethers, e.g., octoxynol 10, octoxynol 40.

In further embodiments, a dermatologically and/or ophthalmically acceptable base includes one or more dermatologically and/or ophthalmically acceptable penetration enhancers to enhance physical stability, or for other purposes. Penetration enhancers are substances which enhance passage of topically-applied compounds into the stratum, corneum of the skin and therefrom into the epidermis and dermis. Examples include, but are not limited to: dimethyl isosorbide, ethoxydiglycol, 1-dodecylazacycloheptan-2-one, propylene glycol, oleyl alcohol, polyoxyethylene ester, sorbitan mono-9-octadecenoate, poly(oxy-1,2-ethanediyl) and derivatives thereof, ethanol, glyceryl monoethyl ether, monoglycerides, isopropylmyristate, lauryl alcohol, lauric acid, lauryl lactate, terpinol, menthol, D-limonene, beta-cyclodextrin, DMSO (dimethyl sulfoxide), polysorbates, fatty acids (e.g., oleic), bile salts, N-methylpyrrolidone, polyglycosylated glycerides, 1-dodecylazacycloheptan-2-one (Azone®), Cyclopentadecalactone (CPE-215®), Alkyl-2-(N,N-disubstituted amino)-alkanoate ester (NexAct®), 2-(n-nonyl)-1,3-dioxolane (DEPA®), and penetration enhancers shown for example in U.S. Pat. Nos. 3,909,816; 4,405,616; 4,801,586; 4,861,764; 4,886,783; 4,983,396; 5,118,845; 5,196,410, 8,486,374 and 8,741,265, each of which is hereby expressly incorporated herein by reference in its entirety.

In further embodiments, a dermatologically and/or ophthalmically acceptable base includes one or more dermatologically and/or ophthalmically acceptable permability enhancers to enhance physical stability, or for other purposes. A variety of classes of compounds may serve as suitable permeability enhancers according to the invention. A first category includes fatty acids and salts and esters thereof, including mono-, di-, and triglycerides. Medium chain length fatty acids, especially C8 and C10 acids, and their salts and esters are particularly useful. Suitable specific examples include sodium caprylate, sodium caprate, CAPMUL® glycerides (available from Abitec of Columbus, Ohio), LABRASOL® glycerides (PEG-8 caprylic/capric glycerides, available from Gattefosse SAS of Saint Priest, Cedex, France), GELUCIRE® 44/14 (PEG-32 glyceryl laurate EP, available from Gattefosse), other glycerides & fatty acid esters, CREMOPHOR® (BASF, Ludwigshafen, Germany), D-α-tocopheryl polyethylene glycol 1000 succinate, vegetable oils, polyoxylglycerides, and medium chain mono- and diacylglycerides.

One example of this class, CAPMUL® MCM L8 (glycerol monocaprylate) (available from Abitec of Columbus, Ohio), is composed of mono- and diglycerides of medium chain fatty acids (mainly caprylic, with some capric) and 7% maximum free glycerol. It contains at least 44% alpha monoglycerides (as caprylate).

Other examples of this class of enhancers include GATTEFOSSE compositions 61A through 61H which are proprietary to Gattefosse SAS, but generally are composed of mixtures containing one or more of medium chain mono-, di-, or triglycerides, polysorbate derivatives, polyoxyl castor oil derivatives, polyethylene glycol derivatives including polyethylene glycol glycerides, polyoxyl ethers, vegetable oils, glycerin, and similar GRAS (generally regarded as safe) lipidic components in varying amounts. These components are part of individual commercial products such as CAPRYOL™ 90, CAPRYOL™ PGMC, LAUROGLYCOL™ 90, GELUCIRE® 44/14, Plurol Oleique CC497, LABRASOL®, LABRAFIL® M1944CS (apricot kernel oil PEG-6 esters), Transcutol HP, Peceol, and Maisine 35-1, all of which are available from Gattefosse SAS.

While not falling directly within this class, glycerol itself has been found to impart excellent permeability enhancement, particularly for neuraminidase inhibitors. This result was not anticipated as glycerol is not considered a permeability enhancer.

A second category of enhancers includes surfactants having a steroidal structure, such as bile acid salts. Examples of suitable compounds include sodium cholate, sodium deoxycholate, glycocholate, glycoursodeoxycholate, taurocholate, taurodeoxycholate, and steroid detergents/bile salts. Other surfactants may also be suitable permeability enhancers, including cationic, anionic, and nonionic surfactants. Examples include polysorbate 80, hexadecyldimethylbenzylammonium chloride, N-hexadecylpyridinium bromide, dodecyltrimethylammonium bromide, hexadecyltrimethylammonium bromide, tetradecyl-β-D-maltoside, octylglucoside, glycyrrhetinic acid, 3-(N,N-dimethylpalmitylammonio)propane-sulfonate, and sodium lauryl sulfate.

Cyclodextrins may also be used as suitable enhancers. Examples include β-cyclodextrin, hydroxypropyl-β-cyclodextrin, γ-cyclodextrin, and hydroxypropyl-γ-cyclodextrin.

A variety of other compounds may also be used as enhancers. Examples include sodium salicylate, ethylenediamine tetraacetic acid (EDTA), citric acid, chitosan & chitosan derivatives, N-trimethyl chitosan chloride, monocarboxymethyl-chitosan, palmitoyl carnitine chloride, acyl carnitines, ethylene glycol tetraacetic acid (EGTA), 3-alkylamido-2-alkoxypropyl-phosphocholine derivatives, alkanoylcholines, N-acetylated amino acids (based on α- and non-α-amino acids), mucoadhesive polymers, phospholipids, piperine, 1-methylpiperazine, α-amino acids, and mineral oil.

Thus a wide variety of enhancer compounds may be selected from the group consisting of fatty acids, fatty acid esters, fatty acid salts, glycerol, surfactants, cyclodextrins, sodium salicylate, ethylenediamine tetraacetic acid, citric acid, chitosan, chitosan derivatives, N-trimethyl chitosan chloride, monocarboxymethyl-chitosan, palmitoyl carnitine chloride, acyl carnitines, ethylene glycol tetraacetic acid, 3-alkylamido-2-alkoxypropyl-phosphocholine derivatives, alkanoylcholines, N-acetylated amino acids, mucoadhesive polymers, phospholipids, piperine, 1-methylpiperazine, α-amino acids, and mineral oil.

The permeability enhancer and the polar agent may be mixed in any proportion so long as there is provided a therapeutically effective amount of the polar agent and a permeability-enhancing amount of the enhancer compound. Enhancement in dermal bioavailability of topically administered polar agents can depend on the nature and concentration of the enhancer compound with which the agent is formulated. It is thus contemplated that the required therapeutic amount may be contained in a single dosage form or divided between one or more dosages intended for application at the same time or in sequence.

The permeability enhancers act relatively independently of the concentration of polar agent. Differing permeability enhancers can reach either optimal or maximum enhancement over a wide concentration range depending on their particular inherent enhancement potential. Often, enhancers have a non-linear dose response relationship between concentration of enhancer present and amount of increased polar agent absorption. The amount of enhancer to be utilized in an oral dosage form with a polar agent is initially based upon the enhancement properties observed in Caco-2 cell assays at varying fixed enhancer concentrations. Based upon those results, an effective in vivo amount of enhancer compound for a human formulation can be estimated, demonstrated and optimized without undue experimentation using methods well known to those skilled in the formulation art, to achieve a desired pharmacokinetic in vivo profile.

In formulating the composition of this invention, it will be apparent to those skilled in the formulation art that more effective enhancer compounds would require less polar agent than less effective permeability enhancers to achieve a target pharmacokinetic profile. Given those considerations and variations, the amount of enhancer may be at least about 0.1 wt % of the combined weight of enhancer and polar agent, more preferably at least about 50 wt %, and more preferably at least 70 wt % of the combined weight of enhancer and polar agent. The amount is preferably at most 95 wt %, more preferably at most 80 wt %, and more preferably at most 75 wt % of the combined weight of the enhancer and polar agent. Thus, as shown in the examples, a typical dosage form may contain a wide range of concentrations of enhancer compounds depending on the compound itself and its efficacy in enhancing the permeability of polar agents following oral administration. Concentrations as low as 0.001% by weight up to 20% have been demonstrated to be effective in enhancement of the permeability of polar agents.

In yet other embodiments, a dermatologically and/or ophthalmically acceptable base includes one or more antioxidants to enhance chemical stability where required. Suitable antioxidants include, by way of example only, butylated hydroxytoluene (BHT), sodium ascorbate, ascorbic acid, sodium metabisulfite, and tocopherol. In certain embodiments, antioxidants enhance chemical stability where required.

In addition to those enumerated above, any other surfactant, moisturizer, gelling agent, preservative, colorant or pigment, antioxidant, radical scavenger, emulsifier, humectant, pH modifier, chelating agent, or other dermatologically acceptable excipient commonly known to those of ordinary skill in the art as useful in topical compositions is contemplated as useful in the compositions described herein. Further, any non-toxic, inert, and effective topical carrier may be used to formulate the compositions described herein.

Well-known carriers used to formulate other topical therapeutic compositions for administration to humans will be useful in these compositions. Examples of such components that are well known to those of skill in the art are described in The Merck Index, Thirteenth Edition, Budavari et al., Eds., Merck & Co., Inc., Rahway, N.J. (2001); the CTFA (Cosmetic, Toiletry, and Fragrance Association) International Cosmetic Ingredient Dictionary and Handbook, Tenth Edition (2004); and the "Inactive Ingredient Guide", U.S. Food and Drug Administration (FDA) Center for Drug Evaluation and Research (CDER) Office of Management, the contents of which are hereby incorporated by reference in their entirety. Examples of such useful pharmaceutically acceptable excipients, carriers and diluents include distilled water, physiological saline, Ringer's solution, dextrose solution, Hank's solution, and DMSO, which are among those preferred for use herein.

These additional other inactive components, as well as effective formulations and administration procedures, are well known in the art and are described in standard textbooks, such as Goodman and Gillman's: The Pharmacological Bases of Therapeutics, 8th Ed., Gilman et al. Eds. Pergamon Press (1990) and Remington's Pharmaceutical Sciences, 17th Ed., Mack Publishing Co., Easton, Pa. (1990), both of which are incorporated by reference herein in their entirety.

The composition may be used immediately or stored for later use in any type of container known to one of skill in the art such as, for example, pouch, jar, bottle, tube, ampule and pre-filled syringe. Finally, the composition may be sterilized by any method known to one of skill in the art such as, for example, γ radiation.

The compounds and compositions described herein may be administered at prophylactically effective dosage levels to prevent the above-recited conditions and disorders, as well as to prevent other conditions and disorders characterized by insulin resistance or hyperglycemia.

The pharmaceutical compositions and compounds of embodiments herein can be administered in a wide range of dosage-forms including, for example, solid dosage forms and liquid dosage forms. Solid dosage forms may include powders, tablets, pills, capsules, suppositories, or dispersible granules. A solid carrier can be one or more substances that function as a diluting agent, flavor additive, solvent, lubricant, suspension agent, binder, preservative, tablet-disintegrating substance or encapsulating material. In powdered form, the carrier may be a finely pulverized solid including lactose, hydroxypropylmethylcellulose and PVP, mixed with an appropriate amount of the active ingredient. Appropriate carriers for powder and tablet forms include for example magnesium carbonate, magnesium stearate, talc, sugar, lactose, pectin, dextrin, stiffeners, gelatins, tragacanth, methylcellulose, and sodium carboxymethylcellulose.

Liquid dosage forms include for example solutions, suspensions, and emulsions. Also included are compositions in solid form that are meant to be converted to liquid form shortly prior to consumption. These forms may include, in addition to the active ingredients, artificial colors, flavors, stabilizers, buffers, natural or artificial sweeteners, dispersing agents, thickeners, dissolving agents and the like.

Solutions or mixtures may be administered directly to the nasal cavity using conventional means, such as drops or sprays. The composition may be produced in individual or multi-dose forms. Multi-dose forms would include a dropper, pipette or atomizer that delivers a predetermined volume of the composition.

The pharmaceutical compositions and compounds of embodiments herein may be provided in individual dosage units that contain a suitable amount of the active ingredient. The individual doses may be provided in a package, or as a kit that includes a measuring device, e.g., a device for measuring oral or injectable dosages (i.e., a measuring cup, needle, or syringe). The kit can also include, other materials such buffers, diluents, filters, and package inserts with instructions for use. A label may be present on the on the kit to indicate that the composition is used for a specific therapy, and may also indicate directions for use.

If desired, the compositions of the present invention may further comprise one or more additional active agents. Where it is appropriate, any of the active agents may be administered in the form of the compound per se, and/or in the form of a salt, polymorph, ester, amide, prodrug, derivative, or the like, provided the salt, polymorph, ester, amide, prodrug or derivative is suitable pharmacologically. Where it is appropriate, salts, esters, amides, prodrugs and other derivatives of the active agents may be prepared using standard procedures known to those skilled in the art of synthetic organic chemistry and described, for example, by J. March, Advanced Organic Chemistry: Reactions, Mechanisms and Structure, 4th Ed. (New York: Wiley-Interscience, 1992). For any active agents that may exist in enantiomeric forms, the active agent may be incorporated into the present compositions either as the racemate or in enantiomerically enriched form.

The dosage of the active compound(s) being administered will depend on the condition being treated, the particular compound, and other clinical factors such as age, sex, weight, and health of the subject being treated, the route of administration of the compound(s), and the type of composition being administered (tablet, gel cap, capsule, solution, suspension, inhaler, aerosol, elixir, lozenge, injection, patch, ointment, cream, etc.). It is to be understood that the present disclosure has application for both human and animal use. The amount of the compound, or an active salt or derivative thereof, required for use in treatment will be ultimately at the discretion of the attendant physician or clinician.

As described above, the compounds of the invention are useful for the prevention, treatment, control, amelioration, or reduction of risk of the diseases, disorders and conditions noted herein. The dosage of the compound as an active ingredient in the compositions of this invention may be varied so that a suitable dosage form is obtained. The active ingredient may be administered to patients (animals and human) in need of such treatment in dosages that will provide optimal pharmaceutical efficacy. The selected dosage depends upon the desired therapeutic effect, on the route of administration, and on the duration of the treatment. The dose will vary from patient to patient depending upon the nature and severity of disease, the patient's weight, special diets then being followed by a patient, concurrent medication, and other factors which those skilled in the art will recognize. Generally, dosage levels of between 0.001 to 100 mg/kg. of body weight daily are administered to the patient, e.g., humans and elderly humans. The therapeutically effective amount will generally be about 0.5 mg to 10 g per patient per day which may be administered in single or multiple doses. In some embodiments the therapeutically effective amount is between a lower limit of 0.5 mg, 10 mg, 1 mg, 500.0 mg, 1000 mg, 1500 mg, 2000 mg, 2500 mg, 3000 mg, 3500 mg, 4000 mg, 4500 mg, 5000 mg, 5500 mg, 6000 mg, 6500 mg, 7000 mg, 7500 mg, 8000 mg, 8500 mg, 9000 mg, 9500 mg, and 10000 mg; and an upper limit of 10000 mg, 9500 mg, 9000 mg, 8500 mg, 8000 mg, 7500 mg, 7000 mg, 6500 mg, 6000 mg, 5500 mg, 5000 mg, 4500 mg, 4000 mg, 3500 mg, 3000 mg, 2500 mg, 2000 mg, 1500 mg, 1000 mg, 500.0 mg, 100 mg, 10 mg and 0.5 mg. In some embodiments, the therapeutically effective amount will be about 0.5 mg to 2500 mg per patient per day; in some embodiments about 0.5 mg to 200 mg per patient per day; in some embodiments about 0.5 mg to 500 mg per patient per day; in some embodiments about 0.5 mg to 1000 mg per patient per day; and in yet some other embodiments about 5 mg to 50 mg per patient per day. Pharmaceutical compositions of the present invention may be provided in a solid dosage formulation such as comprising about 0.5 mg to 500 mg active ingredient, or comprising about 1 mg to 250 mg active ingredient. The pharmaceutical composition may be provided in a solid dosage formulation comprising for example about 1 mg, 5 mg, 10 mg, 25 mg, 50 mg, 100 mg, 200 mg, 250 mg, 500 mg or 1000 mg of active ingredient. For oral administration, the compositions may be provided in the form of tablets containing 1.0 to 1000 milligrams of the active ingredient, such as 1, 5, 10, 15, 20, 25, 50, 75, 100, 150, 200, 250, 300, 400, 500, 600, 750, 800, 900, 1000 and 2000 milligrams of the active ingredient for the symptomatic adjustment of the dosage to the patient to be treated. The compounds may be administered on a regimen of 1 to 4 times per day, such as once, twice, three times or four times per day.

Definitions

Molecular terms, when used in this application, have their common meaning unless otherwise specified.

The articles "a" and "an" as used herein mean "one or more" or "at least one," unless otherwise indicated. That is, reference to any element of the present invention by the indefinite article "a" or "an" does not exclude the possibility that more than one of the element is present.

As used herein, the term "alkyl" is intended to include both branched and straight-chain saturated aliphatic hydrocarbon groups having the specified number of carbon atoms. For example, "$C_1$-$C_{10}$ alkyl" or "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$-$C_6$ alkyl" or "$C_{1-6}$ alkyl" denotes alkyl having 1 to 6 carbon atoms. Alkyl group can be unsubstituted or substituted with at least one hydrogen being replaced by another chemical group. In some embodiments the one of more hydrogen atoms is replaced by a chemical group selected from hydroxyl, and dimethylamino. Examples of alkyl groups include, but are not limited to, methyl (Me), ethyl (Et), propyl (e.g., n-propyl and isopropyl), butyl (e.g., n-butyl, isobutyl, t-butyl), pentyl (e.g., n-pentyl, isopentyl, neopentyl). Examples of substituted alkyl includes, but is not limited to, —$CH_2N(CH_3)_2$, —$CH2CH_2N(CH_3)_2$, and —$CH_2CH_2CH_2N(CH_3)_2$.

"Alkenyl" is intended to include hydrocarbon chains of either straight or branched configuration having the specified number of carbon atoms and one or more, preferably one to three, carbon-carbon double bonds that may occur in any stable point along the chain. For example, "$C_2$-$C_6$ alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3-pentenyl, 4-pentenyl, 2-hexenyl, 3-hexenyl, 4-hexenyl, 5-hexenyl, 2-methyl-2-propenyl, and 4-methyl-3-pentenyl.

Alkynyl" is intended to include hydrocarbon chains of either straight or branched configuration having one or more, preferably one to three, carbon-carbon triple bonds that may occur in any stable point along the chain. For example, "$C_2$-$C_6$ alkynyl" is intended to include $C_2$, $C_3$, $C_4$, $C_5$, and $C_6$ alkynyl groups; such as ethynyl, propynyl, butynyl, pentynyl, and hexynyl.

The term "alkoxy" or "alkyloxy" refers to an —O-alkyl group. "$C_1$-$C_6$ alkoxy" or "$C_{1-6}$ alkoxy" (or alkyloxy), is intended to include $C_1$, $C_2$, $C_3$, $C_4$, $C_5$, and $C_6$, alkoxy groups. Examples of alkoxy groups include, but are not limited to, methoxy, ethoxy, propoxy (e.g., n-propoxy and isopropoxy), and t-butoxy.

"Aryl" groups refer to monocyclic or polycyclic aromatic hydrocarbons, including, for example, phenyl, and naphthyl. "$C_6$-$C_{10}$ aryl" or "$C_{6-10}$ aryl" refers to phenyl and naphthyl. Unless otherwise specified, "aryl", "$C_6$-$C_{10}$ aryl," "$C_{6-10}$ aryl," or "aromatic residue" may be unsubstituted or substituted with 1 to 5 groups selected from —OH, —$OCH_3$, —Cl, —F, —Br, —I, —CN, —$NO_2$, —$NH_2$, —$NH(CH_3)$, —$N(CH_3)_2$, —$CF_3$, —$OCF3$, —$C(O)CH_3$, —$SCH_3$, —$S(O)$ $CH_3$, —$S(O)_2CH_3$, —$CH_3$, —$CH_2CH_3$, —$CO_2H$, and —$CO_2CH_3$.

The term "benzyl," as used herein, refers to a methyl group on which one of the hydrogen atoms is replaced by a phenyl group, wherein said phenyl group may optionally be substituted by one to five, preferably one to three, substituents independently selected from methyl, trifluoromethyl (—$CF_3$), hydroxyl (—OH), methoxy (—$OCH_3$), halogen, cyano (—CN), nitro (—$NO_2$), —$CO_2Me$, —$CO_2Et$, and —$CO_2H$. Representative examples of benzyl group include, but are not limited to, $PhCH_2$—, 4-MeO—$C_6H_4CH_2$—, 2,4,6-tri-methyl-$C_6H_2CH_2$—, and 3,4-di-Cl—$C_6H_3CH_2$—.

A "compound," as used herein, refers to any type of substance or agent that is commonly considered a drug, or a candidate for use as a drug, as well as combinations and mixtures of the above. When referring to a compound of the invention, and unless otherwise specified, the term "compound" is intended to encompass not only the specified molecular entity but also its pharmaceutically acceptable, pharmacologically active analogs, including, but not limited to, salts, polymorphs, esters, amides, prodrugs, adducts, conjugates, active metabolites, and the like, where such modifications to the molecular entity are appropriate.

As used herein, a "derivative" of a compound refers to a chemical compound that may be produced from another compound of similar structure in one or more steps. Non-limiting examples include replacement of H by an alkyl, acyl, or amino group.

As used herein, an "effective amount" or "therapeutically effective amount" means an amount sufficient to produce a selected effect, such as alleviating symptoms of a disease or disorder. In the context of administering compounds in the form of a combination, such as multiple compounds, the amount of each compound, when administered in combination with another compound(s), may be different from when that compound is administered alone. Thus, an effective amount of a combination of compounds refers collectively to the combination as a whole, although the actual amounts of each compound may vary. The term "more effective" means that the selected effect is alleviated to a greater extent by one treatment relative to the second treatment to which it is being compared.

The terms "formula" and "structure" are used interchangeably herein.

The term "halo" or "halogen" refers to fluoro, chloro, bromo, and iodo. "Haloalkyl" is intended to include both branched and straight-chain saturated aliphatic hydrocarbon groups having the specified number of carbon atoms, substituted with one or more halogens. Examples of haloalkyl include, but are not limited to, fluoromethyl, difluoromethyl, trifluoromethyl, and trichloromethyl.

"Haloalkoxy" or "haloalkyloxy" represents a haloalkyl group as defined above with the indicated number of carbon atoms attached through an oxygen bridge. For example, "$C_1$-$C_6$ haloalkoxy" or "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, trichloromethoxy, and 2,2,2-trifluoroethoxy.

As used herein, the term "heteroaryl" is intended to mean stable monocyclic and polycyclic aromatic hydrocarbons that include at least one heteroatom ring member, such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Unless otherwise specified, heteroaryl groups may be unsubstituted or substituted with 1 to 5 groups selected from —OH, —$OCH_3$, —Cl, —F, —Br, —I, —CN, —NO₂, —NH₂, —NH(CH₃), —N(CH₃)₂, —CF₃, —OCF3, —C(O)CH₃, —SCH₃, —S(O)CH₃, —S(O)₂CH₃, —CH₃, —CH₂CH₃, —CO₂H, and —CO₂CH₃. The nitrogen atom is substituted or unsubstituted (i.e., N or NR wherein R is H or another substituent, if defined). The nitrogen and sulfur heteroatoms may optionally be oxidized (i.e., N→O and S(O)$_p$, wherein p is 0, 1 or 2).

The term "heterocyclyl," "heterocyclic" or "heterocyclyl ring" is defined as a saturated or partially unsaturated ring containing one to four hetero atoms or hetero groups selected from O, N, NH, —N(R$^Z$)—, —S(O)— or —S(O)₂—, wherein R$^Z$ is selected from alkyl, alkenyl, alkynyl, aryl, heteroaryl, cycloalkyl, optionally substituted heterocyclyl, in a single or fused heterocyclic ring system having from three to twelve ring members. In a preferred embodiment, a heterocyclyl is a ring system having three to seven ring members Examples of a heterocyclyl group include, without limitation, morpholinyl, piperidinyl, and pyrrolidinyl.

The term, "mitochondrial uncoupling", also referred to as "uncoupling", refers to the process whereby protons enter the mitochondrial matrix via a pathway independent of ATP synthase and thereby uncouple nutrient oxidation from ATP production. This process can be pharmacologically induced by small molecule mitochondrial protonophores, which directly shuttle protons across the mitochondrial inner membrane into the matrix. The primary pathway for energy production in aerobic cells involves the oxidation of nutrients (including fats, carbohydrates, and amino acids) in mitochondria, which promotes the efflux of protons out of the mitochondrial matrix. This process creates a pH and electrochemical gradient across the mitochondrial inner membrane. Protons normally re-enter the mitochondrial matrix via ATP synthase, which results in ATP production. Protons can also re-enter the mitochondrial matrix via pathways independent of ATP synthase, which 'uncouples' nutrient oxidation and proton efflux from ATP production.

The phrase "opthalmically acceptable" is employed herein to refer to those compounds, materials, compositions, and/or dosage forms that are, within the scope of sound medical judgment, suitable for use in contact with the eyes of human beings and animals without excessive toxicity, irritation, allergic response, and/or other problem or complication, commensurate with a reasonable benefit/risk ratio.

The term "perfluoroalkyl" refers to is an alkyl group in which all of the H substituents of an alkyl group have been replaced by F atoms.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 18$^{th}$ Edition, Mack Publishing Company, Easton, Pa., 1990, the disclosure of which is hereby incorporated by reference.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug, or may demonstrate increased palatability, or be easier to formulate.

The terms "subject," "individual" or "patient" are used interchangeably and as used herein are intended to include human and non-human animals. Non-human animals includes all vertebrates, e.g. mammals and non-mammals, such as non-human primates, sheep, dogs, cats, cows, horses, chickens, amphibians, and reptiles, although mammals are preferred, such as non-human primates, sheep, dogs, cats, cows and horses. Preferred subjects include human patients in need of enhancement of an immune response. The methods are particularly suitable for treating human patients having a disease or disorder described herein.

The terms "administration of" and or "administering a" compound should be understood to mean providing a compound described herein or a prodrug thereof to the individual in need of treatment.

The term "treating" or "treatment" as used herein refers to administration of a compound or agent to a subject who has a disorder or is at risk of developing the disorder with the purpose to cure, alleviate, relieve, remedy, delay the onset of, prevent, or ameliorate the disorder, the symptom of the disorder, the disease state secondary to the disorder, or the predisposition toward the disorder.

EXAMPLES

Processes for preparing compounds of the present invention, such as formulas I to V, or for preparing intermediates useful for preparing compounds of formulas I to V or other formulas of the present disclosure are provided as further embodiments of the invention or are known in the art. While the following text may exemplify specific compounds and corresponding routes of synthesis, it is not intended to limit the scope of the invention to such particular reference or examples. Various modifications may be made by those skilled in the art, in view of practical and economic considerations, such as the source of the agents and specific conditions of reactions.

Example 1

5-Chloro-2-hydroxy-3-methyl-N-(6-(trifluoromethyl)benzo[d]thiazol-2-yl)benzamide (1)

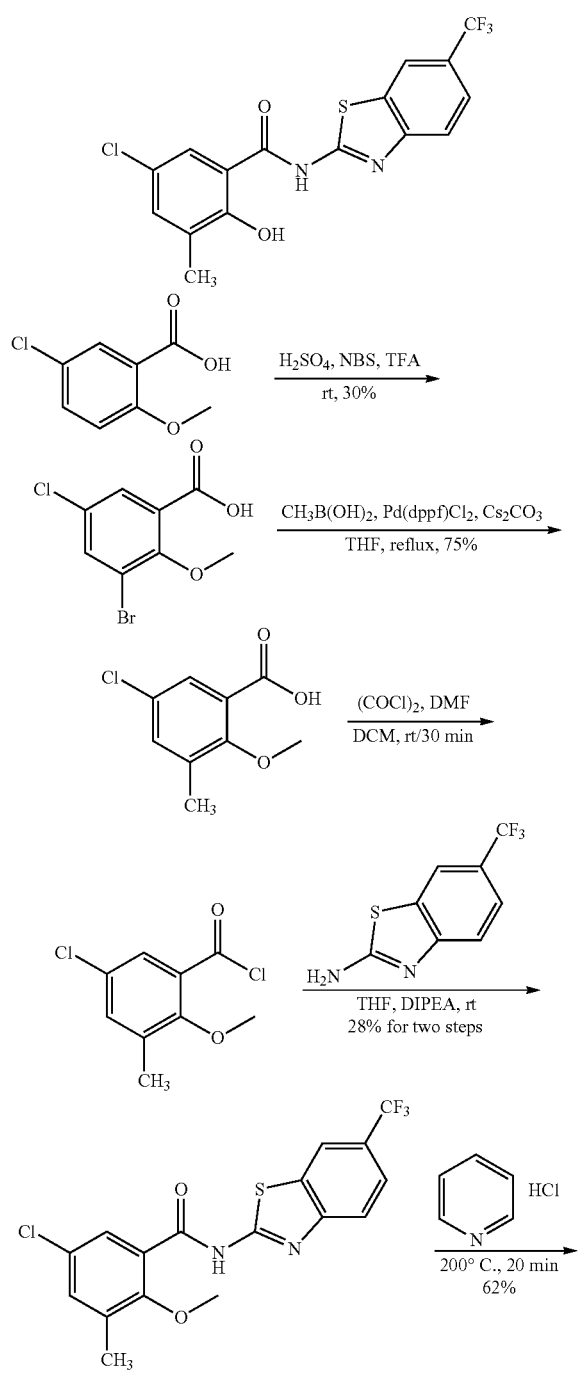

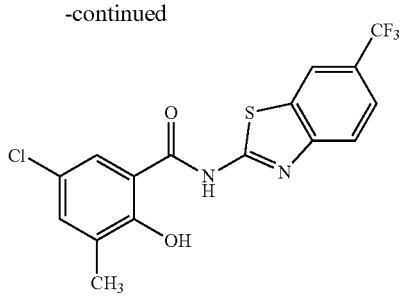

To a stirred solution of 5-Chloro-2-methoxybenzoic acid (1.86 g, 10 mmol) in sulfuric acid (3.4 ml) and trifluoroacetic acid (6.8 ml) at ambient temperature was added N-bromosuccinimide (1.96 g, 11 mmol). The pale solution was stirred at ambient temperature for 3 hs. The resulting pale suspension was carefully poured onto crushed ice. The mixture was extracted with ethyl acetate. The ethyl acetate layer dried over sodium sulfate and concentrated under reduced pressure. The light yellow residue was suspended in minimum amount of methylene chloride. The solid was collected, washed with cold methylene chloride and dried under vacuum to yield the 3-bromo-5-chloro-2-methoxybenzoic acid as a white solid (1.7 g, 64%). $^1$H NMR (300 MHz, acetone-$d_6$) δ 7.86 (d, 1H, J=3.0 Hz), 7.78 (d, 1H, J=3.0 Hz), 3.91 (s, 3H).

A mixture of 3-bromo-5-chloro-2-methoxybenzoic acid (430 mg, 1.62 mmol), methylboronic acid (291 mg, 4.86 mmol), Pd(dppf)Cl$_2$ (23 mg, 0.032 mmol) and cesium carbonate (1.58 g, 4.86 mmol) were refluxed in tetrahydrofuran (10 ml) under nitrogen overnight. The reaction was acidified the pH to 1 using 1N HCl and extracted with ethyl acetate. The ethyl acetate layer dried over Na$_2$SO$_4$ and concentrated under reduced pressure. The residue was purified via silica gel column chromatography to give 5-chloro-2-methoxy-3-methylbenzoic acid as a white solid (220 mg, 68%).

5-chloro-2-methoxy-3-methylbenzoic acid (220 mg, 1.1 mmol) was dissolved in dichloromethane (5.0 mL), followed by the addition of catalytic amount of dimethylformamide (3 drops) and oxalyl chloride (114 uL, 1.32 mmol) respectively. The reaction was allowed to stir at room temperature for 30 min and concentrated in vacuo. The residue was redissolved in tetrahydrofuran (8.0 mL), and Hunig's base (230 uL, 1.31 mmol) and 6-(trifluoromethyl)benzo[d]thiazol-2-amine (240 mg, 1.1 mmol) were added. The mixture was stirred at room temperature for 48 hours before silica gel was added to quench the reaction. Solvent was evaporated and the resulting residue was purified via silica gel column chromatography to yield 5-chloro-2-methoxy-3-methyl-N-(6-(trifluoromethyl)benzo[d]thiazol-2-yl)benzamide (120 mg, 28% yield). $^1$H NMR (300 MHz, acetone-$d_6$) δ 11.60 (s, 1H), 8.45 (s, 1H), 7.96 (d, J=8.5 Hz, 1H), 7.88-7.72 (m, 2H), 7.57 (d, J=2.8 Hz, 1H), 4.00 (s, 3H), 2.43 (s, 3H). MS (ESI) [M+H]$^+$ requires m/z 401.03, found m/z 400.75.

5-chloro-2-methoxy-3-methyl-N-(6-(trifluoromethyl) benzo[d]thiazol-2-yl)benzamide (55 mg, 0.137 mmol) was mixed with pyridinium chloride (1.0 g). The mixture was heated to 210° C., stirred for 15 minutes and cooled down to room temperature. The resulting solid was dissolved in water and extracted with ethyl acetate. The organic layer was concentrated in vacuo and the residue was purified via silica gel column chromatography to yield 5-chloro-2-hydroxy-3-methyl-N-(6-(trifluoromethyl)benzo[d]thiazol-2-yl)benzamide 1 as a yellow solid (33.0 mg, 62% yield). $^1$H NMR (300 MHz, acetone-$d_6$) δ 8.42 (s, 1H), 8.10 (d, J=8.5 Hz, 1H), 7.92-7.82 (m, 2H), 7.42 (d, J=2.8 Hz, 1H), 2.27 (s, 3H).
MS (ESI) [M+H]$^+$ requires m/z 387.02, found m/z 386.85.

Example 2

5-Chloro-3-(2-(dimethylamino)ethyl)-2-hydroxy-N-(6-(trifluoromethyl)benzo[d]thiazol-2-yl)benzamide (2)

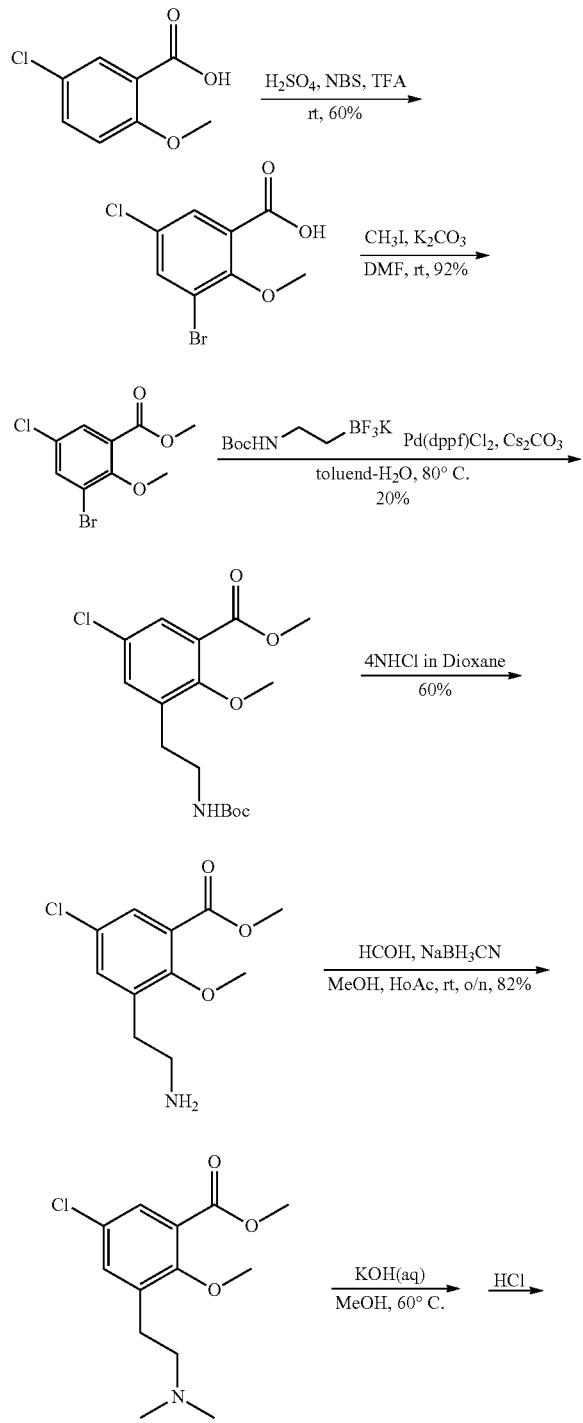

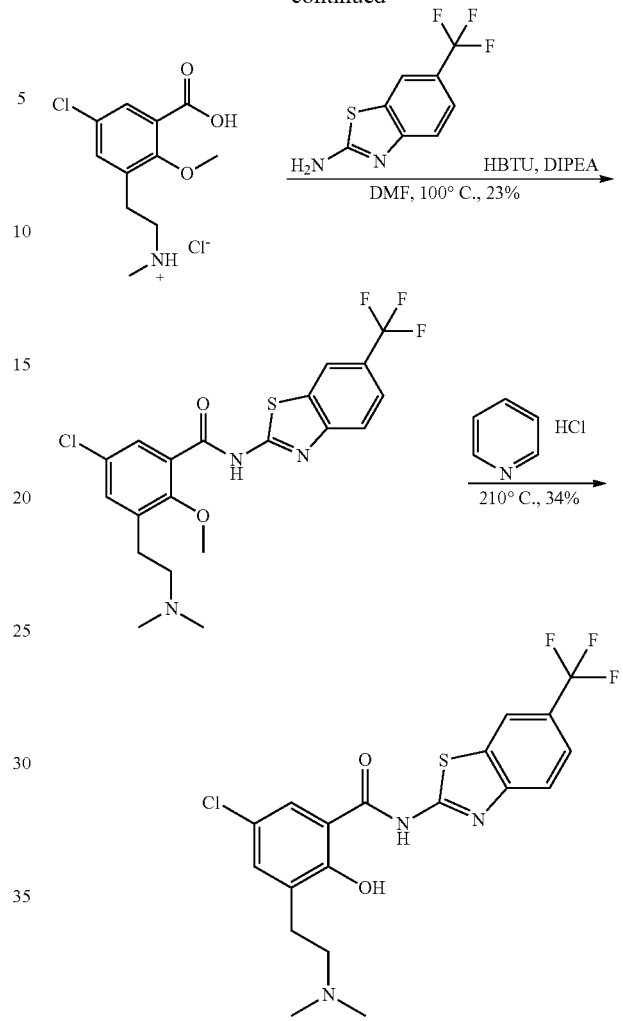

To a stirred solution of 5-chloro-2-methoxybenzoic acid (5.58 g, 30 mmol) in sulfuric acid (10 ml) and (20 ml) at room temperature was added N-bromosuccinimide (5.88 g, 33 mmol). The pale solution was stirred at room temperature for 3 hs. The resulting pale suspension was carefully poured onto 500 g crushed ice. The mixture was extracted with ethyl acetate. The ethyl acetate layer dried over sodium sulfate and concentrated under reduced pressure. The light yellow residue was suspended in minimum dichloromethane. The solid was collected, washed with cold dichloromethane and dried under vacuum overnight to yield 3-bromo-5-chloro-2-methoxybenzoic acid (7 g, 89%) as a white solid. $^1$H NMR (300 MHz, acetone-d$_6$) δ 7.86 (d, 1H, J=3.0 Hz), 7.78 (d, 1H, J=3.0 Hz), 3.91 (s, 3H).

To a stirred solution of 3-bromo-5-chloro-2-methoxybenzoic acid (6 g, 22.6 mmol) in dimethylformamide (30 ml) was added potassium carbonate (31 g, 226 mmol) and followed by CH$_3$I (1.4 ml, 22.6 mmol). The mixture was stirred at room temperature for 24 hs. Water was added and extracted with ethyl acetate for two times. The combined organic layer was washed with water and brine and dried over sodium sulfate. The organic layer was filtered and the solvent removed in vacuo to yield a pale yellow oil (6.18 g, 97%).

Methyl 3-bromo-5-chloro-2-methoxybenzoate (6.18 g, 22.07 mmol), potassium (2-((tert-butoxycarbonyl)amino)

ethyl)trifluoroborate (16.6 g, 66.21 mmol), Pd(dppf)Cl$_2$ (968 mg, 1.32 mmol) and caesium carbonate (21.5 g, 66.21 mmol) were added to a flask. This flask was evacuated and refilled with nitrogen three times. Subsequently, toluene (75 ml) and water (25 ml) were added to the flask under nitrogen. Then the mixture was stirred at 80° C. under nitrogen overnight. Saturated ammonium chloride solution was added and the resulting mixture was extracted with ethyl acetate for two times. The combined organic layer was concentrated in vacuo and the residue was purified via silica gel column chromatography to yield the title compound as a yellow oil (1.51 g, 20% yield). $^1$H NMR (300 MHz, Chloroform-d) δ 7.64 (d, J=2.7 Hz, 1H), 7.31 (d, J=2.7 Hz, 1H), 3.90 (s, 3H), 3.81 (s, 3H), 3.34 (brs, 2H), 2.82 (t, J=6.9 Hz, 2H), 1.41 (s, 9H). MS (ESI) [M+Na]$^+$ requires m/z 366.11, found m/z 365.95.

Methyl 3-(2-((tert-butoxycarbonyl)amino)ethyl)-5-chloro-2-methoxybenzoate (1.12 g, 3.26 mmol) was dissolved in 4N HCl in dioxane (5 ml) and the resulting mixture was stirred at room temperature for 2 hs. Saturated sodium bicarbonate solution was added and extracted with dichloromethane. The organic layer was washed with water and brine and dried over sodium sulfate. The organic layer was filtered and the solvent removed in vacuo to yield a pale yellow oil (475 mg, 60%). $^1$H NMR (500 MHz, Chloroform-d) δ 7.61 (d, J=2.7 Hz, 1H), 7.30 (d, J=2.7 Hz, 1H), 3.87 (s, 3H), 3.78 (s, 3H), 2.92 (t, J=7.5 Hz, 2H), 2.75 (t, J=7.1 Hz, 2H), 1.61 (s, 2H).

To a stirred solution of methyl 3-(2-aminoethyl)-5-chloro-2-methoxybenzoate (100 mg, 0.411 mmol) in methanol (3 ml) was added formaldehyde (122 ul, 1.64 mmol, 37% wt in water), sodium cyanoborohydride (103 mg, 1.64 mmol) and acetic acid (117 ul, 2.06 mmol). The resulting mixture was stirred at room temperature overnight. Saturated sodium bicarbonate was added and extracted with dichloromethane for two times. The combined organic layer was concentrated in vacuo and the residue was purified via silica gel column chromatography to yield the title compound as a yellow oil (88 mg, 82% yield). $^1$H NMR (300 MHz, Chloroform-d) δ 7.66 (d, J=2.5 Hz, 1H), 7.36 (d, J=2.6 Hz, 1H), 3.92 (s, 3H), 3.84 (s, 3H), 2.86 (t, J=7.5 Hz, 2H), 2.58 (t, J=7.5 Hz, 2H), 2.34 (s, 6H). MS (ESI) [M+H]$^+$ requires m/z 272.10, found m/z 272.05.

To a stirred solution of methyl 5-chloro-3-(2-(dimethylamino)ethyl)-2-methoxybenzoate (88 mg, 0.324 mmol) in methanol (5 ml) was added 1N potassium hydroxide (91 mg, 1.62 mmol, 1.62 ml) solution. The mixture was heated at 60° C. overnight. 1N HCl was added to adjust the PH to 1. The mixture was concentrated in vacuo. The residue was dissolved in dimethylformamide (3 ml). N,N,N',N'-Tetramethyl-O-(1H-benzotriazol-1-yl)uronium hexafluorophosphate (71 mg, 0.324 mmol) was added followed by N,N-diisopropylethylamine (282 ul, 1.62 mmol). The resulting mixture was stirred at room temperature for 15 mins, then 6-(trifluoromethyl)benzo[d]thiazol-2-amine (71 mg, 0.324 mmol) was added. The resulting mixture was stirred at 100° C. overnight. Saturated ammonium chloride solution was added and extracted with ethyl acetate for two times. The combined ethyl acetate layer was dried over Na$_2$SO$_4$ and concentrated under reduced pressure. The residue was purified via silica gel column chromatography to give title compound as a yellow powder (34 mg, 23%). $^1$H NMR (300 MHz, Chloroform-d) δ 8.16 (s, 1H), 8.05 (d, J=2.7 Hz, 1H), 7.91 (d, J=8.6 Hz, 1H), 7.71 (dd, J=8.5, 2.0 Hz, 1H), 7.50 (d, J=2.7 Hz, 1H), 3.97 (s, 3H), 2.99-2.93 (m, 2H), 2.75-2.66 (m, 2H), 2.43 (s, 6H). MS (ESI) [M+H]$^+$ requires m/z 458.08, found m/z 458.15.

5-Chloro-3-(2-(dimethylamino)ethyl)-2-methoxy-N-(6-(trifluoromethyl)benzo[d]thiazol-2-yl)benzamide (34 mg, 0.074 mmol) was mixed with pyridinium chloride (1.0 g). The mixture was heated to 210° C., stirred for 15 minutes and cooled down to room temperature. The resulting solid was dissolved in water and extracted with ethyl acetate. The organic layer was concentrated in vacuo and the residue was purified via silica gel column chromatography to 5-chloro-3-(2-(dimethylamino)ethyl)-2-hydroxy-N-(6-(trifluoromethyl) benzo[d]thiazol-2-yl)benzamide 2 as a yellow powder (10.0 mg, 34% yield). $^1$H NMR (400 MHz, CDCl$_3$) δ 8.11-7.98 (m, 2H), 7.85 (d, J=9.3 Hz, 1H), 7.66 (d, J=8.2 Hz, 1H), 7.17 (s, 1H), 3.06 (m, 2H), 3.01 (m, 2H), 2.79 (s, 6H). LRMS (ESI) [M+Na]$^+$ requires m/z 466.06, found m/z 465.75.

Example 3

5-Chloro-2-hydroxy-3-(2-(methylsulfonamido)ethyl)-N-(6-(trifluoromethyl)benzo[d]thiazol-2-yl)benzamide (3)

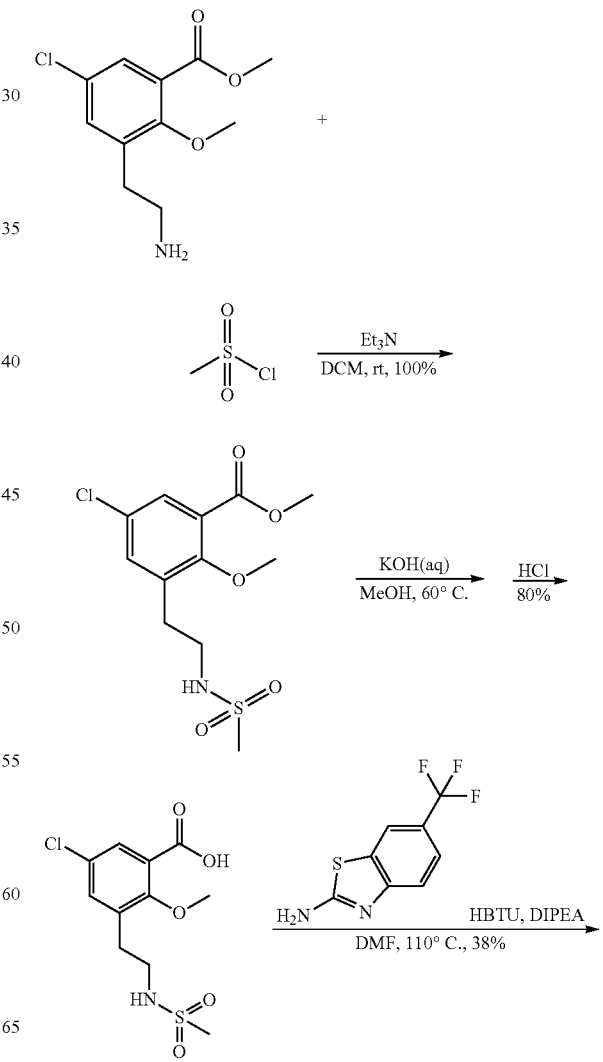

-continued

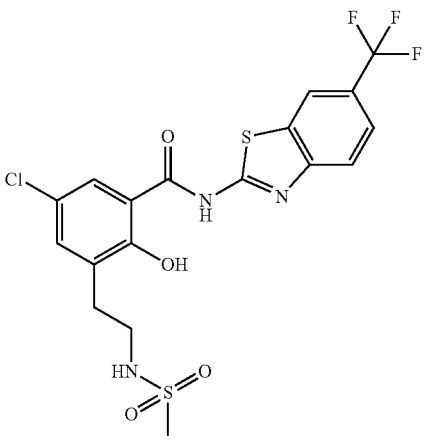

To a stirred solution of methyl 3-(2-aminoethyl)-5-chloro-2-methoxybenzoate (94 mg, 0.387 mmol) in dichloromethane (3 ml) was added trimethylamine (6 ul, 0.426 mmol) and methanesulfonyl chloride (33 ul, 0.426 mmol). The resulting mixture was stirred at room temperature for 2 hs. The mixture was diluted with dichloromethane and washed subsequently with 1N HCl, water and brine. The organic layer was dried over $Na_2SO_4$ and concentrated under reduced pressure to give a yellow oil (124 mg, 100%) which was used in the next step without further purification.

To a stirred solution of methyl 5-chloro-2-methoxy-3-(2-(methylsulfonamido)ethyl)benzoate (124 mg, 0.387 mmol) in methanol (5 ml) was added 1N potassium hydroxide (2.02 ml) solution. The resulting mixture was stirred at 50° C. overnight. 1N HCl was added to adjust the PH to 1. The mixture was extracted with ethyl acetate for two times. The combined organic layer was dried over sodium sulfate, concentrated in vacuo to afford a yellow oil (101 mg, 80%) which was used in the next step without further purification. MS (ESI) [M+Na]$^+$ requires m/z 330.02, found m/z 329.85.

5-Chloro-2-methoxy-3-(2-(methylsulfonamido)ethyl)benzoic acid (101 mg, 0.329 mmol) was dissolved in dimethylformamide (3 ml). N,N,N',N'-Tetramethyl-O-(1H-benzotriazol-1-yl)uronium hexafluorophosphate (149 mg, 0.394 mmol) was added followed by N,N-diisopropylethylamine (172 ul, 0.98 mmol). The resulting mixture was stirred at room temperature for 15 mins, then 6-(trifluoromethyl)benzo[d]thiazol-2-amine (86 mg, 0.394 mmol) was added. The resulting mixture was stirred at 110° C. overnight. Saturated ammonium chloride solution was added and extracted with ethyl acetate for two times. The combined ethyl acetate layer was dried over $Na_2SO_4$ and concentrated under reduced pressure. The residue was purified via silica gel column chromatography to give 5-Chloro-2-hydroxy-3-(2-(methylsulfonamido)ethyl)-N-(6-(trifluoromethyl)benzo[d]thiazol-2-yl)benzamide 3 as a yellow powder (55 mg, 38%). $^1$H NMR (300 MHz, acetone-$d_6$) δ 8.43 (s, 1H), 8.13 (d, J=2.6 Hz, 1H), 7.93 (d, J=8.2 Hz, 1H), 7.84 (d, J=6.9 Hz, 1H), 7.49 (d, J=2.6 Hz, 1H), 3.46 (t, J=7.0 Hz, 2H), 2.99 (t, J=7.0 Hz, 2H), 2.91 (s, 3H). MS (ESI) [M+Na]$^+$ requires m/z 516.00, found m/z 515.75.

Example 4

4-Chloro-2-((6-(trifluoromethyl)benzo[d]thiazol-2-yl)carbamoyl)phenyl morpholine-4-carboxylate (4)

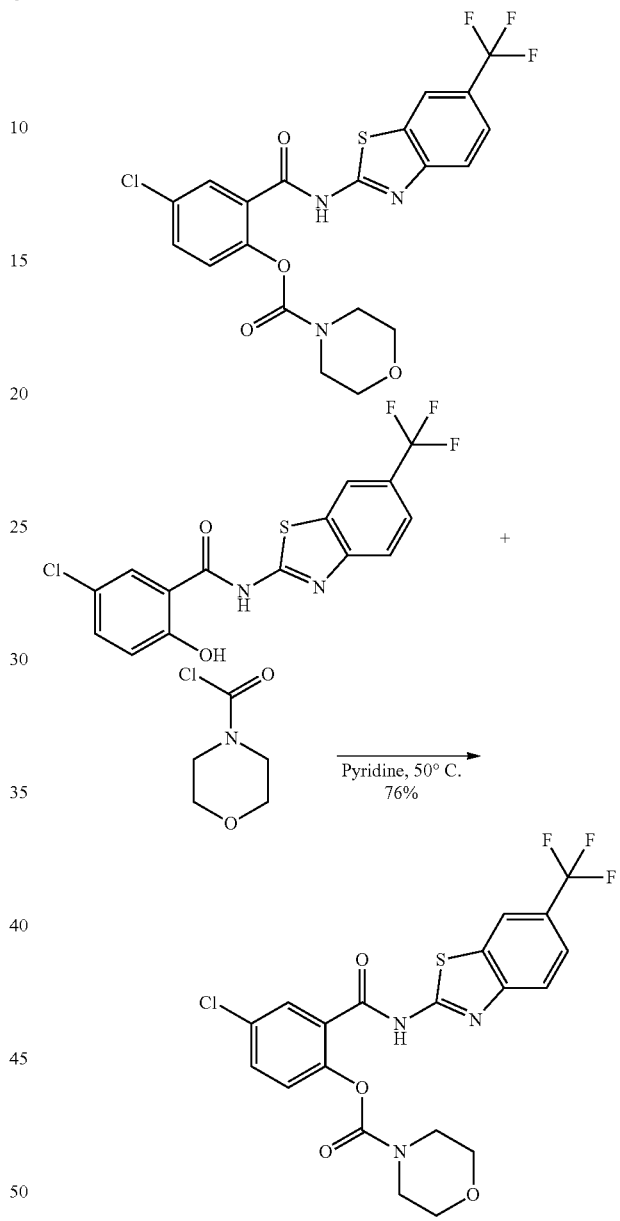

To a stirred solution of 5-chloro-2-hydroxy-N-(6-(trifluoromethyl)benzo[d]thiazol-2-yl)benzamide (37 mg, 0.1 mmol) in pyridine (3.0 mL) was added morpholine-4-carbonyl chloride (24 μL, 0.2 mmol). The reaction was heated to 50° C. for 7 h. After cooled down, 3N HCl was added. The mixture was extracted with ethyl acetate for two times. The organic layer was dried over sodium sulfate, concentrated in vacuo and the residue was purified via silica gel column chromatography to yield 4-chloro-2-((6-(trifluoromethyl)benzo[d]thiazol-2-yl)carbamoyl)phenyl morpholine-4-carboxylate 4 as a white solid (35.0 mg, 76% yield). $^1$H NMR (400 MHz, acetone-$d_6$) δ 8.45-8.41 (m, 1H), 7.89 (d, J=2.6 Hz, 1H), 7.86 (d, J=8.5 Hz, 1H), 7.71 (dd, J=8.5, 1.5 Hz, 1H), 7.64 (dd, J=8.7, 2.6 Hz, 1H), 7.37 (d, J=8.7 Hz, 1H), 3.75 (s, 4H), 3.63 (s, 2H), 3.45 (s, 2H). MS (ESI) exact mass calculated for [M+H]$^+$ requires m/z 485.0, found m/z 484.8.

Example 5

4-Chloro-2-((5-(trifluoromethyl)pyrazin-2-yl)carbamoyl)phenyl morpholine-4-carboxylate (5)

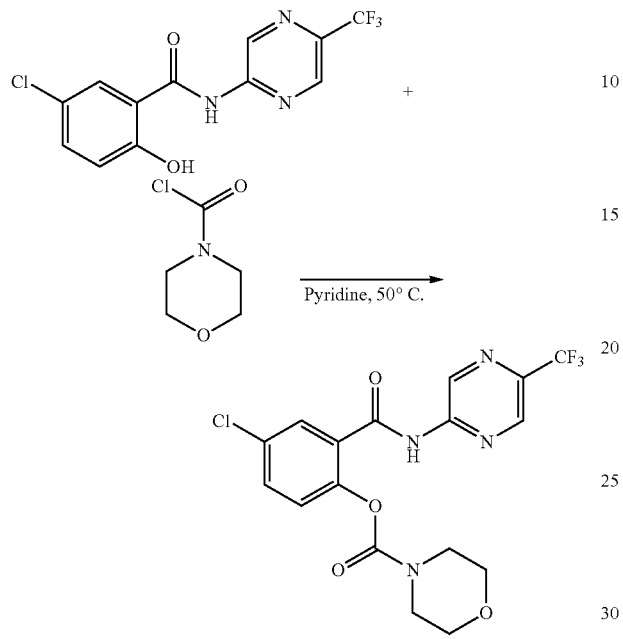

To a stirred solution of 5-chloro-2-hydroxy-N-(5-(trifluoromethyl)pyrazin-2-yl)benzamide (29 mg, 0.092 mmol) in pyridine (3.0 mL) was added morpholine-4-carbonyl chloride (22 μL, 0.184 mmol). The reaction was heated to 50° C. for 7 h. After cooled down, 3N HCl was added. The mixture was extracted with ethyl acetate for two times. The organic layer was dried over sodium sulfate, concentrated in vacuo and the residue was purified via silica gel column chromatography to yield 4-chloro-2-((5-(trifluoromethyl)pyrazin-2-yl)carbamoyl)phenyl morpholine-4-carboxylate 5 as a white solid (20.0 mg, 52% yield). $^1$H NMR (400 MHz, acetone-d$_6$) δ 10.44 (s, 1H), 9.65 (d, J=1.2 Hz, 1H), 8.87 (dd, J=1.3, 0.6 Hz, 1H), 7.89 (d, J=2.6 Hz, 1H), 7.65 (dd, J=8.7, 2.7 Hz, 1H), 7.38 (d, J=8.8 Hz, 1H), 3.82-3.49 (m, 6H), 3.41 (s, 2H). MS (ESI) [M+Na]$^+$ requires m/z 453.06, found m/z 453.15.

Example 6

4-Chloro-2-((6-(trifluoromethyl)benzo[d]thiazol-2-yl)carbamoyl)phenyl 4-methylpiperazine-1-carboxylate (6)

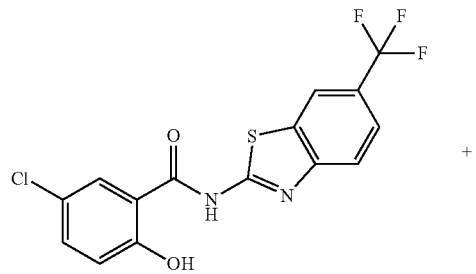

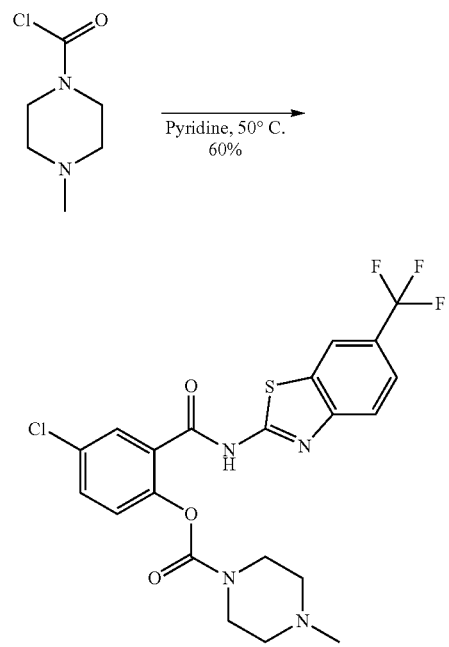

To a stirred solution of 5-chloro-2-hydroxy-N-(6-(trifluoromethyl)benzo[d]thiazol-2-yl)benzamide (37 mg, 0.1 mmol) in pyridine (3.0 mL) was added 4-methylpiperazine-1-carbonyl chloride (28 μL, 0.2 mmol). The reaction was heated to 50° C. for 7 h. After cooled down, 3N HCl was added. The mixture was extracted with ethyl acetate for two times. The organic layer was dried over sodium sulfate, concentrated in vacuo and the residue was purified via silica gel column chromatography to yield 4-chloro-2-((6-(trifluoromethyl)benzo[d]thiazol-2-yl)carbamoyl)phenyl 4-methylpiperazine-1-carboxylate 6 as a yellow solid (26.0 mg, 60% yield). $^1$H NMR (400 MHz, Chloroform-d) δ 8.03 (s, 1H), 7.64 (d, J=2.6 Hz, 1H), 7.55-7.46 (m, 2H), 7.38 (dd, J=8.7, 2.6 Hz, 1H), 7.15 (d, J=8.7 Hz, 1H), 3.84 (brs, 2H), 3.67 (brs, 2H), 2.67 (brs, 2H), 2.53 (brs, 2H), 2.39 (s, 3H). MS (ESI) [M+H]$^+$ requires m/z 499.08, found m/z 498.85.

Example 7

6-Chloro-3-(6-(trifluoromethyl)benzo[d]thiazol-2-yl)-2H-benzo[e][1,3]oxazine-2,4(3H)-dione (7)

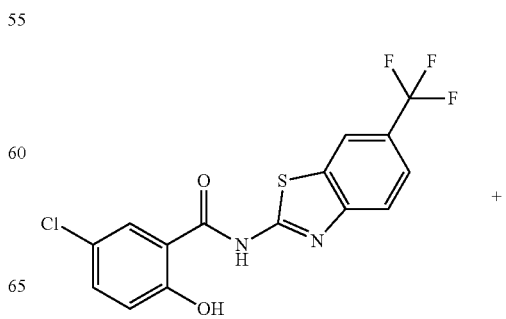

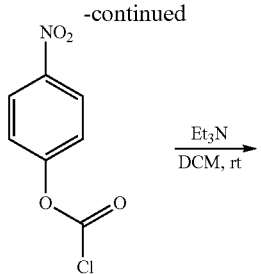

To a stirred solution of 5-chloro-2-hydroxy-N-(6-(trifluoromethyl)benzo[d]thiazol-2-yl)benzamide (55 mg, 0.15 mmol) in dichloromethane (3 ml) was added trimethylamine (62 ul, 0.44 mmol) and then 4-Nitrophenyl Chloroformate (44 mg, 0.22 mmol). The resulting yellow clear solution was stirred at room temperature overnight. Saturated NH$_4$Cl solution was added and extracted with ethyl acetate for two times. The combined ethyl acetate layer was dried over Na$_2$SO$_4$ and concentrated under reduced pressure. The residue was purified via silica gel column chromatography to give 6-chloro-3-(6-(trifluoromethyl)benzo[d]thiazol-2-yl)-2H-benzo[e][1,3]oxazine-2,4(3H)-dione 7 as a white solid (10 mg, 20%). $^1$H NMR (400 MHz, CDCl3) δ 8.28-8.19 (m, 2H), 8.11 (d, J=2.5 Hz, 1H), 7.84-7.78 (m, 1H), 7.76 (dd, J=8.8, 2.6 Hz, 1H), 7.37 (d, J=8.8 Hz, 1H). MS (ESI) [M+H]$^+$ requires m/z 398.98, found m/z 398.75.

Example 8

5-Chloro-2-(trifluoromethyl)-N-(6-(trifluoromethyl)benzo[d]thiazol-2-yl)-1H-benzo[d]imidazole-7-carboxamide (8)

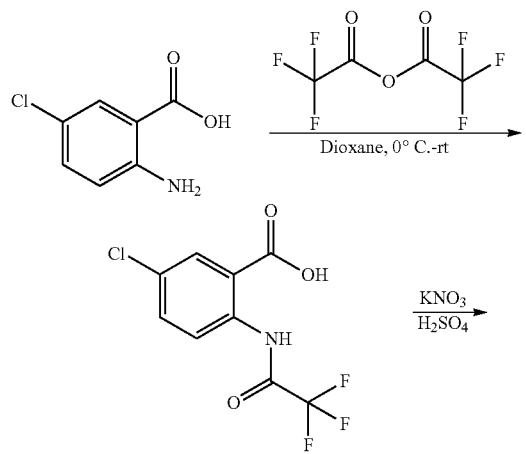

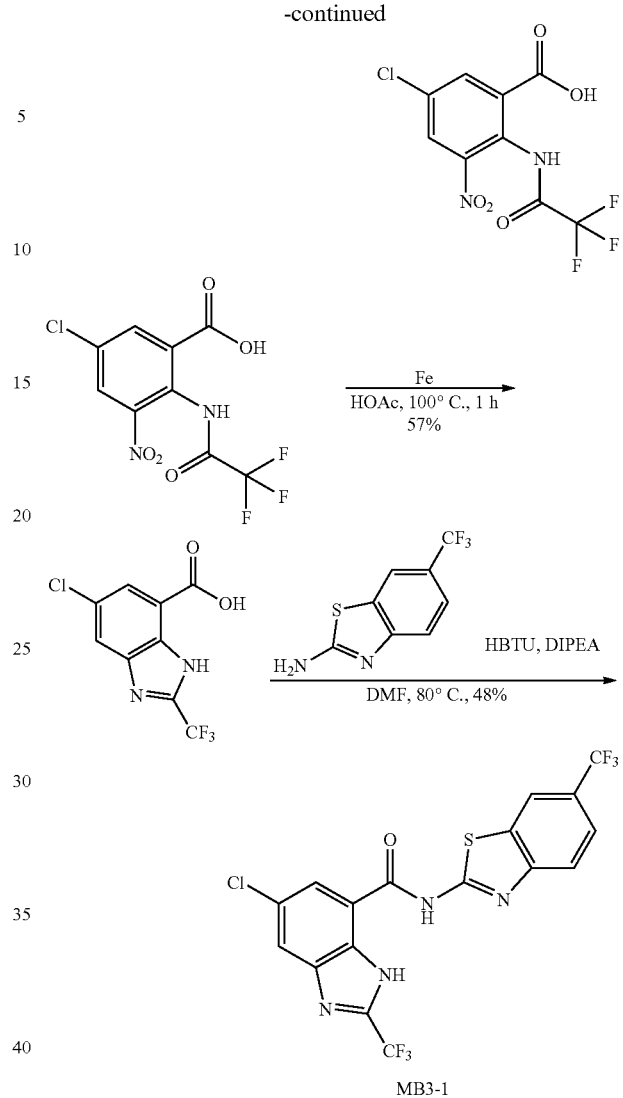

To a stirred solution of 2-amino-5-chlorobenzoic acid (5.13 g, 30 mmol) in dioxane (20 ml) at 0° C. was added trifluoroacetic anhydride (6 ml, 43 mmol) and the resulting mixture was stirred at room temperature overnight. After the reaction was completed, the mixture was separated between ethyl acetate and water. The organic layer was washed with brine, dried over Na$_2$SO$_4$ and concentrated in vacuo to afford 5-chloro-2-(2,2,2-trifluoroacetamido)benzoic acid (8.0 g, 100%) as a pale yellow solid which used in the next step without further purification.

To a stirred solution of 5-chloro-2-(2,2,2-trifluoroacetamido)benzoic acid (8.0 g, 30 mmol) in concentrated sulfuric acid (30 ml) at 0° C. was added potassium nitrate (12.1 g, 120 mmol) and the resulting mixture was stirred at room temperature overnight. After the reaction was completed, the mixture was poured into ice and the resulting solid was filtered. The filter cake was washed with water to afford 5-chloro-3-nitro-2-(2,2,2-trifluoroacetamido)benzoic acid (8.4 g, 90%) as a yellow solid which used in the next step without further purification.

To a stirred solution of 5-chloro-3-nitro-2-(2,2,2-trifluoroacetamido)benzoic acid (624 mg, 2 mmol) in acetic acid (10 ml) was added iron powder (560 mg, 10 mmol) and the reaction mixture was stirred at 100° C. for 1 h. After cooled to room temperature, the reaction was filtered and washed with water and ethyl acetate. The filtrate was concentrated in vacuo and purification by column chromatography gave the 5-chloro-2-(trifluoromethyl)-1H-benzo[d]imidazole-7-carboxylic acid as a pale yellow solid (300 mg, 57%). $^1$H NMR (400 MHz, acetone-d$_6$) δ 8.12 (d, J=1.9 Hz, 1H), 8.02 (d, J=1.9 Hz, 1H).

To a stirred solution of 5-chloro-2-(trifluoromethyl)-1H-benzo[d]imidazole-7-carboxylic acid (60 mg, 0.23 mmol) was added N,N,N',N'-Tetramethyl-O-(1H-benzotriazol-1-yl) uronium hexafluorophosphate (121 mg, 0.32 mmol) and N,N-diisopropylethylamine (278 ul, 1.6 mmol). The mixture was stirred for 10 mins and then 6-(trifluoromethyl)benzo[d]thiazol-2-amine (54 mg, 0.25 mmol) was added. The resulting reaction was heated at 80° C. for 2 hs. After cooled to room temperature, the mixture was separated between ethyl acetate and saturated ammonium chloride solution. The organic layer was washed with brine, dried over Na$_2$SO$_4$ and concentrated in vacuo. Purification by column chromatography gave 5-chloro-2-(trifluoromethyl)-N-(6-(trifluoromethyl)benzo[d]thiazol-2-yl)-1H-benzo[d]imidazole-7-carboxamide 8 as a pale yellow solid (40 mg, 38%). $^1$H NMR (500 MHz, acetone-d$_6$) δ 7.95 (s, 1H), 7.74 (s, 1H), 7.60 (s, 1H), 7.50 (d, J=8.3 Hz, 1H), 7.42 (s, 0.5H), 7.30 (d, J=8.3 Hz, 1H), 6.97 (s, 0.5H). MS (ESI) exact mass calculated for [M+H]$^+$ requires m/z 465.0, found m/z 464.7.

Example 9

2,4-Bis(trifluoromethyl)-5-((6-(trifluoromethyl)benzo[d]thiazol-2-yl)amino)phenol (9)

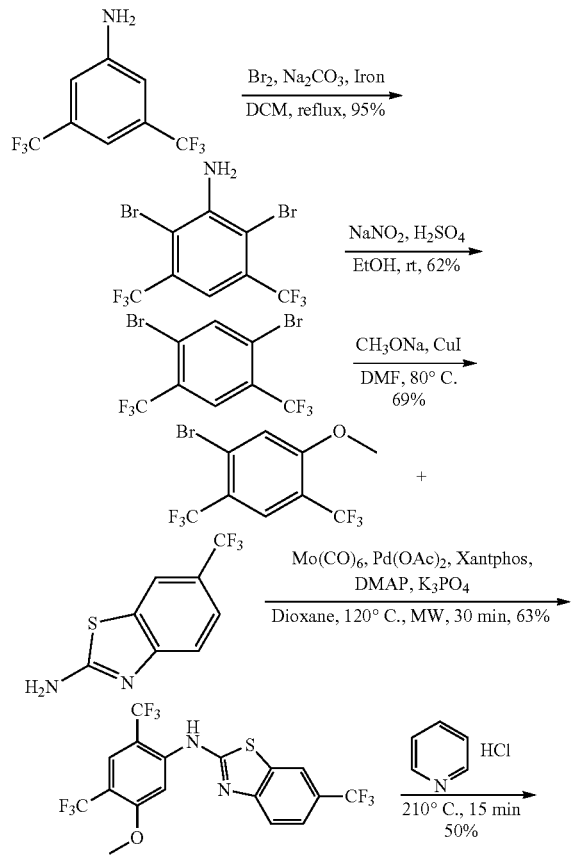

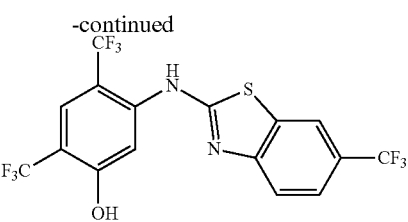

Bromine (5.61 ml, 109 mmol) in dichloromethane (50 ml) was added dropwise to a stirred solution of 3,5-bis(trifluoromethyl)aniline (8.34 g, 36.4 mmol), sodium carbonate (4.63 g, 43.7 mmol) and iron powder (100 mg, 1.8 mmol) in dichloromethane (50 ml). The mixture was refluxed 3 ds. After cooling, the mixture was filtered and the filtrate was partitioned between water and dichloromethane. The organic layer was washed with brine, dried over Na$_2$SO$_4$ and concentrated in vacuo to afford the title compound as a pale yellow solid (13.38 g, 95%) which is used for the next step without further purification. $^1$H NMR (400 MHz, Chloroform-d) δ 7.35 (s, 1H), 5.24 (broad singlet, 2H).

Sulfuric acid (4.35 ml) was added to a solution of 2,6-dibromo-3,5-bis(trifluoromethyl)aniline (1.16 g, 3 mmol) in ethanol (95%, 9 ml) followed by the addition of sodium nitrite (414 mg, 6 mmol) in water (1 ml). The reaction mixture was stirred for 2 h at 0° C. The mixture was diluted with water and extracted with ether. The organic layer was dried over sodium sulfate, concentrated in vacuo. Purification by column chromatography gave the title compound as a white solid (692 mg, 62%). $^1$H NMR (400 MHz, Chloroform-d) δ 8.11 (s, 1H), 7.95 (s, 1H).

To a stirred solution of 1,5-dibromo-2,4-bis(trifluoromethyl)benzene (330 mg, 0.89 mmol) in dimethylformamide (5 ml) was added copper(I) iodide (17 mg, 0.089 mmol) and 0.5N sodium methoxide in methanol (1.76 ml). The reaction mixture was stirred at 80° C. under N$_2$ for 6 hs. The mixture was diluted with water and extracted with ether. The organic layer was dried over sodium sulfate, concentrated in vacuo. Purification by column chromatography gave the title compound as a colorless oil (198 mg, 69%). $^1$H NMR (400 MHz, Chloroform-d) δ 7.85 (s, 1H), 7.33 (s, 1H), 3.98 (s, 3H). MS (ESI) exact mass calculated for [M]$^+$ requires m/z 321.95, found m/z 321.85.

A mixture of 1-bromo-5-methoxy-2,4-bis(trifluoromethyl)benzene (45 mg, 0.14 mmol), Mo(CO)$_6$ (111 mg, 0.42 mmol), 6-(trifluoromethyl)benzo[d]thiazol-2-amine (92 mg, 0.42 mmol), K$_3$PO$_4$ (149 mg, 0.70 mmol), 4-dimethylaminopyridine (34 mg, 0.28 mmol), palladium(II) acetate (4 mg, 0.014 mmol) and Xantphos (16 mg, 0.028 mmol) in dioxane (3 ml) was microwaved at 120° C. under nitrogen for 30 mins. Saturated ammonium chloride solution was added and extracted with ethyl acetate for two times. The combined organic layer was dried over sodium sulfate, concentrated in vacuo. Purification by column chromatography gave the title compound as a white solid (42 mg, 63%). $^1$H NMR (400 MHz, Chloroform-d) δ 8.37 (s, 1H), 8.02-7.96 (m, 1H), 7.83 (s, 1H), 7.78 (d, J=8.5 Hz, 1H), 7.70-7.63 (m, 1H), 4.05 (s, 3H).

N-(5-methoxy-2,4-bis(trifluoromethyl)phenyl)-6-(trifluoromethyl)benzo[d]thiazol-2-amine (43 mg, 0.088 mmol) was mixed with pyridinium chloride (1.0 g). The mixture was heated to 210° C., stirred for 15 minutes and cooled down to room temperature. The resulting solid was dissolved in water and extracted with ethyl acetate. The organic layer was concentrated in vacuo and the residue was purified via silica gel column chromatography to yield 2,4-bis(trifluoromethyl)-5-((6-(trifluoromethyl)benzo[d]thiazol-2-yl) amino)phenol 9 as a pale yellow powder (20.0 mg, 34% yield). ¹H NMR (400 MHz, acetone-$d_6$) δ 8.17 (s, 1H), 8.12 (s, 1H), 7.85 (s, 1H), 7.69 (s, 2H). MS (ESI) exact mass calculated for [M+H]⁺ requires m/z 447.01, found m/z 446.70.

Example 10

5-Hydroxy-2,4-bis(trifluoromethyl)-N-(6-(trifluoromethyl)benzo[d]thiazol-2-yl)benzamide (10)

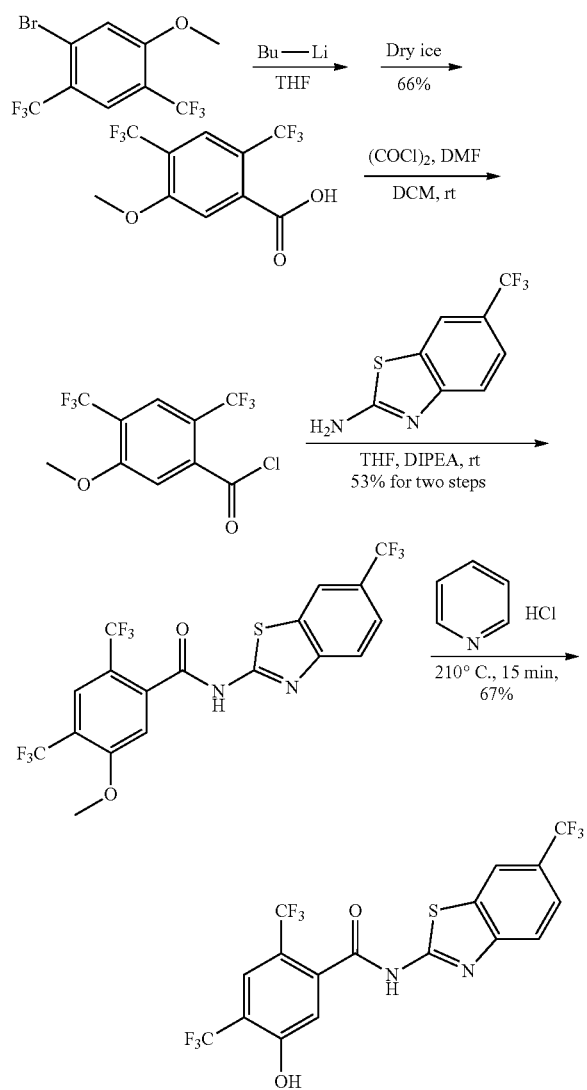

A solution of n-butyllithium (1.27 ml, 2.5M in hexane) was added dropwise to a previously formed solution of 1-bromo-5-methoxy-2,4-bis(trifluoromethyl)benzene (940 mg, 3 mmol) in tetrahydrofuran (10 ml). After 30 min of stirring at −78° C., 200 mg of carbonic dry ice was introduced in the reaction. After the mixture warm up to room temperature, the salt was extracted with a 2M sodium hydroxide solution 3 times. This solution was further acidified the pH to 1 with 2M HCl. The resulting white precipitate was recovered by filtration, dried under vacuum. The residue was purified via silica gel column chromatography to yield the title compound as a white powder (550.0 mg, 66% yield). ¹H NMR (400 MHz, acetone-$d_6$) δ 7.98 (s, 1H), 7.66 (s, 1H), 4.14 (s, 3H).

5-methoxy-2,4-bis(trifluoromethyl)benzoic acid (400 mg, 1.39 mmol) was dissolved in dichloromethane (5.0 mL), followed by the addition of catalytic amount of dimethylformamide (3 drops) and oxalyl chloride (143 uL, 1.67 mmol) respectively. The reaction was allowed to stir at room temperature for 30 min and concentrated in vacuo. The residue was re-dissolved in tetrahydrofuran (8.0 mL), and Hunig's base (291 uL, 1.67 mmol) and 6-(trifluoromethyl)benzo[d]thiazol-2-amine (244 mg, 1.12 mmol) were added. The mixture was stirred at room temperature for 48 hours before silica gel was added to quench the reaction. Solvent was evaporated and the resulting residue was purified via silica gel column chromatography to yield the title compound as a white solid (290 mg, 53% yield). ¹H NMR (500 MHz, acetone-$d_6$) δ 8.48 (s, 1H), 8.05 (s, 1H), 7.98-7.91 (m, 2H), 7.79 (dd, J=8.5, 1.4 Hz, 1H), 4.16 (s, 3H). MS (ESI) exact mass calculated for [M+H]⁺ requires m/z 489.03, found m/z 488.60.

5-methoxy-2,4-bis(trifluoromethyl)-N-(6-(trifluoromethyl)benzo[d]thiazol-2-yl)benzamide (100 mg, 0.205 mmol) was mixed with pyridinium chloride (1.8 g). The mixture was heated to 210° C., stirred for 15 minutes and cooled down to room temperature. The resulting solid was dissolved in water and extracted with ethyl acetate. The organic layer was concentrated in vacuo and the residue was purified via silica gel column chromatography to yield 5-hydroxy-2,4-bis(trifluoromethyl)-N-(6-(trifluoromethyl)benzo[d]thiazol-2-yl)benzamide 10 as a white powder (65.0 mg, 67% yield). ¹H NMR (500 MHz, acetone-$d_6$) δ 8.47 (s, 1H), 8.01 (s, 1H), 7.92 (d, J=8.5 Hz, 1H), 7.78 (dd, J=8.2, 0.9 Hz, 1H), 7.57 (s, 1H). MS (ESI) exact mass calculated for [M+H]⁺ requires m/z 475.02, found m/z 474.70.

Example 11

4-Chloro-2-((2-chloro-4-cyanophenyl)carbamoyl) phenyl morpholine-4-carboxylate (11)

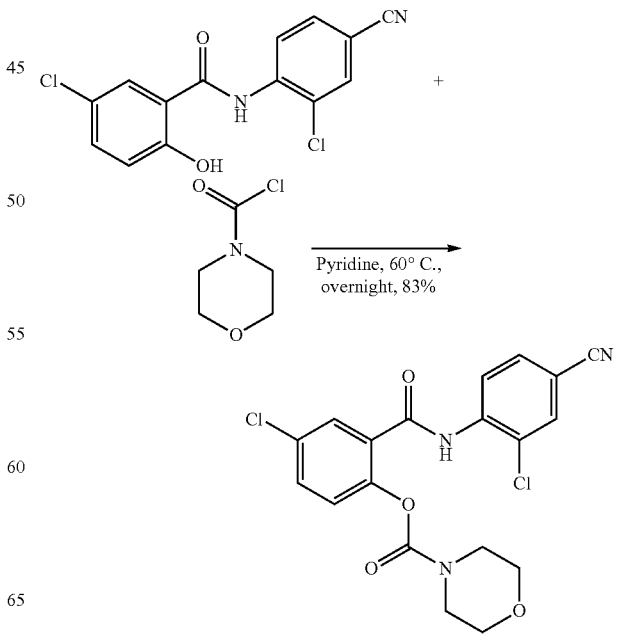

To a stirred solution of 5-chloro-N-(2-chloro-4-cyanophenyl)-2-hydroxybenzamide (90 mg, 0.293 mmol) in pyridine (3.0 mL) was added morpholine-4-carbonyl chloride (69 μL, 0.586 mmol). The reaction was heated to 60° C. for 7 h. After cooled down, 3N HCl was added. The mixture was extracted with ethyl acetate for two times. The organic layer was dried over sodium sulfate, concentrated in vacuo and the residue was purified via silica gel column chromatography to yield 4-chloro-2-((2-chloro-4-cyanophenyl)carbamoyl)phenyl morpholine-4-carboxylate 11 as a white solid (98 mg, 83% yield). $^1$H NMR (500 MHz, acetone-$d_6$) δ 9.34 (s, 1H), 8.58 (d, J=8.6 Hz, 1H), 8.01 (d, J=1.8 Hz, 1H), 7.92-7.77 (m, 2H), 7.63 (dd, J=8.7, 2.6 Hz, 1H), 7.35 (d, J=8.7 Hz, 1H), 3.69 (bs, 2H), 3.62 (bs, 4H), 3.44 (bs, 2H). MS (ESI) exact mass calculated for [M+Na]$^+$ requires m/z 442.03, found m/z 441.95.

Example 12

4-Chloro-2-((2-chloro-4-(trifluoromethyl)phenyl)carbamoyl)phenyl morpholine-4-carboxylate (12)

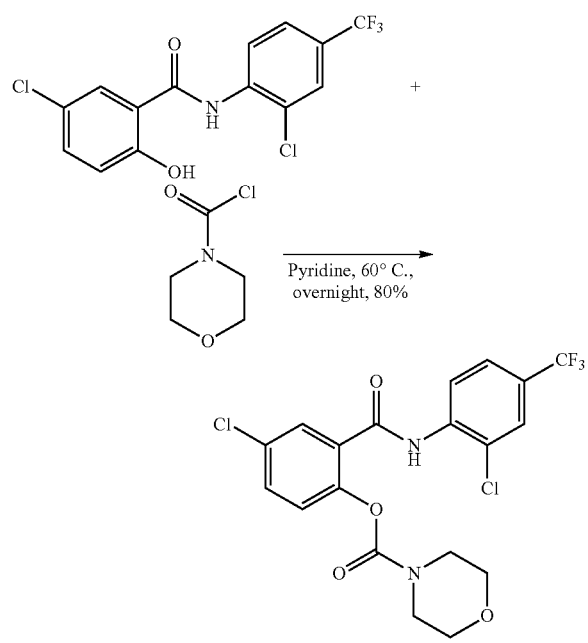

To a stirred solution of 5-chloro-N-(2-chloro-4-(trifluoromethyl)phenyl)-2-hydroxybenzamide (40 mg, 0.114 mmol) in pyridine (3.0 mL) was added morpholine-4-carbonyl chloride (27 μL, 0.228 mmol). The reaction was heated to 60° C. for 7 h. After cooled down, 3N HCl was added. The mixture was extracted with ethyl acetate for two times. The organic layer was dried over sodium sulfate, concentrated in vacuo and the residue was purified via silica gel column chromatography to yield chloro-2-((2-chloro-4-(trifluoromethyl)phenyl)carbamoyl)phenyl morpholine-4-carboxylate 12 as a white solid (42 mg, 80% yield). $^1$H NMR (400 MHz, acetone-$d_6$) δ 9.31 (s, 1H), 8.56 (d, J=8.7 Hz, 1H), 7.89 (d, J=1.8 Hz, 1H), 7.86 (d, J=2.7 Hz, 1H), 7.77 (dd, J=8.7, 1.6 Hz, 1H), 7.62 (dd, J=8.7, 2.7 Hz, 1H), 7.34 (d, J=8.8 Hz, 1H), 3.69 (brs, 2H), 3.62 (brs, 4H), 3.45 (brs, 2H). MS (ESI) exact mass calculated for [M+Na]$^+$ requires m/z 485.03, found m/z 484.95.

Example 13

4-Chloro-2-((2-chloro-4-nitrophenyl)carbamoyl)phenyl morpholine-4-carboxylate (13)

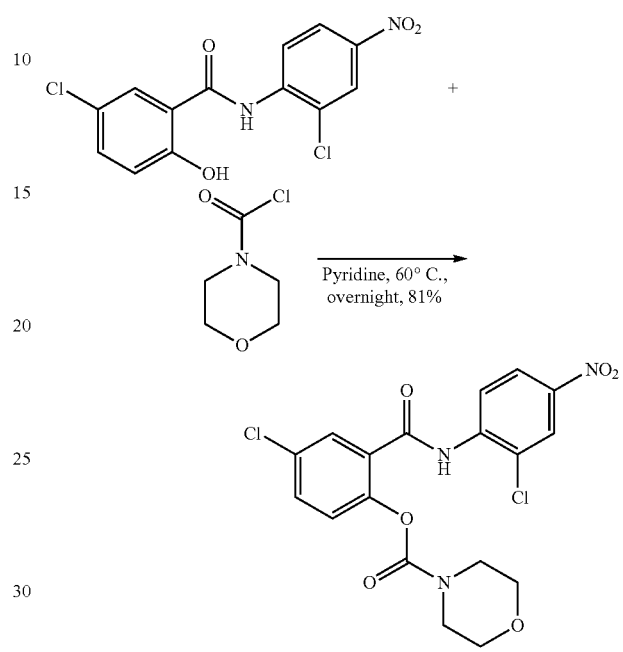

To a stirred solution of 5-chloro-N-(2-chloro-4-nitrophenyl)-2-hydroxybenzamide (327 mg, 1 mmol) in pyridine (5.0 mL) was added morpholine-4-carbonyl chloride (233 μL, 2 mmol). The reaction was heated to 60° C. for 7 h. After cooled down, 3N HCl was added. The mixture was extracted with ethyl acetate for two times. The organic layer was dried over sodium sulfate, concentrated in vacuo and the residue was purified via silica gel column chromatography to yield 4-chloro-2-((2-chloro-4-nitrophenyl)carbamoyl)phenyl morpholine-4-carboxylate 13 as a white solid (356 mg, 81% yield). $^1$H NMR (400 MHz, acetone-$d_6$) δ 9.44 (s, 1H), 8.68 (d, J=9.2 Hz, 1H), 8.41 (d, J=2.6 Hz, 1H), 8.32 (dd, J=9.2, 2.6 Hz, 1H), 7.88 (d, J=2.6 Hz, 1H), 7.65 (dd, J=8.7, 2.6 Hz, 1H), 7.36 (d, J=8.7 Hz, 1H), 3.74-3.56 (m, 6H), 3.45 (brs, 2H). MS (ESI) exact mass calculated for [M+Na]$^+$ requires m/z 462.02, found m/z 462.00.

Example 14

5-Chloro-N-(2-chloro-4-(trifluoromethyl)phenyl)-2-hydroxybenzamide (14)

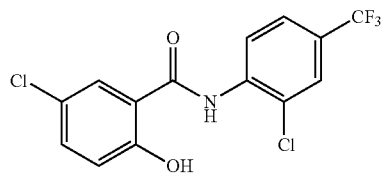

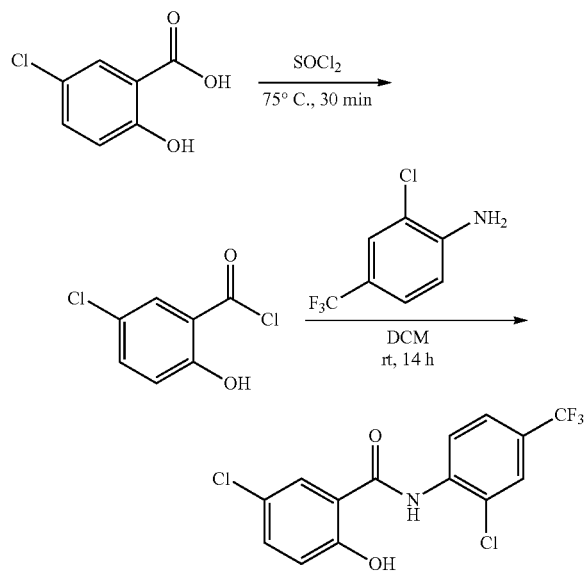

5-Chlorosalicyclic acid (508.4 mg, 2.946 mmol) was dissolved in thionyl chloride (4.0 mL). The reaction was brought to reflux at 75° C. and stirred for 30 min before it was concentrated in vacuo. The residue was re-dissolved in dichloromethane followed by addition of the trifluoromethyl aniline (0.37 mL, 2.651 mmol). The reaction was stirred at room temperature for 14 h before it was concentrated in vacuo. The solid residue was purified through silica gel column chromatography (20% acetone/hexances) to yield 5-chloro-N-(2-chloro-4-(trifluoromethyl)phenyl)-2-hydroxybenzamide 14 as an off-white solid (222.8 mg, 24% yield). $^1$H NMR (500 MHz, Chloroform-d) δ 11.37 (s, 1H), 8.54 (d, J=3.4 Hz, 1H), 8.52 (s, 1H), 7.67 (d, J=2.1 Hz, 1H), 7.55 (dd, J=8.8, 2.0 Hz, 1H), 7.46 (d, J=2.4 Hz, 1H), 7.38 (dd, J=8.9, 2.4 Hz, 1H), 6.96 (d, J=8.9 Hz, 1H). MS (ESI) exact mass calculated for [M+H] (C14H9Cl2F3NO2) requires m/z 350.0, found m/z 349.8.

Example 15

5-Chloro-N-(2-chloro-4-fluorophenyl)-2-hydroxybenzamide (15)

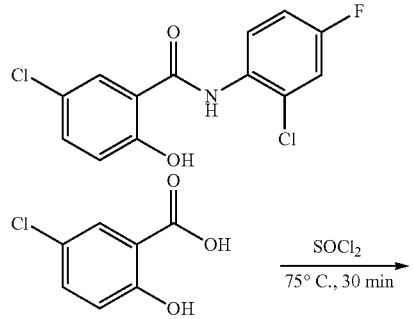

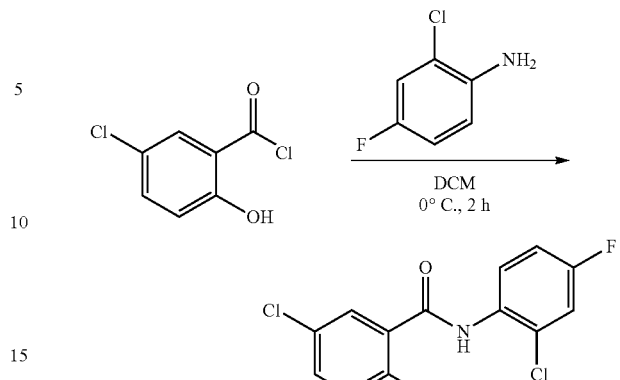

5-Chloro-2-hydroxybenzoic acid (543.4 mg, 3.149 mmol) was dissolved in thionyl chloride (4.0 mL). The reaction was brought to reflux at 75° C. and stirred for 30 min before it was concentrated in vacuo. The residue was re-dissolved in dichloromethane followed by addition of the fluoro aniline (0.36 mL, 3.149 mmol). The reaction was stirred at 0° C. for 2 h before it was concentrated in vacuo. The solid residue was purified through silica gel column chromatography (20% acetone/hexances) to yield 5-chloro-N-(2-chloro-4-fluorophenyl)-2-hydroxybenzamide 15 as an off-white solid (94.5 mg, 10% yield). $^1$H NMR (500 MHz, Methanol-d4) δ 8.33 (dd, J=9.2, 5.7 Hz, 1H), 8.04 (d, J=2.7 Hz, 1H), 7.41 (dd, J=8.8, 2.7 Hz, 1H), 7.33 (dd, J=8.3, 2.9 Hz, 1H), 7.13 (ddd, J=9.2, 8.0, 2.9 Hz, 1H), 6.98 (d, J=8.7 Hz, 1H). MS (ESI) exact mass calculated for [M+H]$^+$ requires m/z 300.0, found m/z 299.9.

Example 16

5-Chloro-N-(2-chloro-4-cyanophenyl)-2-hydroxybenzamide (16)

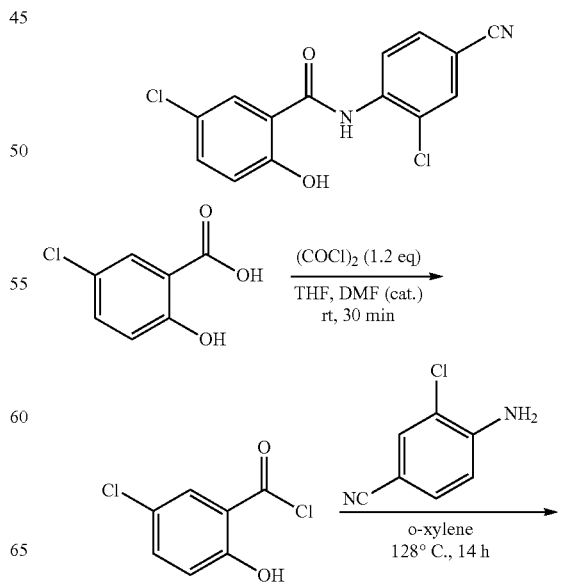

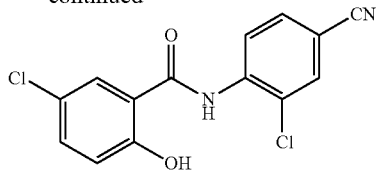

5-Chlorosalicyclic acid (561.0 mg, 3.251 mmol) was dissolved in tetrahydrofuran (8.0 mL), followed by the addition of catalytic amount of dimethylformamide (10 μL) and oxalyl chloride (0.33 mL, 3.901 mmol) respectively. The reaction was allowed to stir at room temperature for 30 min and then concentrated in vacuo. The residue was re-dissolved in o-xylene followed by addition of the cyano aniline. The mixture was then heated to 128° C. and stirred at this temperature for 14 hours before it was cooled to room temperature and filtered. The filter cake was washed with cold diethyl ether to give the crude cyano amide which was further purified through silica gel column chromatography (25% acetone/hexanes) to yield 5-chloro-N-(2-chloro-4-cyanophenyl)-2-hydroxybenzamide 16 as an off-white solid (519.0 mg, 52% yield). $^1$H NMR (500 MHz, Acetone-d$_6$) δ 8.44 (d, J=9.2 Hz, 1H), 8.29 (d, J=2.6 Hz, 1H), 8.22 (dd, J=9.2, 2.6 Hz, 1H), 7.92 (d, J=2.2 Hz, 1H), 7.62 (dd, J=8.2, 2.2 Hz, 1H), 7.43 (d, J=8.2 Hz, 1H). MS (ESI) exact mass calculated for [M+H]$^+$ requires m/z 307.0, found m/z 306.9.

Example 17

5-Chloro-N-(2-chloro-4-cyanophenyl)-2-hydroxy-benzamide-2-aminoethanol (1:1) (17)

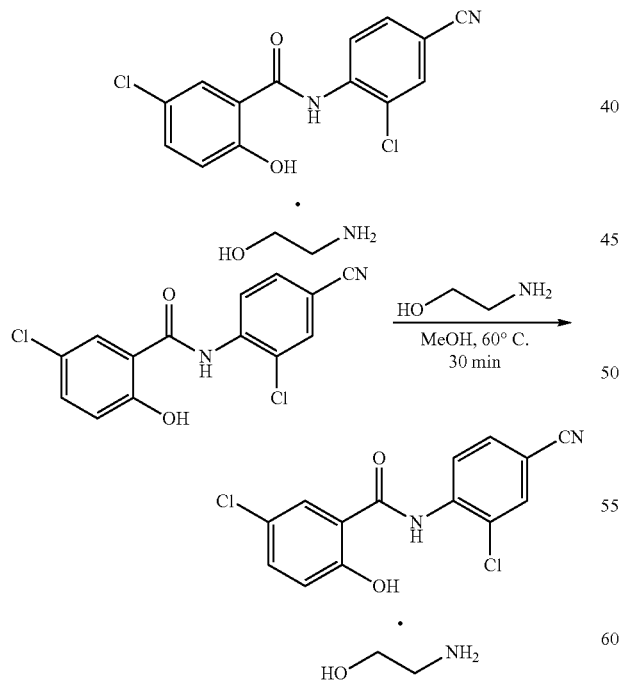

5-Chloro-N-(2-chloro-4-cyanophenyl)-2-hydroxybenz-amide (211.6 mg, 0.689 mmol) was suspended in methanol (25.0 mL) in a flask and 2-aminoethanol (50 μL, 0.827 mmol) was added to the mixture. The reaction was heated to 60° C. and stirred at this temperature for 30 minutes. The reaction was cooled to room temperature and filtered to remove unreacted 4-cyano amide. The filtrate was placed in a −10° C. refrigerator for 14 hours, and the solid crashed-out was collected and washed with diethyl ether to yield 5-chloro-N-(2-chloro-4-cyanophenyl)-2-hydroxybenzamide salt with 2-aminoethanol (1:1) 17 as a pale yellow crystalline solid (221.0 mg, 60% yield). $^1$H NMR (500 MHz, DMSO-d$_6$) δ 8.87 (d, J=8.7 Hz, 1H), 7.93 (d, J=2.0 Hz, 1H), 7.65 (dd, J=8.7, 2.0 Hz, 1H), 7.62 (d, J=3.1 Hz, 1H), 7.26 (br s, 3H), 6.98 (dd, J=8.9, 3.1 Hz, 1H), 6.42 (d, J=8.9 Hz, 1H), 5.05 (br s, 2H), 3.54 (t, J=5.4 Hz, 2H), 2.80 (t, J=5.4 Hz, 2H).

Example 18

4-Chloro-2-((6-(trifluoromethyl)benzo[d]thiazol-2-yl)carbamoyl)phenyl [1,4'-bipiperidine]-1'-carboxy-late (18)

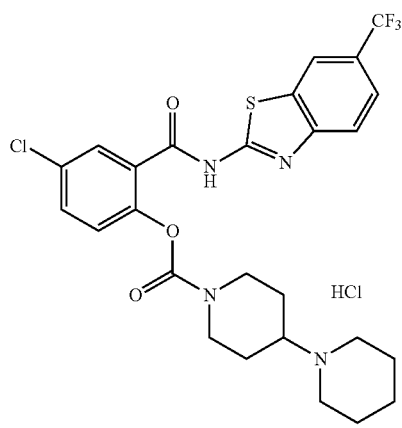 [SMILES: O=C(Nc1nc2ccc(C(F)(F)F)cc2s1)c1cc(Cl)ccc1OC(=O)N1CCC(N2CCCCC2)CC1 ; Cl]

$^1$H NMR (400 MHz, DMSO-d$_6$) δ 10.37 (brs, 1H), 8.54 (s, 1H), 7.98 (d, 1H, J=8.8 Hz), 7.89 (d, 1H, J=2.8 Hz), 7.81-7.78 (m, 1H), 7.73-7.70 (m, 1H), 7.38 (d, 1H, J=8.8 Hz), 4.36-3.97 (m, 3H), 3.36-2.99 (m, 4H), 2.83-2.67 (m, 3H), 2.33-1.29 (m, 10H). MS (ESI) [M+H]$^+$ requires m/z 567.14, found m/z. 567.7.

Example 19

4-chloro-2-((6-(trifluoromethyl)benzo[d]thiazol-2-yl)carbamoyl)phenyl dimethylglycinate

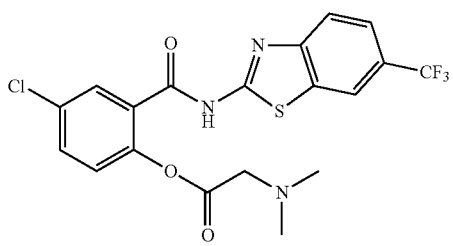 [SMILES: CN(C)CC(=O)Oc1ccc(Cl)cc1C(=O)Nc1nc2ccc(C(F)(F)F)cc2s1]

Example 20

4-Chloro-2-((6-(trifluoromethyl)benzo[d]thiazol-2-yl)carbamoyl)phenyl prolinate hydrochloride (20)

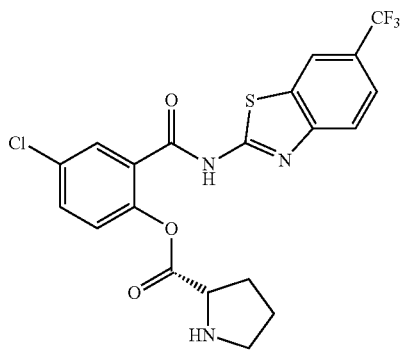

$^1$H NMR (400 MHz, DMSO-d$_6$) δ 12.54 (brs, 1H), 10.09 (brs, 1H), 8.46 (s, 1H), 8.05 (d, J=8.4 Hz, 1H), 7.82 (d, J=2.8 Hz, 1H), 7.45 (dd, J$_1$=8.8 Hz, J$_2$=2.8 Hz, 1H), 6.99 (d, J=8.8 Hz, 1H). MS (ESI) [M+H]$^+$ requires m/z 470.06, found m/z. 470.4.

Example 21

5-Chloro-N-(4-fluoro-6-(trifluoromethyl)benzo[d]thiazol-2-yl)-2-hydroxybenzamide (21)

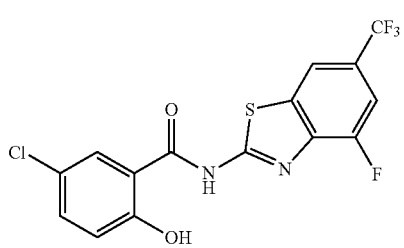 [SMILES: O=C(Nc1nc2c(F)cc(C(F)(F)F)cc2s1)c1cc(Cl)ccc1O]

$^1$H NMR (400 MHz, DMSO-d$_6$) δ 12.59 (brs, 1H), 8.44 (s, 1H), 7.91 (s, 1H), 7.76 (d, J=10.8 Hz, 1H), 7.55 (d, J=8.4 Hz, 1H), 7.10 (d, J=8.8 Hz, 1H). MS (ESI) [M−H]$^−$ requires m/z 388.98, found m/z. 389.4.

Example 22

N-(4,6-Bis(trifluoromethyl)benzo[d]thiazol-2-yl)-5-chloro-2-hydroxybenzamide (22)

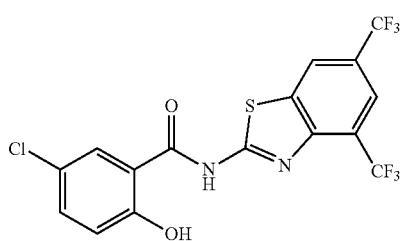 [SMILES: O=C(Nc1nc2c(C(F)(F)F)cc(C(F)(F)F)cc2s1)c1cc(Cl)ccc1O]

$^1$H NMR (400 MHz, DMSO-d$_6$) δ 13.00 (brs, 1H), 8.90 (s, 1H), 8.05 (s, 1H), 7.89 (d, J=2.4 Hz, 1H), 7.54-7.51 (m, 1H), 7.07 (d, J=8.8 Hz, 1H). MS (ESI) [M−H]$^−$ requires m/z 438.97, found m/z. 439.6.

Example 23

5-Chloro-N-(4,6-difluorobenzo[d]thiazol-2-yl)-2-hydroxybenzamide (23)

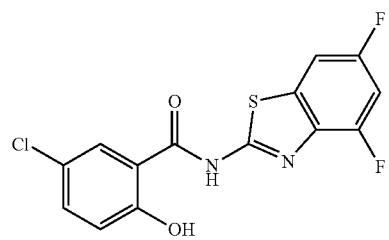 [SMILES: O=C(Nc1nc2c(F)cc(F)cc2s1)c1cc(Cl)ccc1O]

$^1$H NMR (400 MHz, DMSO-d$_6$) δ 12.25 (brs, 1H), 7.91-7.82 (m, 2H), 7.54-7.38 (m, 2H), 7.09 (d, 1H, J=8.8 Hz). MS (ESI) [M+H]$^+$ requires m/z 341.00, found m/z. 341.2.

Example 24

5-Chloro-N-(6-fluoro-4-(trifluoromethyl)benzo[d]thiazol-2-yl)-2-hydroxybenzamide (24)

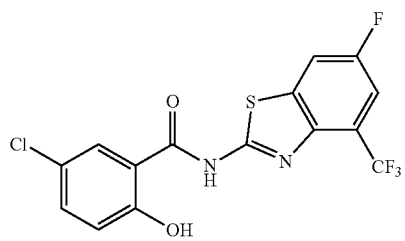 [SMILES: O=C(Nc1nc2c(C(F)(F)F)cc(F)cc2s1)c1cc(Cl)ccc1O]

$^1$H NMR (400 MHz, DMSO-d$_6$) δ 12.54 (brs, 1H), 11.79 (brs, 1H), 8.34 (d, J=6.0 Hz, 1H), 7.89 (d, J=2.8 Hz, 1H), 7.77-7.75 (m, 1H), 7.54-7.51 (m, 1H), 7.08 (d, J=9.2 Hz, 1H). MS (ESI) [M−H]$^−$ requires m/z 388.98, found m/z. 389.4.

Example 25

5-Chloro-2-hydroxy-N-(5-(trifluoromethyl)benzo[d]thiazol-2-yl)benzamide (25)

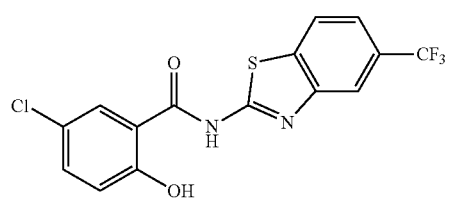 [SMILES: O=C(Nc1nc2cc(C(F)(F)F)ccc2s1)c1cc(Cl)ccc1O]

$^1$H NMR (400 MHz, DMSO-d$_6$) δ 11.18 (brs, 1H), 8.42 (d, J=2.0 Hz, 1H), 8.13 (dd, J$_1$=8.8 Hz, J$_2$=2.4 Hz, 1H), 8.05

(d, J=8.8 Hz, 1H), 7.82 (d, J=2.4 Hz, 1H), 7.46 (dd, J₁=8.8 Hz, J₂=2.8 Hz, 1H), 7.00 (d, J=8.8 Hz, 1H). MS (ESI) [M–H]⁻ requires m/z 370.99, found m/z. 370.8.

Example 26

5-Chloro-2-hydroxy-N-(7-(trifluoromethyl)benzo[d]thiazol-2-yl)benzamide (26)

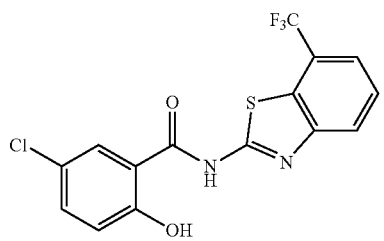 [SMILES: O=C(Nc1nc2cccc(C(F)(F)F)c2s1)c1cc(Cl)ccc1O]

¹H NMR (400 MHz, DMSO-d₆) δ 11.29 (brs, 1H), 8.42 (d, J=2.0 Hz, 1H), 8.12 (dd, J₁=8.4 Hz, J₂=2.0 Hz, 1H), 8.05 (d, J=8.4 Hz, 1H), 7.82 (d, J=2.8 Hz, 1H), 7.45 (dd, J₁=8.8 Hz, J₂=2.8 Hz, 1H), 6.99 (d, J=8.8 Hz, 1H). MS (ESI) [M–H]⁻ requires m/z 370.99, found m/z. 371.3.

Example 27

5-Chloro-3-ethyl-2-hydroxy-N-(6-(trifluoromethyl)benzo[d]thiazol-2-yl)benzamide (27)

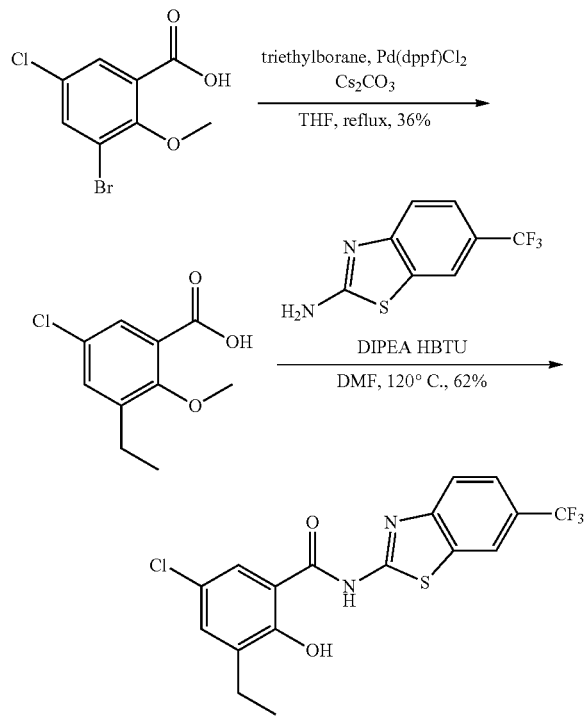

To a stirred solution of 3-bromo-5-chloro-2-methoxybenzoic acid (355 mg, 1.34 mmol), Pd(dppf)Cl₂ (20 mg, 0.027 mmol) and Cs₂CO₃ (1.31 g, 4.02 mmol) in THF (10 ml) under N₂ was added triethylborane (4.02 ml, 1M in THF). The mixture was refluxed under N₂ for 6 h. After cooled down, the reaction was acidified to PH=1 using 1N HCl and extracted with EA. The EA layer dried over Na2SO4 and concentrated under reduced pressure. The residue was purified via silica gel column chromatography to give 5-chloro-2-methoxy-3-ethylbenzoic acid as a white solid (100 mg, 36%). ¹H NMR (300 MHz, Chloroform-d) δ 7.89 (d, J=2.7 Hz, 1H), 7.44 (d, J=2.7 Hz, 1H), 3.91 (s, 3H), 2.73 (q, J=9.0 Hz, 2H), 1.28 (t, J=9.0 Hz, 3H).

5-chloro-2-methoxy-3-ethylbenzoic acid (100 mg, 0.467 mmol) was dissolved in DMF (5 ml). HBTU (213 mg, 0.561 mmol) was added followed by DIPEA (244 ul, 1.40 mmol). The resulting mixture was stirred at rt for 15 mins, then 6-(trifluoromethyl)benzo[d]thiazol-2-amine (102 mg, 0.467 mmol) was added. The resulting mixture was stirred at 120° C. for 24 h. Saturated NH₄Cl solution was added and extracted with EA for two times. The combined EA layer was dried over Na₂SO₄ and concentrated under reduced pressure. The residue was purified via silica gel column chromatography to give title compound as a yellow powder (115 mg, 62%). ¹H NMR (300 MHz, Acetone-d6) δ 8.40 (s, 1H), 8.10 (s, 1H), 7.90 (d, J=8.7 Hz, 1H), 7.81 (d, J=8.1 Hz, 1H), 7.39 (s, 1H), 2.72 (q, J=9.0 Hz, 2H), 1.24 (t, J=9.0 Hz, 3H). MS (ESI) [M+H]⁺ requires m/z 401.03, found m/z 400.6.

Example 28

5-Chloro-2-hydroxy-3-methyl-N-(6-(trifluoromethyl)benzo[d]thiazol-2-yl)benzamide ethanolamine (28)

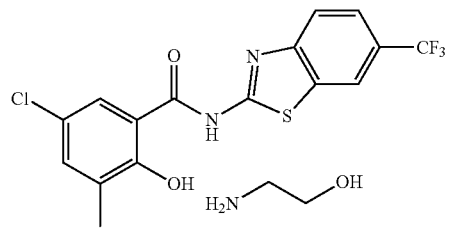

To a stirred solution of MB1-37 (200 mg, 0.517 mmol) in MeOH (5 ml) was added ethanolamine (35 ul, 0.569 mmol) and the resulting mixture was refixed for 1 h. After cooled to rt, the unreacted MB1-37 was filtered out and the filtrate was concentrated and vacuumed to give MB1-47 (200 mg, 87%) as a pale yellow solid. ¹H NMR (300 MHz, methanol) δ 8.11 (s, 1H), 7.77-7.73 (m, 2H), 7.62-7.59 (m, 1H), 7.16-7.14 (m, 1H), 3.73 (t, J=6.0 Hz, 2H), 3.01 (t, J=6.0 Hz, 2H), 2.22 (s, 3H).

Example 29

5-Chloro-N-(6-fluorobenzo[d]thiazol-2-yl)-2-hydroxy-3-methylbenzamide (29)

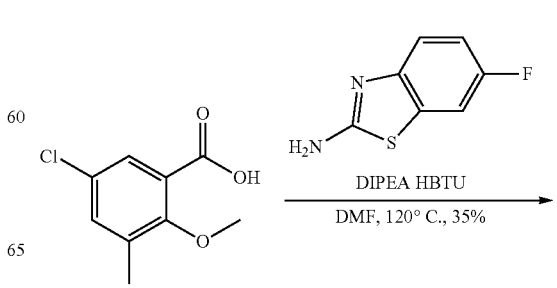

-continued

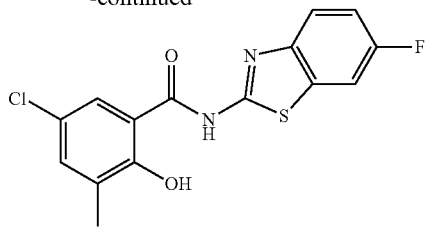

5-chloro-2-methoxy-3-methylbenzoic acid (100 mg, 0.498 mmol) was dissolved in DMF (5 ml). HBTU (228 mg, 0.60 mmol) was added followed by DIPEA (261 ul, 1.50 mmol). The resulting mixture was stirred at rt for 15 mins, then 6-fluorobenzo[d]thiazol-2-amine (84 mg, 0.498 mmol) was added. The resulting mixture was stirred at 120° C. for 24 h. Saturated NH$_4$Cl solution was added and extracted with EA for two times. The combined EA layer was dried over Na$_2$SO$_4$ and concentrated under reduced pressure. The residue was purified via silica gel column chromatography to give title compound as a yellow solid (58 mg, 35%). $^1$H NMR (300 MHz, Chloroform-d) δ 8.02 (d, J=2.4 Hz, 1H), 7.64 (dd, J=8.9, 4.5 Hz, 1H), 7.47 (dd, J=7.9, 2.6 Hz, 1H), 7.25 (dd, J=1.8, 0.9 Hz, 1H), 7.16 (td, J=8.8, 2.5 Hz, 1H), 2.23 (s, 3H). MS (ESI) [M+H]$^+$ requires m/z 337.02, found m/z 336.6.

Example 30

3,5-Dichloro-2-hydroxy-N-(6-(trifluoromethyl)benzo[d]thiazol-2-yl)benzamide (30)

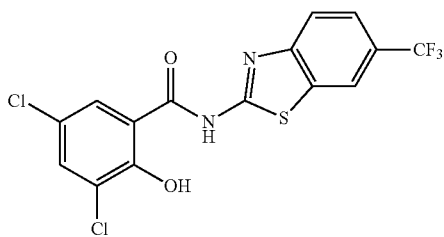 [SMILES: O=C(Nc1nc2ccc(C(F)(F)F)cc2s1)c1cc(Cl)cc(Cl)c1O]

3,5-dichlorosalicylic acid (104 mg, 0.5 mmol) was dissolved in THF (3.0 mL), followed by the addition of catalytic amount of DMF (1 drop) and oxalyl chloride (51 uL, 0.6 mmol) respectively. The reaction was allowed to stir at rt for 30 min and concentrated in vacuo. The residue was re-dissolved in dioxane (5.0 mL) and 6-(trifluoromethyl)benzo[d]thiazol-2-amine (109 mg, 0.5 mmol) was added. The mixture was refluxed overnight. Solvent was evaporated and the resulting residue was purified via silica gel column chromatography to yield the title compound (35 mg, 18%) as a white solid. $^1$H NMR (400 MHz, Acetone-d6) δ 8.66 (s, 1H), 8.33 (d, J=8.6 Hz, 1H), 8.12 (d, J=2.5 Hz, 1H), 8.04 (d, J=2.5 Hz, 1H), 7.96 (dd, J=8.6, 1.4 Hz, 1H). MS (ESI) [M−H]$^+$ requires m/z 404.96, found m/z 405.20.

Example 31

5-Chloro-2-hydroxy-3-methyl-N-(4-(trifluoromethyl)benzo[d]thiazol-2-yl)benzamide (31)

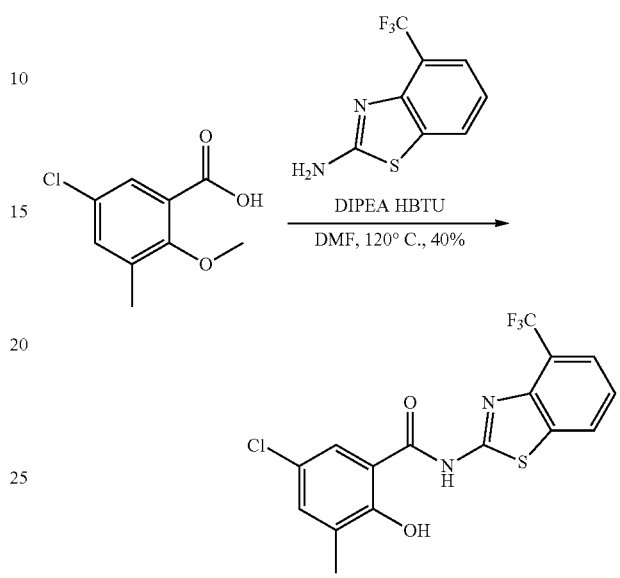

5-chloro-2-methoxy-3-methylbenzoic acid (71 mg, 0.355 mmol) was dissolved in DMF (5 ml). HBTU (162 mg, 0.426 mmol) was added followed by DIPEA (248 ul, 1.42 mmol). The resulting mixture was stirred at rt for 15 mins, then 4-(trifluoromethyl)benzo[d]thiazol-2-amine (77 mg, 0.355 mmol) was added. The resulting mixture was stirred at 120° C. for 24 h. Saturated NH$_4$Cl solution was added and extracted with EA for two times. The combined EA layer was dried over Na$_2$SO$_4$ and concentrated under reduced pressure. The residue was purified via silica gel column chromatography to give title compound as a yellow solid (55 mg, 40%). $^1$H NMR (300 MHz, Chloroform-d) δ 8.05 (d, J=8.0 Hz, 1H), 7.78 (d, J=7.7 Hz, 1H), 7.53 (s, 1H), 7.44 (t, J=8.0 Hz, 1H), 7.34 (s, 1H), 2.29 (s, 3H). MS (ESI) [M+Na]$^+$ requires m/z 409.00, found m/z 408.4.

Example 32

5-Chloro-2-hydroxy-N-(4-(trifluoromethyl)benzo[d]thiazol-2-yl)benzamide ethanolamine (32)

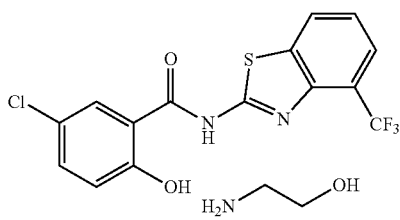

To a stirred solution of 5-chloro-2-hydroxy-N-(4-(trifluoromethyl)benzo[d]thiazol-2-yl)benzamide (29 mg, 0.078 mmol) in MeOH (5 ml) was added ethanolamine (5.2 ul, 0.086 mmol) and the resulting mixture was refixed for 1 h. After cooled to rt, the unreacted starting material was filtered out and the filtrate was concentrated and vacuumed to give the title compound (30 mg, 91%) as a pale yellow solid. $^1$H NMR (300 MHz, Methanol-d4) δ 8.08 (d, J=7.9 Hz, 1H), 7.88 (d, J=2.9 Hz, 1H), 7.69 (d, J=7.6 Hz, 1H), 7.35 (t, J=7.8 Hz, 1H), 7.22 (dd, J=8.8, 3.0 Hz, 1H), 6.79 (d, J=8.9 Hz, 1H), 3.80-3.70 (m, 2H), 3.02 (t, J=5.2 Hz, 2H).

Example 33

5-Chloro-2-hydroxy-N-(6-(trifluoromethyl)benzo[d]thiazol-2-yl)benzamide ethanolamine (33)

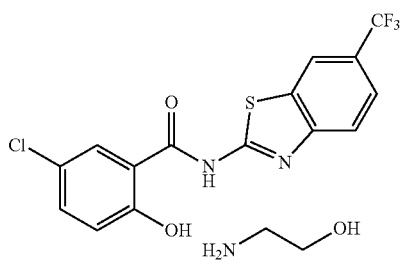

To a stirred solution of 5-chloro-2-hydroxy-N-(6-(trifluoromethyl)benzo[d]thiazol-2-yl)benzamide (235 mg, 0.632 mmol) in MeOH (6 ml) was added ethanolamine (42 ul, 0.695 mmol) and the resulting mixture was refixed for 1 h. After cooled to rt, the unreacted starting material was filtered out and the filtrate was concentrated and vacuumed to give the title compound (246 mg, 90%) as a pale yellow solid. $^1$H NMR (300 MHz, Methanol-d4) δ 8.16 (s, 1H), 7.89 (s, 1H), 7.78 (d, J=8.6 Hz, 1H), 7.64 (d, J=8.5 Hz, 1H), 7.23 (d, J=8.9 Hz, 1H), 6.80 (d, J=8.8 Hz, 1H), 3.82-3.67 (m, 2H), 3.07-2.95 (m, 2H).

Example 34

5-Chloro-2-hydroxy-3-methyl-N-(4-(trifluoromethyl)benzo[d]thiazol-2-yl)benzamide ethanolamine (34)

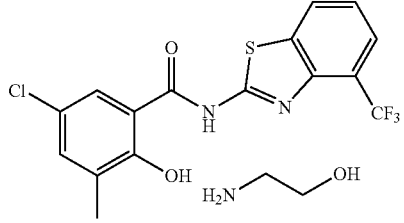

To a stirred solution of 5-chloro-2-hydroxy-3-methyl-N-(4-(trifluoromethyl)benzo[d]thiazol-2-yl)benzamide (20 mg, 0.0517 mmol) in MeOH (5 ml) was added ethanolamine (3.5 ul, 0.0569 mmol) and the resulting mixture was refixed for 1 h. After cooled to rt, the unreacted starting material was filtered out and the filtrate was concentrated and vacuumed to give the title compound (20 mg, 87%) as a pale yellow solid. $^1$H NMR (300 MHz, Methanol-d4) δ 8.06 (d, J=7.9 Hz, 1H), 7.75 (d, J=2.9 Hz, 1H), 7.67 (d, J=7.7 Hz, 1H), 7.32 (t, J=7.4 Hz, 1H), 7.15 (d, J=2.9 Hz, 1H), 3.77-3.69 (m, 2H), 3.03-2.96 (m, 2H).

Example 35

5-Chloro-N-(4,6-difluorobenzo[d]thiazol-2-yl)-2-hydroxybenzamide ethanolamine(35)

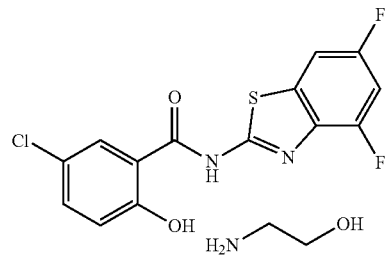

To a stirred solution of 5-chloro-N-(4,6-difluorobenzo[d]thiazol-2-yl)-2-hydroxybenzamide (49 mg, 0.144 mmol) in MeOH (5 ml) was added ethanolamine (10 ul, 0.158 mmol) and the resulting mixture was refixed for 1 h. After cooled to rt, the unreacted starting material was filtered out and the filtrate was concentrated and vacuumed to give the title compound (50 mg, 88%) as a pale yellow solid. $^1$H NMR (300 MHz, Methanol-d4) δ 7.87 (t, J=2.9 Hz, 1H), 7.47-7.36 (m, 1H), 7.21 (dd, J=8.9, 2.9 Hz, 1H), 7.07-6.92 (m, 1H), 6.79 (d, J=8.8 Hz, 1H), 3.69 (t, J=5.3 Hz, 2H), 2.92 (t, J=5.4 Hz, 2H).

Example 36

5-Chloro-3-cyclopropyl-2-hydroxy-N-(6-(trifluoromethyl)benzo[d]thiazol-2-yl)benzamide (36)

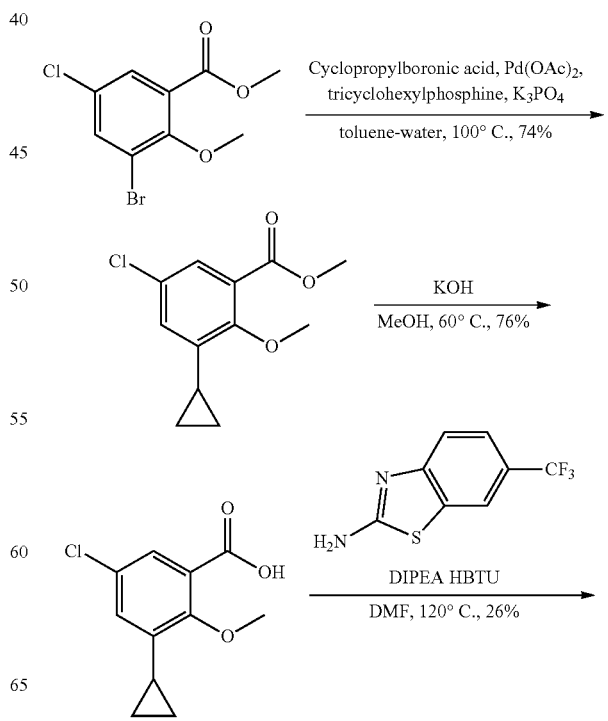

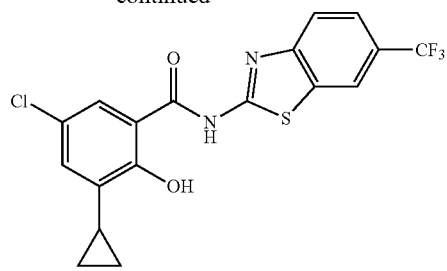

A mixture of methyl 3-bromo-5-chloro-2-methoxybenzoate (280 mg, 1 mmol), cyclopropylboronic acid (258 mg, 3 mmol), Pd(OAc)$_2$ (22 mg, 0.1 mmol), tricyclohexylphosphine (56 mg, 0.2 mmol) and potassium phosphate tribasic (743 mg, 3.5 mmol) in toluene (10 ml) and water (2 ml) was stirred at 100° C. overnight. After the reaction was cooled, saturated NH$_4$Cl solution was added and extracted with EA for two times. The combined EA layer was dried over Na$_2$SO$_4$ and concentrated under reduced pressure. The residue was purified via silica gel column chromatography to give methyl 5-chloro-3-cyclopropyl-2-methoxybenzoate as a colorless oil (177 mg, 74%). $^1$H NMR (500 MHz, Chloroform-d) δ 7.53 (d, J=2.7 Hz, 1H), 6.90 (d, J=2.6 Hz, 1H), 3.90 (s, 4H), 3.88 (s, 3H), 2.21 (tt, J=8.5, 5.3 Hz, 1H), 1.05-1.00 (m, 2H), 0.69-0.66 (m, 2H).

To a stirred solution of methyl 5-chloro-3-cyclopropyl-2-methoxybenzoate (177 mg, 0.74 mmol) in MeOH (5 ml) was added 3.6 ml 1N KOH solution. The resulting mixture was stirred at 60° C. overnight. The solvent was evaporated out and the residue was portioned between EA and 1N NaOH solution. The aqueous layer was acidified to pH=1 and extracted with EA. This organic phase was dried over over Na$_2$SO$_4$ and concentrated in vacuo to afford 5-chloro-3-cyclopropyl-2-methoxybenzoic acid as a white solid (120 mg, 76%) which used in the next step without further purification.

To a stirred solution of 5-chloro-3-cyclopropyl-2-methoxybenzoic acid (120 mg, 0.53 mmol) and HBTU (243 mg, 0.64 mmol) in DMF (5 ml) was added DIPEA (277 ul, 1.59 mmol). The mixture was stirred for 10 mins and then 6-(trifluoromethyl)benzo[d]thiazol-2-amine (92 mg, 0.42 mmol) was added. The resulting reaction was heated at 120° C. for 24 hs. After cooled to rt, the mixture was separated between EA and water. The organic layer was washed with brine, dried over Na$_2$SO$_4$ and concentrated in vacuo. Purification by column chromatography gave the title compound as a yellow solid (45 mg, 26%). $^1$H NMR (300 MHz, Chloroform-d) δ 8.11 (s, 1H), 7.70-7.63 (m, 2H), 6.98 (d, J=3.0 Hz, 1H), 6.71 (d, J=3.0 Hz, 1H), 2.20-2.10 (m, 1H), 1.05-1.00 (m, 2H), 0.70-0.65 (m, 2H). MS (ESI) [M+H]$^+$ requires m/z 413.03, found m/z 413.15.

Example 37

5-Chloro-2-hydroxy-3-methyl-N-(6-(trifluoromethyl)benzo[d]thiazol-2-yl)benzamide compound with (2R,3R,4R,5S)-6-(methylamino)hexane-1,2,3,4,5-pentaol (1:1) (37)

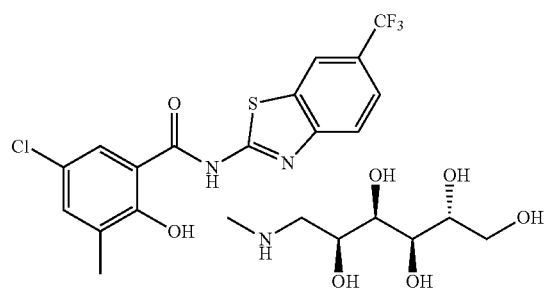

To a stirred solution of 5-chloro-2-hydroxy-3-methyl-N-(6-(trifluoromethyl)benzo[d]thiazol-2-yl)benzamide (100 mg, 0.248 mmol) in MeOH (5 ml) was added N-methyl-D-glucamine (48 mg, 0.248 mmol) and the resulting mixture was refixed for 1 h. After cooled to rt, the unreacted starting material was filtered out and the filtrate was concentrated and vacuumed to give the title compound (125 mg, 84%) as a pale yellow solid. $^1$H NMR (300 MHz, Methanol-d4) δ 8.10 (s, 1H), 7.74 (d, J=7.4 Hz, 2H), 7.59 (d, J=8.8 Hz, 1H), 7.13 (s, 1H), 4.08-3.89 (m, 2H), 3.87-3.52 (m, 6H), 3.11 (d, J=6.0 Hz, 2H), 2.67 (s, 3H), 2.22 (s, 3H).

Example 38

5-Chloro-2-hydroxy-3-isopropyl-N-(6-(trifluoromethyl)benzo[d]thiazol-2-yl)benzamide (38)

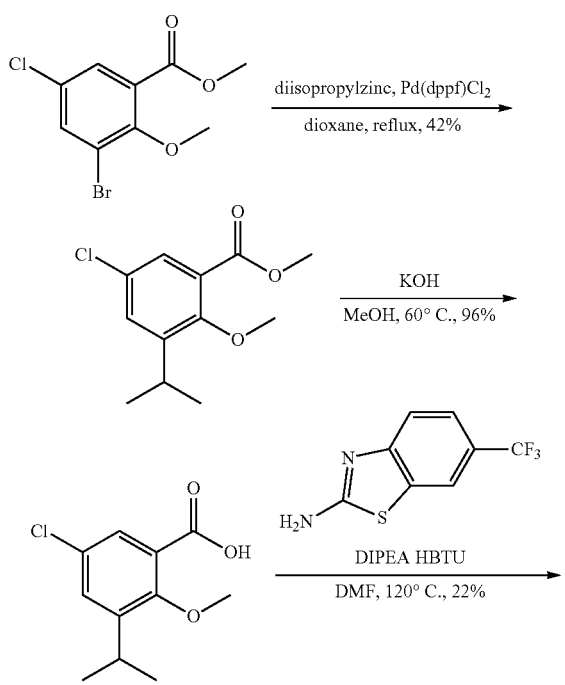

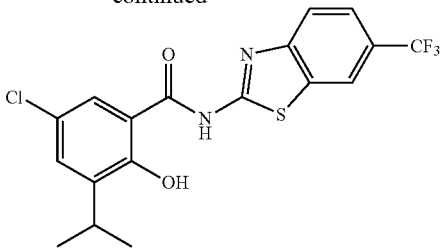

Under N$_2$, methyl 3-bromo-5-chloro-2-methoxybenzoate (280 mg, 1 mmol) was added in one portion to a solution of diisopropylzinc (2 ml, 1M in toluene) in dioxane (10 ml) followed by addition of Pd(dppf)Cl$_2$ (82 mg, 0.1 mmol). The mixture was heated to reflux for 3 h. After cooled to rt, the mixture was quenched with 1N HCl and diluted with EA. The separated organic layer was washed with 1N HCl, water, brine, dried, filtered and concentrated under reduced pressure. The residue was purified by column chromatography to afford the methyl 5-chloro-3-isopropyl-2-methoxybenzoate (100 mg, 42%) as a pale yellow oil. $^1$H NMR (300 MHz, Chloroform-d) δ 7.62 (d, J=2.7 Hz, 1H), 7.37 (d, J=2.7 Hz, 1H), 3.93 (s, 3H), 3.83 (s, 3H), 3.38 (p, J=6.9 Hz, 1H), 1.23 (d, J=6.9 Hz, 7H).

To a stirred solution of methyl 5-chloro-3-isopropyl-2-methoxybenzoate (100 mg, 0.413 mmol) in MeOH (5 ml) was added 2.0 ml 1N KOH solution. The resulting mixture was stirred at 60° C. overnight. The solvent was evaporated out and the residue was portioned between EA and 1N NaOH solution. The aqueous layer was acidified to pH=1 and extracted with EA. This organic phase was dried over over Na$_2$SO$_4$ and concentrated in vacuo to afford 5-chloro-3-isopropyl-2-methoxybenzoic acid as a colorless oil (90 mg, 96%) which used in the next step without further purification.

To a stirred solution of 5-chloro-3-isopropyl-2-methoxybenzoic acid (90 mg, 0.395 mmol) and HBTU (180 mg, 0.474 mmol) in DMF (5 ml) was added DIPEA (206 ul, 1.185 mmol). The mixture was stirred for 10 mins and then 6-(trifluoromethyl)benzo[d]thiazol-2-amine (86 mg, 0.395 mmol) was added. The resulting reaction was heated at 120° C. for 24 hs. After cooled to rt, the mixture was separated between EA and water. The organic layer was washed with brine, dried over Na$_2$SO$_4$ and concentrated in vacuo. Purification by column chromatography gave the title compound as a yellow solid (35 mg, 22%). $^1$H NMR (300 MHz, Chloroform-d) δ 8.17 (s, 1H), 7.66 (s, 2H), 7.50 (d, J=2.5 Hz, 1H), 7.34 (d, J=1.7 Hz, 1H), 3.51-3.35 (m, 1H), 1.28 (d, J=6.9 Hz, 6H). MS (ESI) [M+H]$^+$ requires m/z 415.05, found m/z 415.05.

Example 39

4-Chloro-2-methyl-6-((6-(trifluoromethyl)benzo[d]thiazol-2-yl)carbamoyl)phenyl [1,4'-bipiperidine]-1'-carboxylate hydrochloride (39)

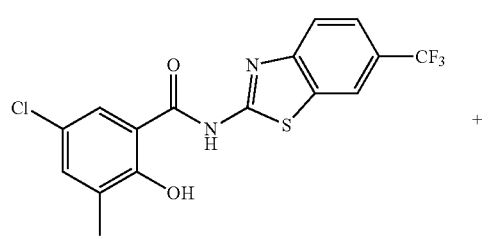

+

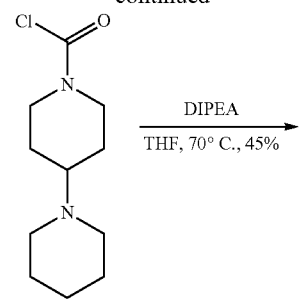

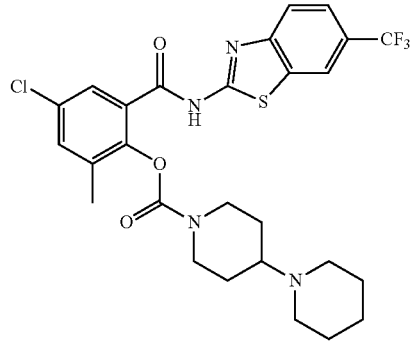

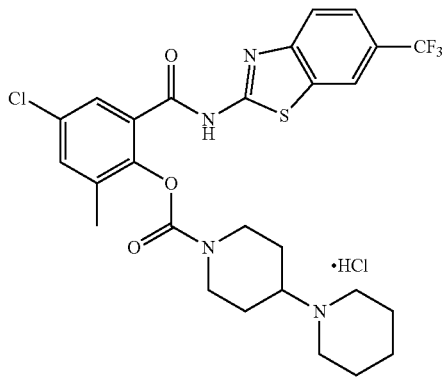

To a stirred solution of 5-chloro-2-hydroxy-3-methyl-N-(6-(trifluoromethyl)benzo[d]thiazol-2-yl)benzamide (60 mg, 0.155 mmol) in THF (5 ml) was added DIPEA (81 ul, 0.465 mmol) and [1,4'-bipiperidine]-1'-carbonyl chloride (72 mg, 0.31 mmol). The mixture was stirred at 70° C. for 16 h. After cooled to rt, the reaction was portioned between EA and water. The EA layer was dried over Na$_2$SO$_4$ and concentrated under reduced pressure. The residue was purified via silica gel column chromatography to give title compound as a yellow oil (40 mg, 45%). $^1$H NMR (300 MHz, Chloroform-d) δ 8.08 (s, 1H), 7.75 (d, 1H, J=6.0 Hz), 7.62 (d, 1H, J=6.0 Hz), 7.56 (d, 1H, J=3.0 Hz), 7.36 (d, 1H, J=3.0 Hz), 4.53-4.41 (m, 3H), 3.18-2.75 (m, 9H), 2.27 (s, 3H), 1.83-1.69 (m, 7H). MS (ESI) [M+H]+ requires m/z 581.15, found m/z 580.85.

To a stirred solution of 4-chloro-2-methyl-6-((6-(trifluoromethyl)benzo[d]thiazol-2-yl)carbamoyl)phenyl [1,4'-bipiperidine]-1'-carboxylate (40 mg, 0.069 mmol) in THF (3 ml) was added 4.0N HCl in dioxane (18 ul, 0.07 mmol). The mixture was stirred at rt for 20 mins. The resulting precipitate was filtered and washed with diethyl ether to afford the title compound as a yellow solid (42 mg, 100%).

Example 40

5-Chloro-N-(4,6-difluorobenzo[d]thiazol-2-yl)-2-hydroxy-3-methylbenzamide (40)

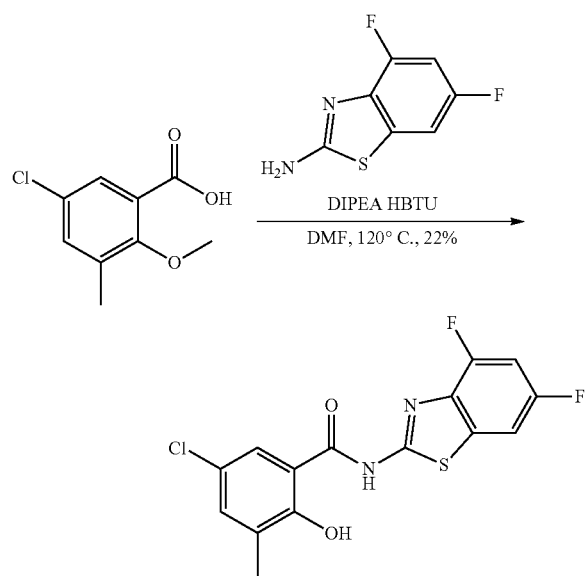

5-chloro-2-methoxy-3-methylbenzoic acid (100 mg, 0.498 mmol) was dissolved in DMF (5 ml). HBTU (228 mg, 0.60 mmol) was added followed by DIPEA (261 ul, 1.50 mmol). The resulting mixture was stirred at rt for 15 mins, then 4,6-difluorobenzo[d]thiazol-2-amine (90 mg, 0.498 mmol) was added. The resulting mixture was stirred at 120° C. for 24 h. Saturated NH$_4$Cl solution was added and extracted with EA for two times. The combined EA layer was dried over Na$_2$SO$_4$ and concentrated under reduced pressure. The residue was purified via silica gel column chromatography to give title compound as a white solid (40 mg, 22%). $^1$H NMR (300 MHz, Chloroform-d) δ 7.41 (d, J=3.0 Hz, 1H), 7.39-7.36 (m, 1H), 7.33 (d, J=3.0 Hz, 1H), 7.00-6.95 (m, 1H), 2.29 (s, 3H). MS (ESI) [M+H]+ requires m/z 355.01, found m/z 354.4.

Example 41

5-Chloro-2-hydroxy-3-methyl-N-(5-(trifluoromethyl)benzo[d]thiazol-2-yl)benzamide (41)

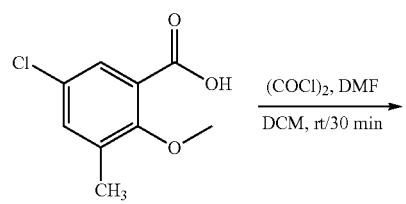

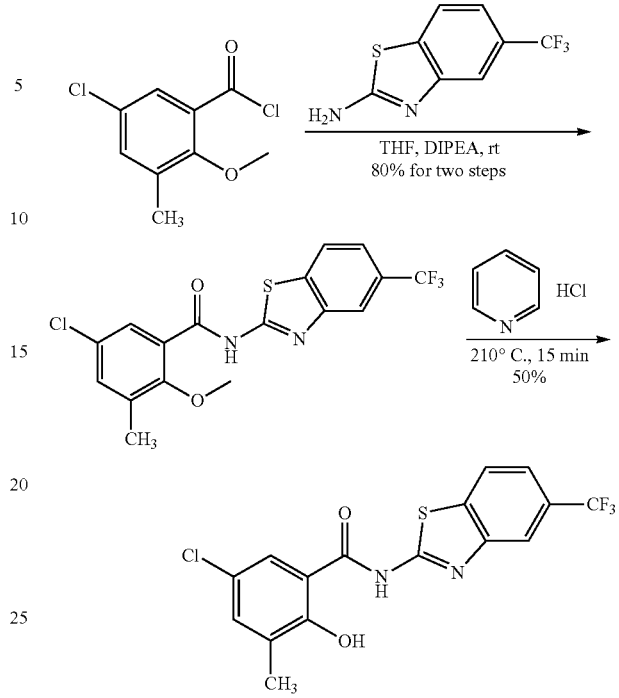

5-chloro-2-methoxy-3-methylbenzoic acid (71 mg, 0.354 mmol) was dissolved in DCM (3.0 mL), followed by the addition of catalytic amount of DMF (2 drops) and oxalyl chloride (37 uL, 0.425 mmol) respectively. The reaction was allowed to stir at rt for 30 min and concentrated in vacuo. The residue was re-dissolved in THF (5.0 mL), and Hunig's base (74 uL, 0.425 mmol) and 5-(trifluoromethyl)benzo[d]thiazol-2-amine (62 mg, 0.283 mmol) were added. The mixture was stirred at rt for 48 hours before silica gel was added to quench the reaction. Solvent was evaporated and the resulting residue was purified via silica gel column chromatography to yield 5-chloro-2-methoxy-3-methyl-N-(5-(trifluoromethyl)benzo[d]thiazol-2-yl)benzamide (90 mg, 80% yield) as a white solid. $^1$H NMR (500 MHz, Chloroform-d) δ 9.86 (s, 1H), 7.97 (s, 1H), 7.80-7.71 (m, 2H), 7.67 (d, J=8.6 Hz, 1H), 7.18 (s, 1H), 3.66 (s, 3H), 2.16 (s, 3H). MS (ESI) [M+H]+ requires m/z 401.03, found m/z 400.7.

5-chloro-2-methoxy-3-methyl-N-(5-(trifluoromethyl)benzo[d]thiazol-2-yl)benzamide (90 mg, 0.225 mmol) was mixed with pyridinium chloride (1.0 g). The mixture was heated to 210° C., stirred for 15 minutes and cooled down to rt. The resulting solid was dissolved in water and extracted with ethyl acetate. The organic layer was concentrated in vacuo and the residue was purified via silica gel column chromatography to yield the title compound as a yellow solid (43.0 mg, 50% yield). $^1$H NMR (500 MHz, Chloroform-d) δ 11.50 (s, 1H), 7.97-7.89 (m, 2H), 7.79-7.70 (m, 2H), 7.20 (s, 1H), 7.16 (s, 1H), 2.11 (s, 3H). MS (ESI) [M+H]+ requires m/z 387.02, found m/z 386.70.

Example 42

5-Chloro-2-hydroxy-3-methyl-N-(7-(trifluoromethyl)benzo[d]thiazol-2-yl)benzamide (42)

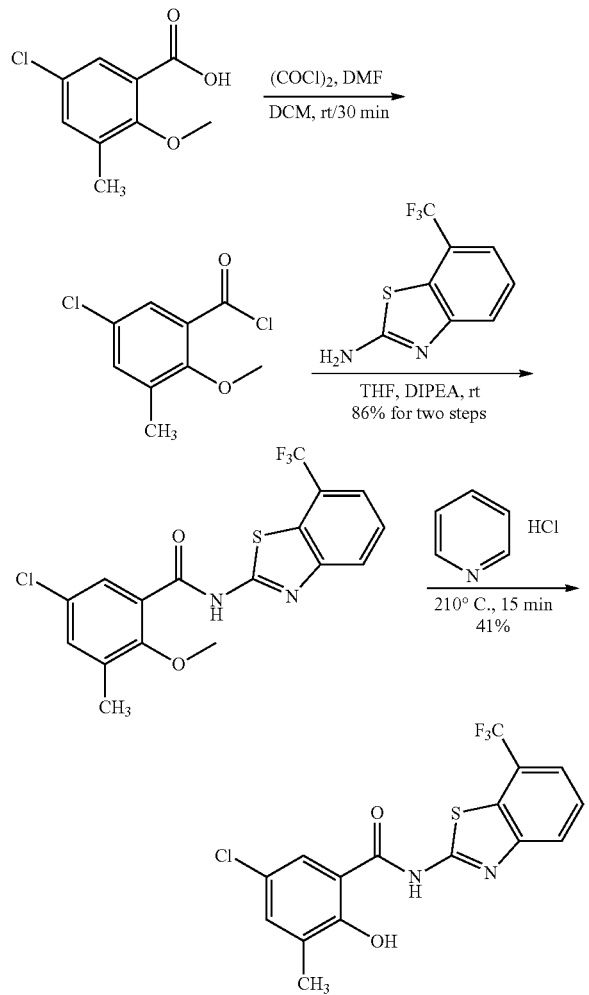

5-chloro-2-methoxy-3-methylbenzoic acid (74 mg, 0.369 mmol) was dissolved in DCM (3.0 mL), followed by the addition of catalytic amount of DMF (2 drops) and oxalyl chloride (38 uL, 0.443 mmol) respectively. The reaction was allowed to stir at rt for 30 min and concentrated in vacuo. The residue was re-dissolved in THF (5.0 mL), and Hunig's base (78 uL, 0.443 mmol) and 7-(trifluoromethyl)benzo[d]thiazol-2-amine (64 mg, 0.295 mmol) were added. The mixture was stirred at rt for 48 hours before silica gel was added to quench the reaction. Solvent was evaporated and the resulting residue was purified via silica gel column chromatography to yield 5-chloro-2-methoxy-3-methyl-N-(7-(trifluoromethyl)benzo[d]thiazol-2-yl)benzamide (102 mg, 86% yield) as a white solid. $^1$H NMR (300 MHz, Chloroform-d) δ 10.09 (s, 1H), 8.19 (d, J=2.4 Hz, 1H), 8.06-7.84 (m, 3H), 7.40 (dd, J=2.8, 0.8 Hz, 1H), 3.88 (s, 3H), 2.39 (s, 3H). MS (ESI) [M+H]+ requires m/z 401.03, found m/z 401.70.

5-chloro-2-methoxy-3-methyl-N-(7-(trifluoromethyl)benzo[d]thiazol-2-yl)benzamide (102 mg, 0.255 mmol) was mixed with pyridinium chloride (1.0 g). The mixture was heated to 210° C., stirred for 15 minutes and cooled down to rt. The resulting solid was dissolved in water and extracted with ethyl acetate. The organic layer was concentrated in vacuo and the residue was purified via silica gel column chromatography to yield the title compound as a yellow solid (40 mg, 41% yield). $^1$H NMR (300 MHz, Chloroform-d) δ 11.85 (s, 1H), 8.10 (s, 1H), 7.96 (s, 1H), 7.90-7.77 (m, 2H), 7.38 (s, 1H), 7.32 (s, 1H), 2.29 (s, 3H). MS (ESI) [M+H]+ requires m/z 387.02, found m/z 386.70.

Example 43 and Example 44

4-Chloro-2-methyl-6-((6-(trifluoromethyl)benzo[d]thiazol-2-yl)carbamoyl)phenyl dihydrogen phosphate (43)

Sodium 4-chloro-2-methyl-6-((6-(trifluoromethyl)benzo[d]thiazol-2-yl)carbamoyl)phenyl phosphate (44)

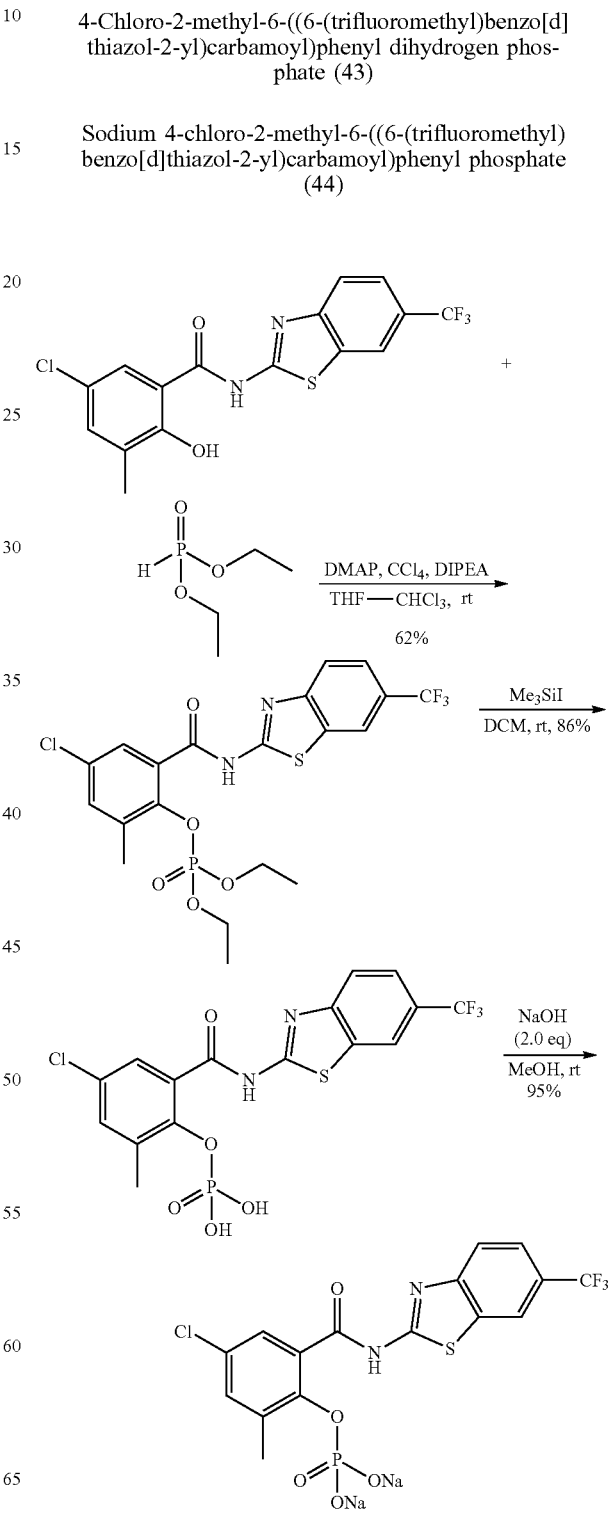

4-chloro-2-methyl-6-((6-(trifluoromethyl)benzo[d]thiazol-2-yl)carbamoyl)phenyl diethyl phosphate

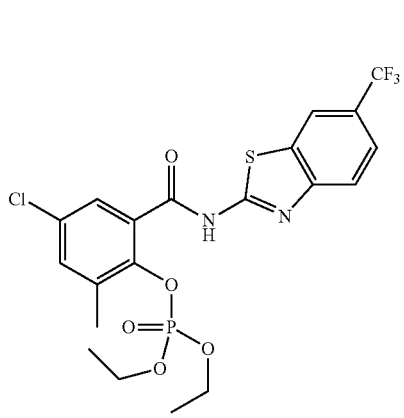 [SMILES: CCOP(=O)(OCC)Oc1c(C)cc(Cl)cc1C(=O)Nc1nc2ccc(C(F)(F)F)cc2s1]

To a stirred solution of MB1-37 (163 mg, 0.42 mmol) in CHCl$_3$ (8 ml) and THF (2 ml) at 0° C. was added diethyl phosphite (66 ul, 0.51 mmol), CCl$_4$ (0.3 ml), DMAP (7 mg, 0.051 mmol) and DIPEA (0.17 ml). The mixture was allowed to gradually warm to rt and stirred at rt for 14 h before it was concentrated in Vacuo. The residue was purified via silica gel to yield the product as a pale yellow solid (130 mg, 62%). MS (ESI) [M+H]+ requires m/z 523.05, found m/z 523.8.

4-chloro-2-methyl-6-((6-(trifluoromethyl)benzo[d]thiazol-2-yl)carbamoyl)phenyl dihydrogen phosphate (43)

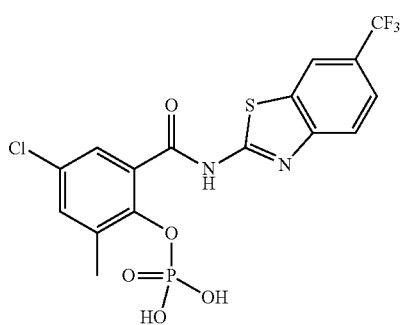 [SMILES: Cc1cc(Cl)cc(C(=O)Nc2nc3ccc(C(F)(F)F)cc3s2)c1OP(=O)(O)O]

To a stirred solution of 4-chloro-2-methyl-6-((6-(trifluoromethyl)benzo[d]thiazol-2-yl)carbamoyl)phenyl diethyl phosphate (63 mg, 0.12 mmol) in anhydrous DCM (4 ml) was added dropwise trimethylsilyl iodide (86 ul, 0.6 mmol) at rt. The mixture was stirred at rt for 2 ds. The solvent was evaporated out and MeOH (10 ml) was added to the residue and the mixture was stirred at rt for 30 min. The reaction mixture was filtered and the filtrate was concentrated to afford a brown solid. This brown solid was washed with ether three times and then with small amount of water to afford the product as a yellow solid (43 mg, 86%). 1H NMR (300 MHz, methanol) δ 8.25 (s, 1H), 7.81 (brs, 1H), 7.68 (brs, 1H), 7.52 (s, 1H), 7.47 (s, 1H), 2.39 (s, 3H). MS (ESI) [M+H]+ requires m/z 466.98, found m/z 466.45.

sodium 4-chloro-2-methyl-6-((6-(trifluoromethyl)benzo[d]thiazol-2-yl)carbamoyl)phenyl phosphate (44)

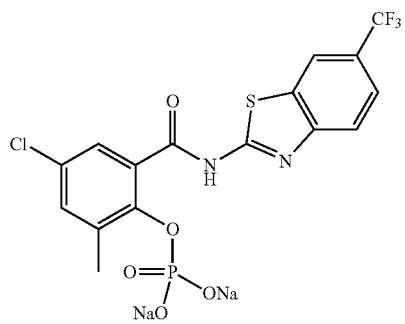

To a stirred solution of 4-chloro-2-methyl-6-((6-(trifluoromethyl)benzo[d]thiazol-2-yl)carbamoyl)phenyl dihydrogen phosphate (20 mg, 0.043 mmol) in MeOH (2 ml) was added a solution of NaOH (3.4 mg, 0.086 mmol) in MeOH (1.5 ml). The mixture was stirred at rt for 30 min and the solvent was removed to yield a yellow solid which was washed with ether and a small amount of water to afford the MB1-70 as a pale yellow solid (20 mg, 95%).

Example 45

4-Chloro-2-methyl-6-((6-(trifluoromethyl)benzo[d]thiazol-2-yl) carbamoyl)phenyl morpholine-4-carboxylate (45)

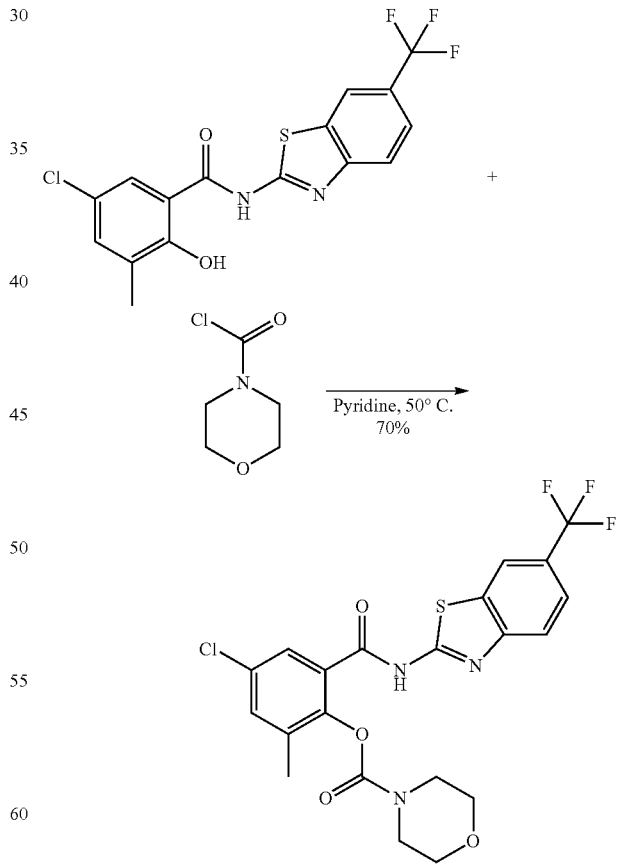

To a stirred solution of 5-chloro-3-methyl-2-hydroxy-N-(6-(trifluoromethyl)benzo[d]thiazol-2-yl)benzamide (47 mg, 0.121 mmol) in pyridine (3.0 mL) was added morpholine-4-carbonyl chloride (28 μL, 0.243 mmol). The reaction was heated to 50° C. for 7 h. After cooled down, 3N HCl was added. The mixture was extracted with EA for two times. The organic layer was dried over sodium sulfate, concentrated in vacuo and the residue was purified via silica gel column chromatography to yield the title compound as a white solid (42.0 mg, 70% yield). ¹H NMR (300 MHz, Acetone-d6) δ 11.62 (s, 1H), 8.48 (s, 1H), 8.02-7.89 (m, 1H), 7.85-7.71 (m, 2H), 7.66-7.54 (m, 1H), 3.87-3.38 (m, 8H), 2.32 (s, 3H). MS (ESI) [M+H]+ requires m/z 500.07, found m/z 499.6.

Example 46

4-Chloro-2-methyl-6-((6-(trifluoromethyl)benzo[d]thiazol-2-yl)carbamoyl)phenyl 4-methylpiperazine-1-carboxylate hydrochloride (46)

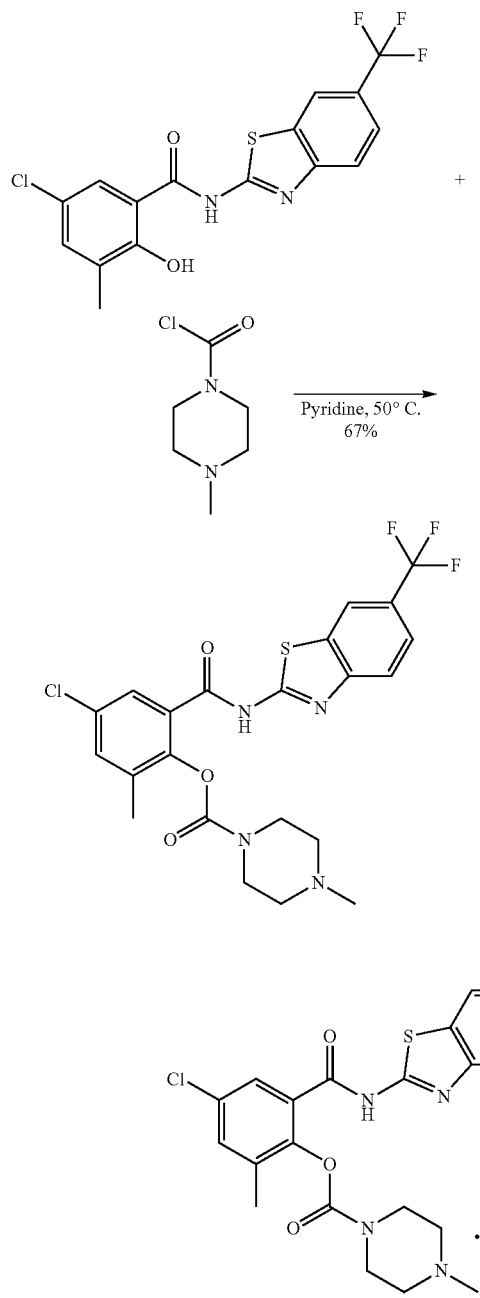

To a stirred solution of 5-chloro-3-methyl-2-hydroxy-N-(6-(trifluoromethyl)benzo[d]thiazol-2-yl)benzamide (48 mg, 0.124 mmol) in pyridine (3.0 mL) was added 4-methylpiperazine-1-carbonyl chloride (34 μL, 0.248 mmol). The reaction was heated to 50° C. for 7 h. After cooled down, 3N HCl was added. The mixture was extracted with EA for two times. The combined organic layer was washed with 3N HCl, water, brine, dried over sodium sulfate, concentrated in vacuo. The resulting white solid was washed with hexanes twice to yield the title compound as a white solid (42.0 mg, 67% yield). ¹H NMR (300 MHz, Methanol-d4) δ 8.35 (s, 1H), 7.96 (d, J=8.5 Hz, 1H), 7.74 (d, J=2.7 Hz, 2H), 7.62 (s, 1H), 3.01 (s, 3H), 2.32 (s, 3H), 1.30 (brs, 8H). MS (ESI) [M+Na]⁺ requires m/z 535.08, found m/z 535.45.

Example 47

4-Chloro-2-methyl-6-((6-(trifluoromethyl)benzo[d]thiazol-2-yl)carbamoyl)phenyl piperazine-1-carboxylate hydrochloride (47)

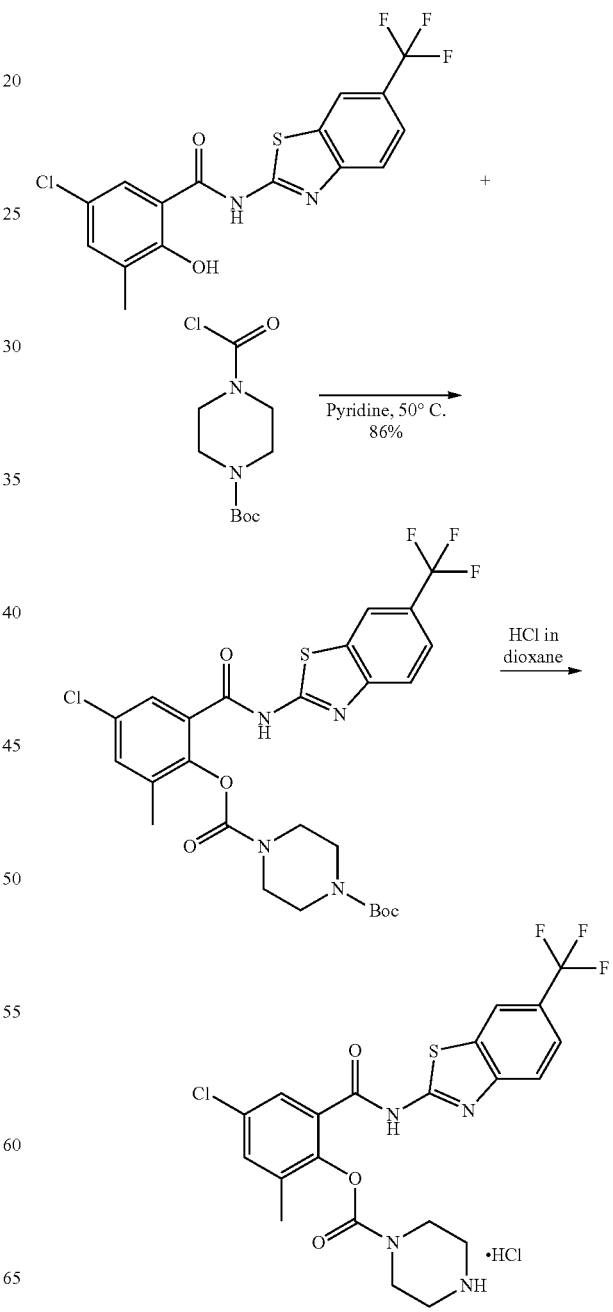

To a stirred solution of 5-chloro-3-methyl-2-hydroxy-N-(6-(trifluoromethyl)benzo[d]thiazol-2-yl)benzamide (59 mg, 0.152 mmol) in pyridine (3.0 mL) was added tert-butyl 4-(chlorocarbonyl)piperazine-1-carboxylate (46 mg, 0.183 mmol). The reaction was heated to 50° C. for 7 h. After cooled down, the solvent was removed and the residue was portioned between EA and water. The organic layer was washed with water, brine, dried over sodium sulfate, concentrated in vacuo. The resulting yellow oil was treated with 4N HCl in dioxane (5 ml) and the mixture was stirred at rt for 2 h. The solvent was removed and the remaining white solid was washed with diethyl ether three times to give the title compound as a white solid (70.0 mg, 86% yield). $^1$H NMR (500 MHz, Methanol-d4) δ 8.20 (brs, 1H), 7.78 (brs, 1H), 7.58 (brs, 2H), 7.45 (brs, 1H), 3.77 (brs, 4H), 3.51 (brs, 4H), 2.18 (s, 3H). MS (ESI) [M+H]$^+$ requires m/z 499.08, found m/z 498.85.

Example 48

5-Chloro-3-cyano-2-hydroxy-N-(6-(trifluoromethyl)benzo[d]thiazol-2-yl)benzamide (48)

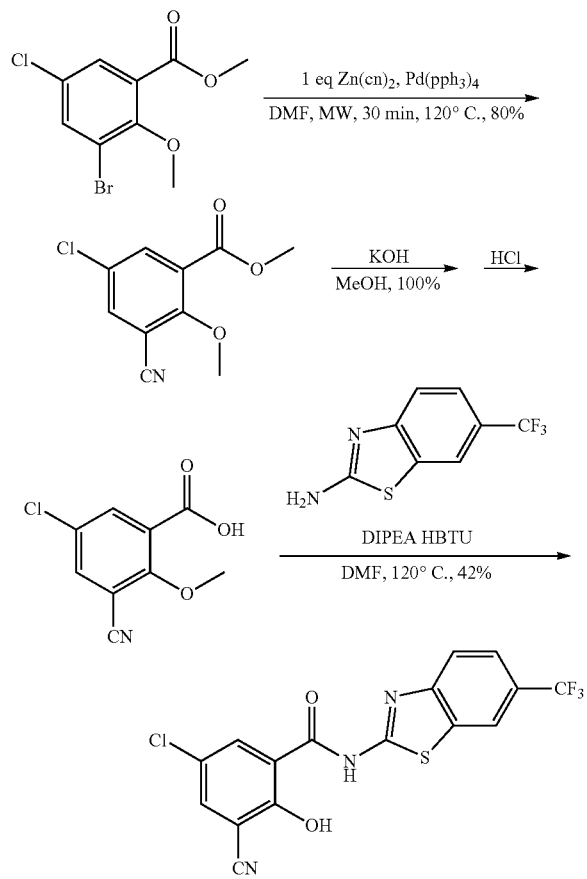

A mixture of methyl 3-bromo-5-chloro-2-methoxybenzoate (279 mg, 1 mmol), Zn(CN)$_2$ (117 mg, 1 mmol), Pd(PPh3)4 (35 mg, 0.03 mmol) was microwaved at 120° C. under N$_2$ for 30 min. After cooled to rt, the mixture was separated between EA and water. The separated organic layer was washed with water, brine, dried, filtered and concentrated under reduced pressure. The residue was purified by column chromatography to afford methyl 5-chloro-3-cyano-2-methoxybenzoate (180 mg, 80%) as a white solid. $^1$H NMR (300 MHz, Chloroform-d) δ 7.97 (d, J=2.7 Hz, 1H), 7.70 (d, J=2.7 Hz, 1H), 4.06 (s, 3H), 3.95 (s, 3H).

To a stirred solution of methyl 5-chloro-3-cyano-2-methoxybenzoate (86 mg, 0.382 mmol) in MeOH (3 ml) was added 2.0 ml 1N KOH solution. The resulting mixture was stirred at 60° C. overnight. The solvent was evaporated out and 4N HCl in dioxane (1 ml) was added to the residue. The mixture was stirred for another 10 min before it was concentrated and dried under vacumn. To this residue was added HBTU (172 mg, 0.456 mmol), DMF (3 ml) and DIPEA (330 ul, 1.9 mmol). The mixture was stirred for 10 mins and then 6-(trifluoromethyl)benzo[d]thiazol-2-amine (83 mg, 0.38 mmol) was added. The resulting reaction was heated at 120° C. for 24 hs. After cooled to rt, the mixture was separated between EA and water. The organic layer was washed with brine, dried over Na$_2$SO$_4$ and concentrated in vacuo. Purification by column chromatography gave the 5-chloro-3-cyano-2-hydroxy-N-(6-(trifluoromethyl)benzo[d]thiazol-2-yl)benzamide as a yellow solid (62 mg, 42%). $^1$H NMR (300 MHz, Acetone-d6) δ 8.31 (dt, J=1.6, 0.9 Hz, 1H), 7.85 (d, J=3.0 Hz, 1H), 7.79-7.65 (m, 2H), 7.14 (d, J=3.0 Hz, 1H). MS (ESI) [M+H]$^+$ requires m/z 398.00, found m/z 397.95.

Example 49

5-Chloro-2-hydroxy-3-(hydroxymethyl)-N-(6-(trifluoromethyl)benzo[d]thiazol-2-yl)benzamide (49)

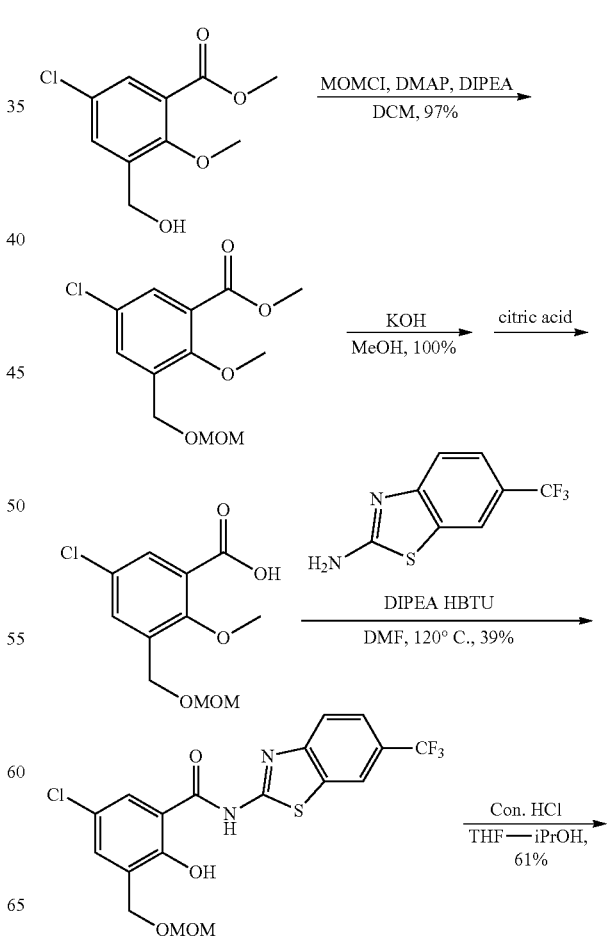

-continued

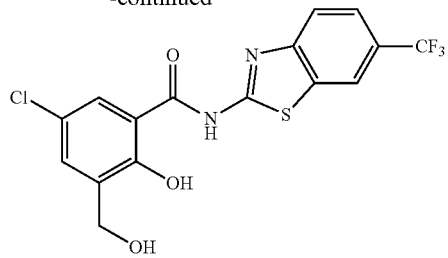

To a stirred solution of methyl 5-chloro-3-(hydroxymethyl)-2-methoxybenzoate (106 mg, 0.46 mmol) in DCM (5 ml) was added DIPEA (240 ul, 1.38 mmol), MOMCl (105 ul, 1.38 mmol) and followed by DMAP (3 mg, 0.023 mmol). The reaction mixture was stirred at rt overnight. After the reaction was completed, DCM and sat. Ammonia chloride solution were added. The organic layer was dried and concentrated, the residue was purified via silica gel column chromatography to give methyl 5-chloro-2-methoxy-3-((methoxymethoxy)methyl)benzoate (122 mg, 97%) as yellow oil. $^1$H NMR (300 MHz, Chloroform-d) δ 7.72 (d, J=2.8 Hz, 1H), 7.58 (d, J=2.9 Hz, 1H), 4.73 (s, 2H), 4.64 (s, 2H), 3.90 (s, 3H), 3.83 (s, 3H), 3.40 (s, 3H).

To a stirred solution of methyl 5-chloro-2-methoxy-3-((methoxymethoxy)methyl)benzoate (122 mg, 0.445 mmol) in MeOH (5 ml) was added 2.2 ml 1N KOH solution. The resulting mixture was stirred at 60° C. overnight. After cooled to rt, the reaction was partitioned between EA and 2% citric acid. The EA layer was washed with brine, dried over Na$_2$SO$_4$ and concentrated in vacuo. To this residue was added HBTU (98 mg, 0.258 mmol), DMF (3 ml) and DIPEA (187 ul, 1.075 mmol). The mixture was stirred for 10 mins and then 6-(trifluoromethyl)benzo[d]thiazol-2-amine (47 mg, 0.215 mmol) was added. The resulting reaction was heated at 120° C. for 24 hs. After cooled to rt, the mixture was separated between EA and water. The organic layer was washed with brine, dried over Na$_2$SO$_4$ and concentrated in vacuo. Purification by column chromatography gave the 5-chloro-2-hydroxy-3-((methoxymethoxy)methyl)-N-(6-(trifluoromethyl)benzo[d]thiazol-2 yl)benzamide as a yellow solid (37 mg, 39%). $^1$H NMR (400 MHz, Chloroform-d) δ 8.16 (s, 1H), 7.99 (d, J=2.5 Hz, 1H), 7.91 (d, J=6.1 Hz, 1H), 7.72 (d, J=6.1 Hz, 1H), 7.48 (d, J=2.5 Hz, 1H), 4.80 (s, 2H), 4.78 (s, 2H), 3.47 (s, 3H). MS (ESI) [M+Na]$^+$ requires m/z 469.02, found m/z 468.55.

To a stirred solution of 5-chloro-2-hydroxy-3-((methoxymethoxy)methyl)-N-(6-(trifluoromethyl)benzo[d]thiazol-2 yl)benzamide (37 mg, 0.083 mmol) in isopropyl (4 ml) was added concentrated HCl (4 ml). The resulting mixture was stirred at rt overnight. After completion of the reaction, water was added to the reaction and extracted with EA. The organic layer was was washed with brine, dried over sodium sulfate and concentrated in vacuo. Purification by column chromatography gave the 5-chloro-2-hydroxy-3-(hydroxymethyl)-N-(6-(trifluoromethyl)benzo[d]thiazol-2-yl)benzamide as a yellow solid (20 mg, 61%). $^1$H NMR (400 MHz, Chloroform-d) δ 8.24 (s, 1H), 7.86-7.61 (m, 4H), 4.67 (s, 2H). MS (ESI) [M+Na]$^+$ requires m/z 425.00, found m/z 424.40.

Example 50

N-(4,6-Bis(trifluoromethyl)benzo[d]thiazol-2-yl)-5-chloro-2-hydroxy-3-methylbenzamide

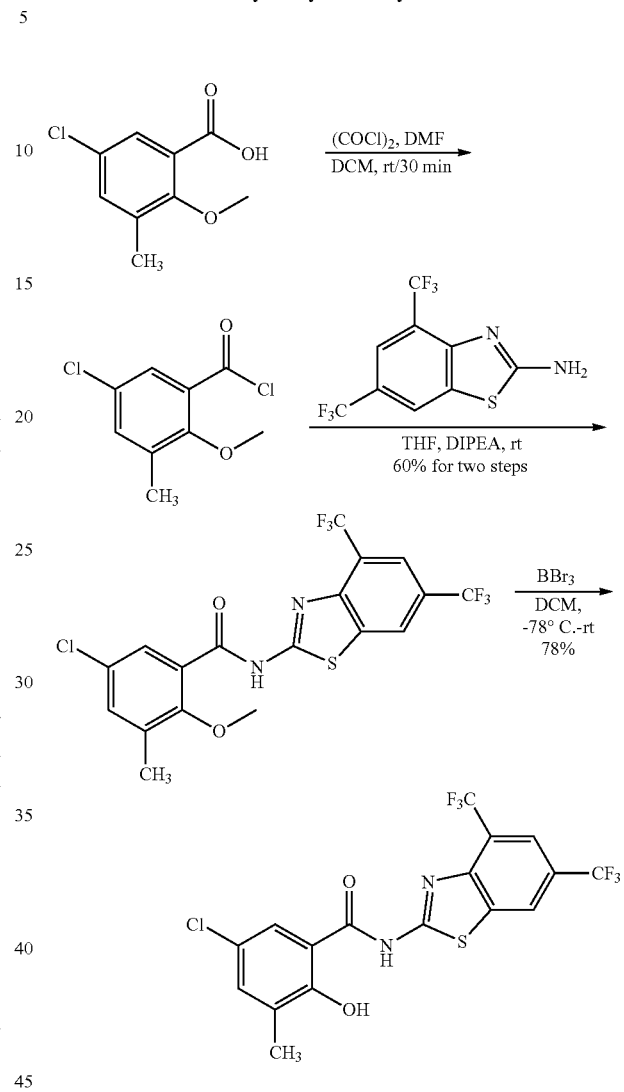

5-chloro-2-methoxy-3-methylbenzoic acid (74 mg, 0.369 mmol) was dissolved in DCM (3.0 mL), followed by the addition of catalytic amount of DMF (1 drop) and oxalyl chloride (38 uL, 0.44 mmol) respectively. The reaction was allowed to stir at rt for 30 min and concentrated in vacuo. The residue was re-dissolved in THF (5.0 mL), and Hunig's base (78 uL, 0.45 mmol) and 4,6-bis(trifluoromethyl)benzo[d]thiazol-2-amine (105 mg, 0.369 mmol) were added. The mixture was stirred at rt for 48 hours before silica gel was added to quench the reaction. Solvent was evaporated and the resulting residue was purified via silica gel column chromatography to yield 5-chloro-N-(2-chloro-4-(trifluoromethyl)phenyl)-2-methoxy-3-methylbenzamide (80 mg, 60% yield) as a white solid. $^1$H NMR (300 MHz, cdcl$_3$) δ 11.46 (s, 1H), 8.33 (s, 1H), 8.04 (d, J=2.7 Hz, 1H), 7.99 (s, 1H), 7.47 (d, J=2.7 Hz, 1H), 3.98 (s, 3H), 2.43 (s, 3H). MS (ESI) [M+H]$^+$ requires m/z 469.02, found m/z 469.45.

At −78° C., To a stirred solution of N-(4,6-bis(trifluoromethyl)benzo[d]thiazol-2-yl)-5-chloro-2-methoxy-3-methylbenzamide (80 mg, 0.176 mmol) in anhydrous DCM (5 ml) was added BBr3 (1.0M in DCM, 0.528 ml) dropwise. After addition, the reaction was allowed to warm to rt slowly and the mixture was stirred at rt for 2 h. After completion of the reaction, the reaction mixture was cooled in an ice bath and MeOH and water was added to quench the reaction. The mixture was separated between DCM and water. The organic layer was washed with water, brine and dried over sodium sulfate, concentrated in vacuo, the residue was purified via silica gel column chromatography to give the title compound (60 mg, 78%) as a white solid. $^1$H NMR (300 MHz, cdcl$_3$) δ 11.15 (s, 1H), 8.35 (s, 1H), 8.03 (s, 1H), 7.51 (d, J=2.0 Hz, 1H), 7.40 (dd, J=2.4, 0.8 Hz, 1H), 2.32 (s, 3H). MS (ESI) [M+H]+ requires m/z 455.01, found m/z 455.45.

Example 51

5-Chloro-2-hydroxy-3-methyl-N-(6-(trifluoromethoxy)benzo[d]thiazol-2-yl)benzamide (51)

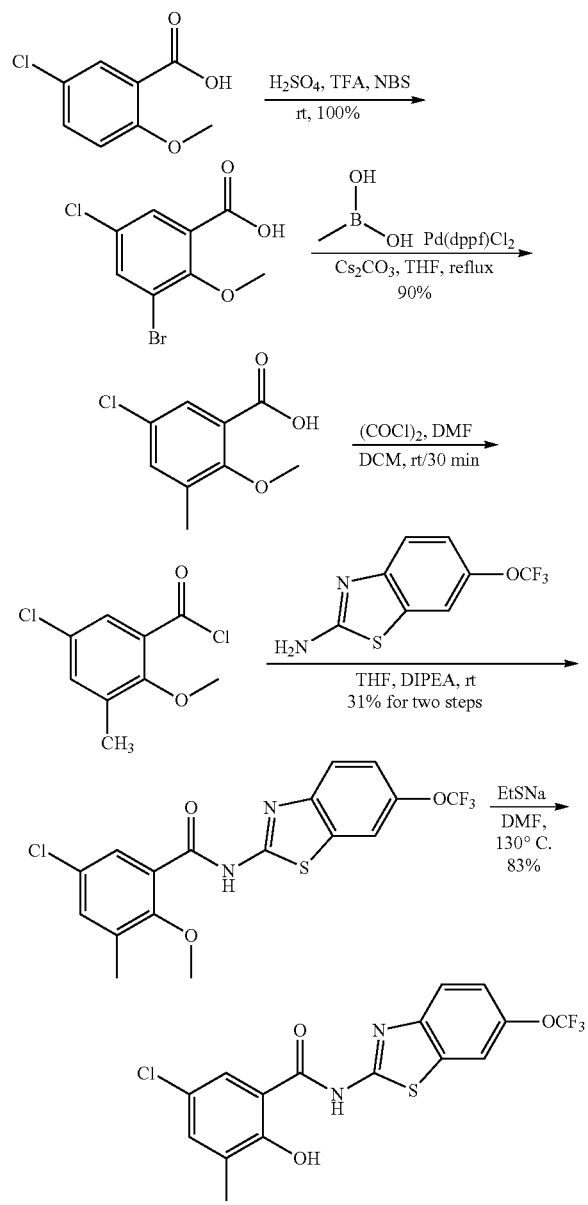

To a stirred solution of 5-Chloro-2-methoxybenzoic acid (5.59 g, 30 mmol) in sulfuric acid (10.2 ml) and TFA (20.4 ml) at rt was added NBS (5.87 g, 33 mmol). The pale solution was stirred at rt overnight. The resulting pale suspension was carefully poured onto crushed ice. The mixture was extracted with EA. The EA layer dried over Na2SO4 and concentrated under reduced pressure. The light yellow residue was suspend in minimum amount of DCM. The solid was collected, washed with cold DCM and dried under vacuum to yield the 3-bromo-5-chloro-2-methoxybenzoic acid as a white solid (8.00 g, 100%). $^1$H NMR (300 MHz, acetone) δ 7.86 (d, 1H, J=3.0 Hz), 7.78 (d, 1H, J=3.0 Hz), 3.91 (s, 3H).

A mixture of 3-bromo-5-chloro-2-methoxybenzoic acid (2.65 g, 10.0 mmol), methylboronic acid (1.79 g, 30 mmol), Pd(dppf)Cl$_2$ (163 mg, 0.2 mmol) and Cs$_2$CO$_3$ (9.77 g, 30 mmol) were refluxed in THF (30 ml) under N$_2$ overnight. The reaction was acidified to PH=1 using 1N HCl and extracted with EA. The EA layer dried over Na$_2$SO$_4$ and concentrated under reduced pressure. The residue was purified via silica gel column chromatography to give 5-chloro-2-methoxy-3-methylbenzoic acid as a white solid (1.80 g, 90%). $^1$H NMR (300 MHz, chloroform) δ 7.94 (d, 1H, J=3.0 Hz), 7.43 (d, 1H, J=3.0 Hz), 3.94 (s, 3H), 2.38 (s, 3H).

5-chloro-2-methoxy-3-methylbenzoic acid (96 mg, 0.48 mmol) was dissolved in DCM (3.0 mL), followed by the addition of catalytic amount of DMF (1 drop) and oxalyl chloride (68 uL, 0.58 mmol) respectively. The reaction was allowed to stir at rt for 30 min and concentrated in vacuo. The residue was re-dissolved in THF (5.0 mL), and Hunig's base (125 uL, 0.72 mmol) and 6-(trifluoromethoxy)benzo[d]thiazol-2-amine (135 mg, 0.576 mmol) were added. The mixture was stirred at rt for 48 hours before silica gel was added to quench the reaction. Solvent was evaporated and the resulting residue was purified via silica gel column chromatography to yield 5-chloro-2-methoxy-3-methyl-N-(6-(trifluoromethoxy)benzo[d]thiazol-2-yl)benzamide (60 mg, 31% yield) as a white solid. $^1$H NMR (300 MHz, Chloroform-d) δ 11.46 (s, 1H), 8.05 (d, J=2.8 Hz, 1H), 7.83 (d, J=8.9 Hz, 1H), 7.74 (dd, J=2.4, 1.1 Hz, 1H), 7.44 (d, J=2.8 Hz, 1H), 7.39-7.31 (m, 1H), 3.96 (s, 3H), 2.40 (s, 3H). MS (ESI) [M+H]+ requires m/z 417.03, found m/z 417.20.

A solution of 5-chloro-2-methoxy-3-methyl-N-(6-(trifluoromethoxy)benzo[d]thiazol-2-yl)benzamide (60 mg, 0.144 mmol) in DMF (3 ml) is mixed with Sodium ethanethiolate (60 mg, 0.721 mmol) and the resulting suspension is heated at 130° C. overnight. After completion of the reaction, 1N HCl was added to the reaction and extracted with EA for two times. The combined EA layer was dried over Na$_2$SO$_4$ and concentrated under reduced pressure. The residue was purified via silica gel column chromatography to give the title compound (47 mg, 83%) as a white solid. $^1$H NMR (300 MHz, Acetone-d$_6$) δ 11.37 (brs, 2H), 8.09 (d, J=2.6 Hz, 1H), 8.04 (s, 1H), 7.83 (d, J=8.8 Hz, 1H), 7.48 (d, J=8.8 Hz, 1H), 7.40 (d, J=2.6 Hz, 1H), 2.26 (s, 3H). MS (ESI) [M+H]$^+$ requires m/z 403.01, found m/z 403.20.

Example 52

5-Chloro-3-(3-(dimethylamino)propyl)-2-hydroxy-N-(6-(trifluoromethyl)benzo[d]thiazol-2-yl)benzamide (52)

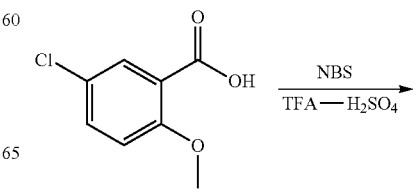

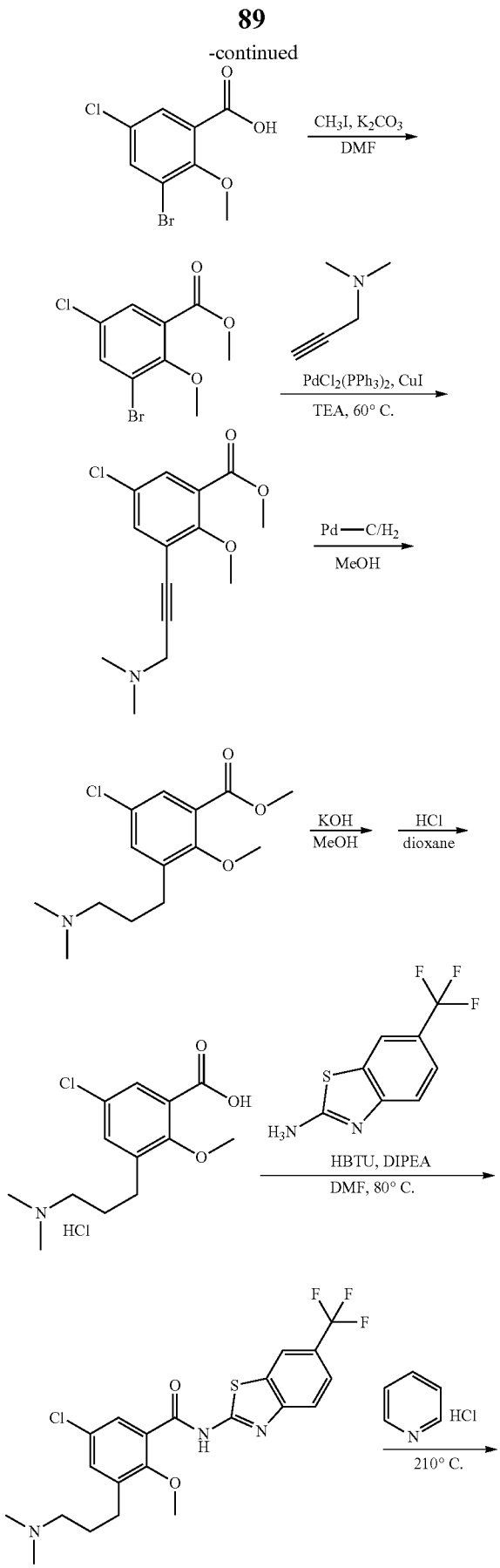

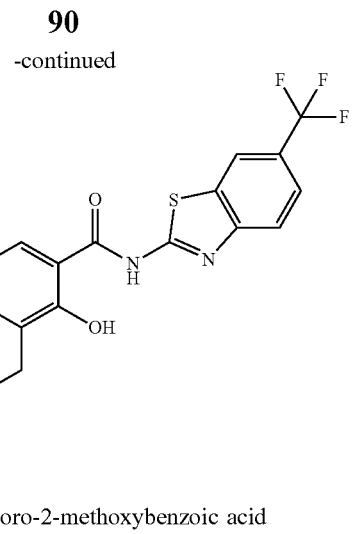

3-bromo-5-chloro-2-methoxybenzoic acid

To a stirred solution of 5-chloro-2-methoxybenzoic acid (5.58 g, 30 mmol) in sulfuric acid (10 ml) and TFA (20 ml) at rt was added NBS (5.88 g, 33 mmol). The pale solution was stirred at rt for 3 hs. The resulting pale suspension was carefully poured onto 500 g crushed ice. The mixture was extracted with EA. The EA layer dried over sodium sulfate and concentrated under reduced pressure. The light yellow residue was suspended in minimum DCM. The solid was collected, washed with cold DCM and dried under vacuum overnight to yield 3-bromo-5-chloro-2-methoxybenzoic acid (7 g, 89%) as a white solid. $^1$H NMR (300 MHz, acetone) δ 7.86 (d, 1H, J=3.0 Hz), 7.78 (d, 1H, J=3.0 Hz), 3.91 (s, 3H).

methyl 3-bromo-5-chloro-2-methoxybenzoate

To a stirred solution of 3-bromo-5-chloro-2-methoxybenzoic acid (6 g, 22.6 mmol) in DMF (30 ml) was added potassium carbonate (31 g, 226 mmol) and followed by CH$_3$I (1.4 ml, 22.6 mmol). The mixture was stirred at rt for 24 hs. Water was added and extracted with EA for two times. The combined organic layer was washed with water and brine and dried over sodium sulfate. The organic layer was filtered and the solvent removed in vacuo to yield a pale yellow oil (6.18 g, 97%).

methyl 5-chloro-3-(3-(dimethylamino)prop-1-yn-1-yl)-2-methoxybenzoate

Under N$_2$, a mixture of methyl 3-bromo-5-chloro-2-methoxybenzoate (1.02 g, 3.65 mmol), N,N-dimethylprop-2-yn-1-amine (1.19 ml, 10.94 mmol), PdCl$_2$(PPh$_3$)$_2$ (51 mg, 0.073 mmol), CuI (14 mg, 0.073 mmol) in triethylamine (15 ml) was heated at 60° C. overnight. Water was added and extracted with EA for two times. The combined organic layer was washed with water and brine and dried over sodium sulfate, concentrated in vacuo and the residue was purified via silica gel column chromatography to yield the title compound as a yellow oil (1.02 g, 100%). $^1$H NMR (300 MHz, CHCl$_3$) δ 7.67 (d, 1H, J=3.0 Hz), 7.50 (d, 1H, J=3.0 Hz), 3.96 (s, 3H), 3.90 (s, 3H), 3.54 (s, 2H), 2.38 (s, 6H). MS (ESI) [M+H]$^+$ requires m/z 282.09, found m/z 282.05.

methyl 5-chloro-3-(3-(dimethylamino)propyl)-2-methoxybenzoate

A mixture of methyl 5-chloro-3-(3-(dimethylamino)prop-1-yn-1-yl)-2-methoxybenzoate (1.02 g, 3.65 mmol) and Pd—C (200 mg) in methanol (20 ml) was stirred under H$_2$ at rt overnight. After completion of the reaction, the catalyst was filtered out and the filtrate was concentrated. The resulting residue was purified via silica gel column chromatography to yield the title compound as a yellow oil (556 mg, 55%). $^1$H NMR (300 MHz, CHCl$_3$) δ 7.64 (d, 1H, J=3.0 Hz), 7.34 (d, 1H, J=3.0 Hz), 3.93 (s, 3H), 3.83 (s, 3H), 2.68 (t, 2H, J=6.0 Hz), 2.37 (t, 2H, J=6.0 Hz), 2.28 (s, 6H), 1.85-1.75 (m, 2H). MS (ESI) [M+H]$^+$ requires m/z 286.1, found m/z 285.7.

5-chloro-3-(3-(dimethylamino)propyl)-2-methoxy-N-(6-(trifluoromethyl)benzo[d]thiazol-2-yl)benzamide To a stirred solution of methyl 5-chloro-3-(3-(dimethylamino)propyl)-2-methoxybenzoate (90 mg, 0.32 mmol) in MeOH (5 ml) was added 1.5 ml 1N KOH solution. The resulting mixture was stirred at rt overnight. The solvent was evaporated out and 4N HCl in dioxane (1 ml) was added to the residue. The mixture was stirred for another 10 min before it was concentrated and dried under vacuum. To this residue was added HBTU (144 mg, 0.38 mmol), DMF (3 ml) and DIPEA (275 ul, 1.58 mmol). The mixture was stirred for 10 mins and then 6 (trifluoromethyl)benzo[d]thiazol-2-amine (69 mg, 0.32 mmol) was added. The resulting reaction was heated at 80° C. for 24 hs. After cooled to rt, the mixture was separated between EA and water. The organic layer was washed with brine, dried over Na$_2$SO$_4$ and concentrated in vacuo. Purification by column chromatography gave the title compound as a pale yellow solid (50 mg, 34%). MS (ESI) [M+H]$^+$ requires m/z 472.1, found m/z 471.6.

5-Chloro-3-(3-(dimethylamino)propyl)-2-hydroxy-N-(6-(trifluoromethyl)benzo[d]thiazol-2-yl)benzamide (52)

5-chloro-3-(3-(dimethylamino)propyl)-2-methoxy-N-(6-(trifluoromethyl)benzo[d]thiazol-2-yl)benzamide (50 mg, 0.11 mmol) was mixed with pyridinium chloride (1.0 g). The mixture was heated to 210° C., stirred for 15 minutes and cooled down to rt. The resulting solid was dissolved in water and extracted with ethyl acetate. The organic layer was concentrated in vacuo and the residue was purified via silica gel column chromatography to yield the title compound MB5-3 as a pale yellow powder (15.0 mg, 30% yield). $^1$H NMR (300 MHz, methanol) δ 8.21 (s, 1H), 7.82-7.78 (m, 2H), 7.68 (d, 1H, J=3.0 Hz), 7.25 (d, 1H, J=3.0 Hz), 2.94 (t, 2H, J=6.0 Hz), 2.89 (s, 6H), 2.80 (t, 2H, J=6.0 Hz), 2.12-2.03 (m, 2H). MS (ESI) [M+H]$^+$ requires m/z 458.1, found m/z 458.2.

Example 53

5-Chloro-3-((dimethylamino)methyl)-2-hydroxy-N-(6-(trifluoromethyl)benzo[d]thiazol-2-yl)benzamide (53)

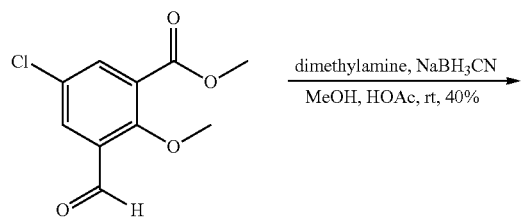

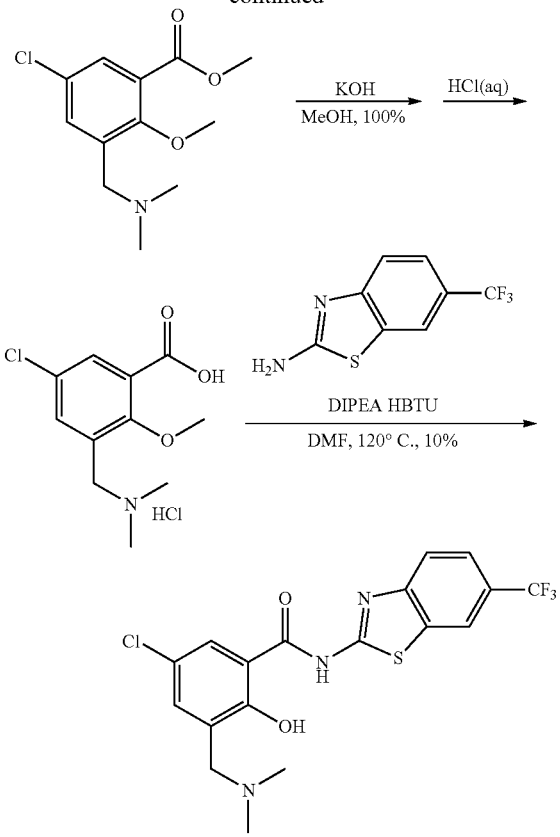

To a stirred solution of methyl 5-chloro-3-formyl-2-methoxybenzoate (210 mg, 0.921 mmol) in MeOH (5 ml) was added dimethylamine (0.921 ml, 2.0M in THF) followed by NaBH$_3$CN (116 mg, 1.842 mmol) and acetic acid (200 ul, 3.5 mmol). The resulting mixture was stirred at rt overnight. After the reaction completed, saturated sodium bicarbonate solution was added and the aqueous phase was extracted with EA two times. The combined organic layers were dried and purified via column chromatography to yield the title compound as a yellow oil (94 mg, 40%). MS (ESI) [M+H]$^+$ requires m/z 258.09, found m/z 257.40.

To a stirred solution of methyl 5-chloro-3-((dimethylamino)methyl)-2-methoxybenzoate (94 mg, 0.365 mmol) in MeOH (5 ml) was added 1.83 ml 1N KOH solution. The resulting mixture was stirred at 60° C. overnight. The solvent was evaporated out and 4N HCl in dioxane (1 ml) was added to the residue. The mixture was stirred for another 10 min before it was concentrated and dried under vacuum. To this residue was added HBTU (166 mg, 0.438 mmol), DMF (5 ml) and DIPEA (318 ul, 1.825 mmol). The mixture was stirred for 10 mins and then 6 (trifluoromethyl)benzo[d]thiazol-2-amine (80 mg, 0.365 mmol) was added. The resulting reaction was heated at 120° C. for 24 hs. After cooled to rt, the mixture was separated between EA and water. The organic layer was washed with brine, dried over Na$_2$SO$_4$ and concentrated in vacuo. Purification by column chromatography gave the title compound as a yellow solid (15 mg, 10%). $^1$H NMR (300 MHz, Chloroform-d) δ 8.13 (dd, J=4.3, 2.3 Hz, 2H), 7.87 (d, J=8.5 Hz, 1H), 7.68 (d, J=8.6 Hz, 1H), 7.18 (d, J=2.7 Hz, 1H), 3.94 (s, 2H), 2.60 (s, 6H). MS (ESI) [M+H]$^+$ requires m/z 430.06, found m/z 429.70.

Example 54

5-Chloro-3-((dimethylamino)methyl)-2-hydroxy-N-(6-(trifluoromethoxy)benzo[d]thiazol-2-yl)benzamide (54)

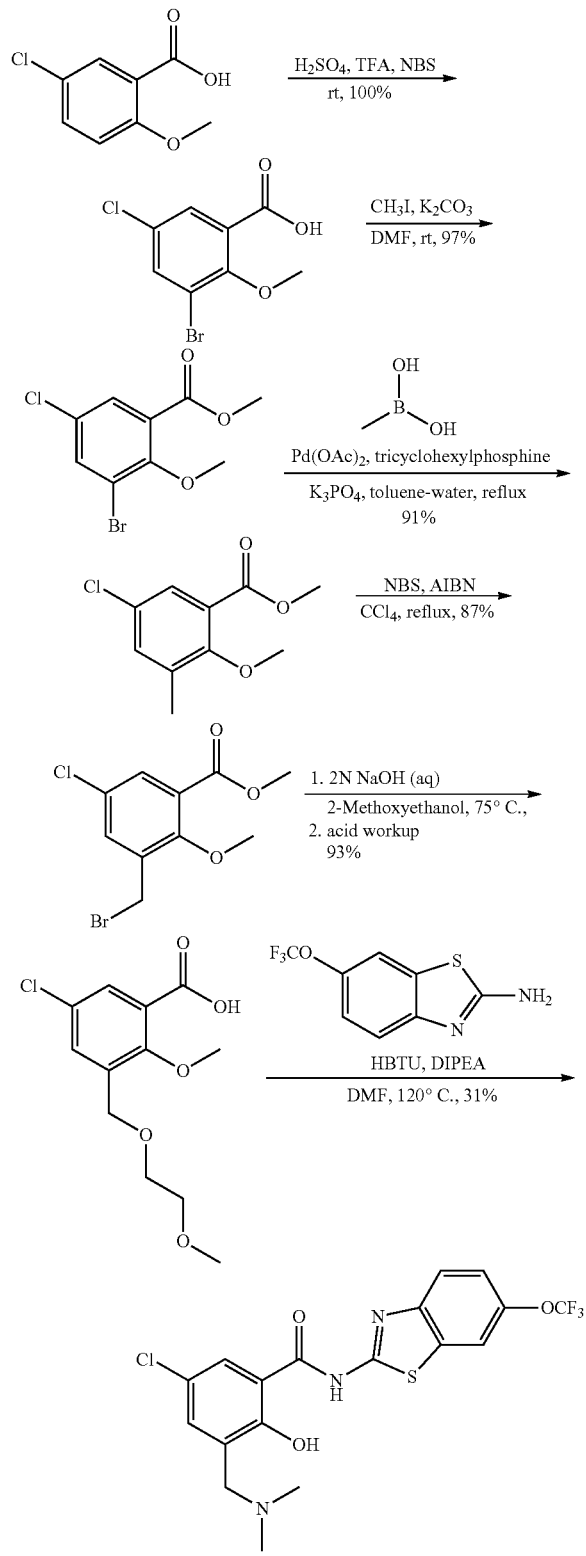

To a stirred solution of 5-Chloro-2-methoxybenzoic acid (5.59 g, 30 mmol) in sulfuric acid (10.2 ml) and TFA (20.4 ml) at rt was added NBS (5.87 g, 33 mmol). The pale solution was stirred at rt overnight. The resulting pale suspension was carefully poured onto crushed ice. The mixture was extracted with EA. The EA layer dried over Na2SO4 and concentrated under reduced pressure. The light yellow residue was suspend in minimum amount of DCM. The solid was collected, washed with cold DCM and dried under vacuum to yield the 3-bromo-5-chloro-2-methoxybenzoic acid as a white solid (8.00 g, 100%). $^1$H NMR (300 MHz, acetone) δ 7.86 (d, 1H, J=3.0 Hz), 7.78 (d, 1H, J=3.0 Hz), 3.91 (s, 3H).

To a stirred solution of 3-bromo-5-chloro-2-methoxybenzoic acid (6 g, 22.6 mmol) in DMF (30 ml) was added potassium carbonate (31 g, 226 mmol) and followed by CH$_3$I (1.4 ml, 22.6 mmol). The mixture was stirred at rt for 24 hs. Water was added and extracted with EA for two times. The combined organic layer was washed with water and brine and dried over sodium sulfate. The organic layer was filtered and the solvent removed in vacuo to yield a pale yellow oil (6.18 g, 97%).

A mixture of methyl 3-bromo-5-chloro-2-methoxybenzoate (756 mg, 2.7 mmol), methylboronic acid (324 mg, 5.4 mmol), Pd(OAc)$_2$ (24 mg, 0.11 mmol), tricyclohexylphosphine (68 mg, 0.24 mmol) and potassium phosphate tribasic (1.9 g, 8.96 mmol) was refluxed in toluene (10 ml) and water (1 ml) under N$_2$ overnight. After the reaction was cooled, saturated NH4Cl solution was added and extracted with EA for two times. The combined EA layer was dried over Na2SO4 and concentrated under reduced pressure. The residue was purified via silica gel column chromatography to give methyl 5-chloro-2-methoxy-3-methylbenzoate (520 mg, 91%) as a yellow oil. $^1$H NMR (300 MHz, chloroform) δ 7.62 (d, 1H, J=3.0 Hz), 7.32 (d, 1H, J=3.0 Hz), 3.92 (s, 3H), 3.82 (s, 3H), 2.30 (s, 3H).

To a flame dried flask was added NBS (183 mg, 1.03 mmol), AIBN (15 mg, 0.093 mmol) and a solution of methyl 5-chloro-2-methoxy-3-methylbenzoate (201 g, 0.93 mmol) in CCl4 (10 ml). The suspension was refluxed in the dark overnight. The mixture was cooled to rt and concentrated. The residue was purified via silica gel column chromatography to give methyl 5-chloro-3-(bromomethyl)-2-methoxybenzoate as a colorless oil (236 mg, 87%). $^1$H NMR (300 MHz, cdcl3) δ 7.76 (d, J=2.7 Hz, 1H), 7.54 (d, J=2.7 Hz, 1H), 4.51 (s, 2H), 3.96 (s, 3H), 3.94 (s, 3H).

To a stirred solution of methyl 5-chloro-3-(bromomethyl)-2-methoxybenzoate (236 mg, 0.805 mmol) in 2-methoxyethanol (10 ml) was added 2N NaOH solution (7 ml). The resulting mixture was stirred at 75° C. overnight and then concentrated in vacuo. The residue was dissolved in EA and the resulting solution was washed with 2N HCl dried over sodium sulfate and concentrated in vacuo. The residue was triturated with ether to give 5-chloro-2-methoxy-3-((2-methoxyethoxy)methyl)benzoic acid (204 mg, 93%) as yellow oil. $^1$H NMR (300 MHz, cdcl3) δ 10.02 (brs, 1H), 7.86 (d, J=2.8 Hz, 1H), 7.66 (d, J=1.4 Hz, 1H), 4.62 (s, 2H), 3.87 (s, 3H), 3.75-3.67 (m, 2H), 3.66-3.56 (m, 2H), 3.41 (s, 3H). MS (ESI) [M+Na]$^+$ requires m/z 297.05, found m/z 296.6.

5-chloro-2-methoxy-3-((2-methoxyethoxy)methyl)benzoic acid (170 mg, 0.62 mmol) was dissolved in DMF (5 ml). HBTU (280 mg, 0.74 mmol) was added followed by DIPEA (540 ul, 3.1 mmol). The resulting mixture was stirred at rt for 15 mins, then 6-(trifluoromethoxy)benzo[d]thiazol-2-amine (145 mg, 0.62 mmol) was added. The resulting mixture was stirred at 120° C. for 24 h. Water was added and extracted with EA for two times. The combined EA layer was dried over Na$_2$SO$_4$ and concentrated under reduced pressure. The residue was purified via silica gel column chromatography to give title compound as a yellow powder (80 mg, 31%). $^1$H NMR (300 MHz, Acetone-d6) δ 7.99 (s, 1H), 7.93 (d, J=3.1 Hz, 1H), 7.81 (d, J=8.7 Hz, 1H), 7.40 (d, J=8.8 Hz, 1H), 7.22 (d, J=3.0 Hz, 1H), 4.35 (s, 2H), 3.04 (s, 6H). MS (ESI) [M+H]$^+$ requires m/z 446.06, found m/z 446.10.

Example 55

55-Chloro-2-hydroxy-3-methyl-N-(6-(methylsulfonyl)benzo[d]thiazol-2-yl)benzamide (55)

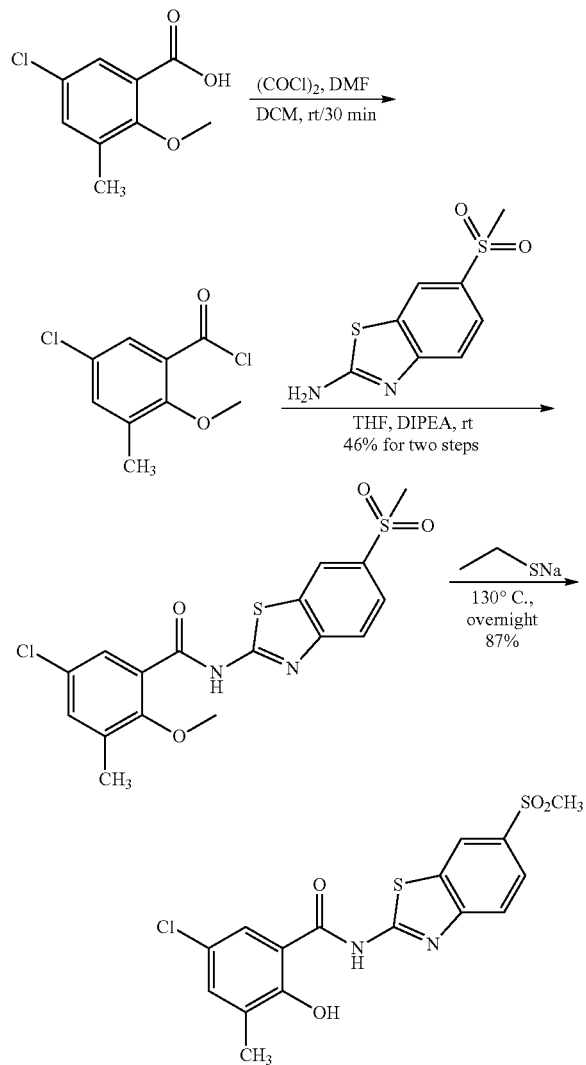

5-chloro-2-methoxy-3-methylbenzoic acid (100 mg, 0.5 mmol) was dissolved in DCM (3.0 mL), followed by the addition of catalytic amount of DMF (1 drop) and oxalyl chloride (52 uL, 0.6 mmol) respectively. The reaction was allowed to stir at rt for 30 min and concentrated in vacuo. The residue was re-dissolved in THF (5.0 mL), and Hunig's base (105 uL, 0.6 mmol) and 6-(methyl sulfonyl)benzo[d]thiazol-2-amine (92 mg, 0.4 mmol) were added. The mixture was stirred at rt for 48 hours before silica gel was added to quench the reaction. Solvent was evaporated and the resulting residue was purified via silica gel column chromatography to yield 5-chloro-2-methoxy-3-methyl-N-(6-(methylsulfonyl)benzo[d]thiazol-2-yl)benzamide (75 mg, 46% yield) as a white solid. H NMR (500 MHz, cdcl3) δ 11.44 (s, 1H), 8.48 (d, J=1.7 Hz, 1H), 8.06-8.02 (m, 1H), 8.00 (dd, J=8.5, 1.9 Hz, 1H), 7.94 (d, J=8.5 Hz, 1H), 7.45 (dd, J=2.7, 0.7 Hz, 1H), 3.95 (s, 3H), 3.13 (s, 3H), 2.40 (s, 3H). MS (ESI) [M+H]$^+$ requires m/z 411.02, found m/z 411.20.

A solution of 5-chloro-2-methoxy-3-methyl-N-(6-(methylsulfonyl)benzo[d]thiazol-2-yl)benzamide (75 mg, 0.183 mmol) in DMF (5 ml) is mixed with Sodium ethanethiolate (77 mg, 0.915 mmol) and the resulting suspension is heated at 130° C. overnight. After completion of the reaction, 1N HCl was added to the reaction and extracted with EA for two times. The combined EA layer was dried over Na$_2$SO$_4$ and concentrated under reduced pressure. The residue was purified via silica gel column chromatography to give the title compound (62 mg, 87%) as a white solid. $^1$H NMR (400 MHz, DMSO-d6) δ 8.64 (d, J=1.9 Hz, 1H), 7.99 (dd, J=8.5, 1.9 Hz, 1H), 7.97-7.90 (m, 1H), 7.86 (d, J=8.5 Hz, 1H), 7.45 (d, J=2.7 Hz, 1H), 3.25 (s, 3H), 2.21 (s, 3H). MS (ESI) [M+H]$^+$ requires m/z 397.01, found m/z 397.20.

Example 56

5-Chloro-2-methyl-N-(6-(trifluoromethyl)benzo[d]thiazol-2-yl)-1H-benzo[d]imidazole-7-carboxamide (56)

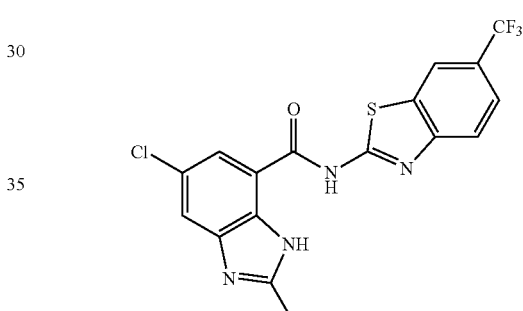

$^1$H NMR (400 MHz, DMSO-d$_6$) δ 13.58 (brs, 1H), 13.28 (brs, 1H), 8.55 (s, 1H), 8.00-7.91 (m, 3H), 7.78 (d, J=8.8 Hz, 1H), 2.68 (s, 3H). MS (ESI) [M+H]$^+$ requires m/z 411.03, found m/z. 411.4.

Compound 57

5-Chloro-2-ethyl-N-(6-(trifluoromethyl)benzo[d]thiazol-2-yl)-1H-benzo[d]imidazole-7-carboxamide

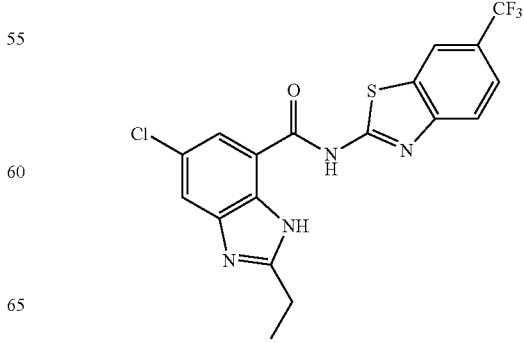

¹H NMR (400 MHz, DMSO-d₆) δ 13.74 (brs, 1H), 13.26 (brs, 1H), 8.02 (d, J=8.8 Hz, 1H), 7.92 (s, 2H), 7.79 (d, J=9.2 Hz, 1H), 3.05 (q, J=7.6 Hz, 2H), 1.45 (t, J=8.0 Hz, 3H). MS (ESI) [M+H]⁺ requires m/z 425.05, found m/z. 425.4.

Example 58

5-Chloro-N-(6-(trifluoromethyl)benzo[d]thiazol-2-yl)-1H-benzo[d][1,2,3]triazole-7-carboxamide (58)

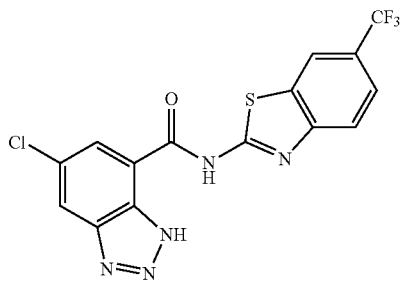 [SMILES: O=C(Nc1nc2ccc(C(F)(F)F)cc2s1)c1cc(Cl)cc2nn[nH]c12]

¹H NMR (400 MHz, DMSO-d₆) δ 14.77 (brs, 1H), 8.57 (s, 1H), 8.42 (s, 1H), 8.32 (s, 1H), 7.98 (d, J=8.8 Hz, 1H), 7.80 (d, J=8.0 Hz, 1H). MS (ESI) [M−H]⁻ requires m/z 395.99, found m/z. 396.4.

Example 59

5-Chloro-N-(4,6-difluorobenzo[d]thiazol-2-yl)-1H-benzo[d][1,2,3]triazole-7-carboxamide

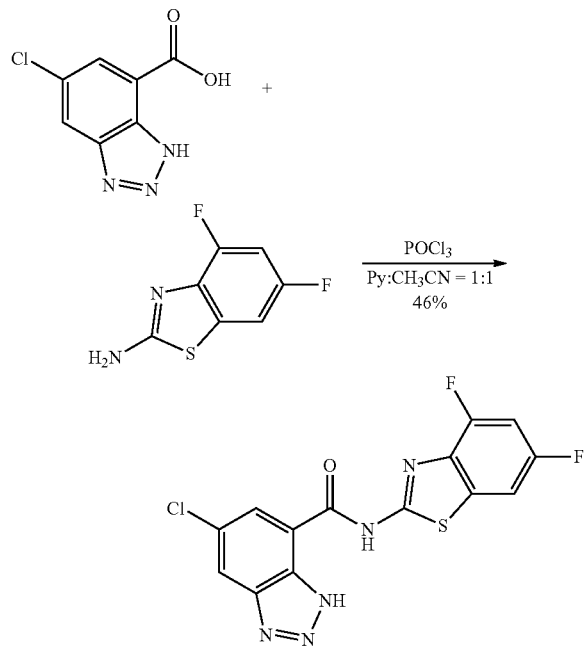

At 0° C., to a stirred solution of 5-chloro-1H-benzo[d][1,2,3]triazole-7-carboxylic acid (29 mg, 0.15 mmol) and 4,6-difluorobenzo[d]thiazol-2-amine (28 mg, 0.15 mmol) in pyridine (2 ml) and acetonitrile (2 ml) was added POCl₃ (42 ul, 0.45 mmol). The reaction mixture was stirred at rt overnight. The mixture was separated between EA and water. The organic layer was washed with brine, dried over Na₂SO₄ and concentrated in vacuo. Purification by column chromatography gave the title compound as a yellow solid (25 mg, 46%). H NMR (300 MHz, Acetone-d6) δ 8.39-8.37 (m, 2H), 7.77-7.74 (m, 1H), 7.27-7.20 (m, 1H). MS (ESI) [M+Na]⁺ requires m/z 387.98, found m/z 387.30.

Compound 60

5-Chloro-N-(6-fluorobenzo[d]thiazol-2-yl)-1H-benzo[d][1,2,3]triazole-7-carboxamide

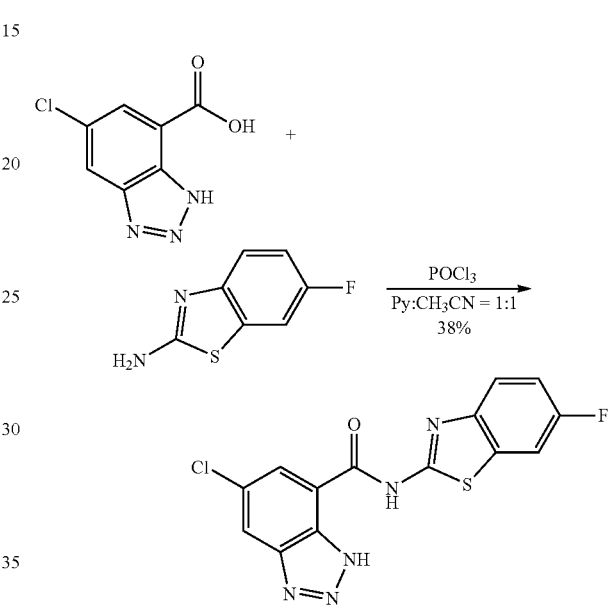

At 0° C., to a stirred solution of 5-chloro-1H-benzo[d][1,2,3]triazole-7-carboxylic acid (29 mg, 0.15 mmol) and 6-fluorobenzo[d]thiazol-2-amine (25 mg, 0.15 mmol) in pyridine (2 ml) and acetonitrile (2 ml) was added POCl₃ (42 ul, 0.45 mmol). The reaction mixture was stirred at rt overnight. The mixture was separated between EA and water. The organic layer was washed with brine, dried over Na₂SO₄ and concentrated in vacuo. Purification by column chromatography gave the title compound as a yellow solid (20 mg, 38%). H NMR (300 MHz, Acetone-d6) δ 8.50 (brs, 2H), 7.98-7.95 (m, 1H), 7.82 (brs, 1H), 7.37-7.32 (m, 1H). MS (ESI) [M+Na]⁺ requires m/z 369.99, found m/z 369.45.

Mitochondrial Uncoupling Activity Assays

Example 61

Oxygen Consumption Assay with Seahorse XF96 or Seahorse XF24 Instruments

By definition, mitochondrial uncoupling is the decoupling of mitochondrial electron transport chain activity (mitochondrial oxidation) from ATP synthesis by mitochondrial ATP synthase. Technically, mitochondrial uncoupling activity is defined by the ability of a chemical compound to induce oxygen consumption of cells or isolated mitochondria in the presence of a mitochondrial ATP synthase inhibitor such as oligomycin. Accordingly, we determined mitochondrial uncoupling activity by oxygen consumption rate (OCR) assay with a Seahorse XF96 or a Seahorse XF24 instrument following the vendor's instruction, using mouse myoblast C2C12 cells growing in medium containing 10% fetal bovine serum. OCR was measured first under normal growth condition; then OCR was measured after treatment with oligomycin (final concentration 2.5 µM); then OCR was measured after both oligomycin and the synthesized compound at varying concentrations were added. FIG. 1 shows a typical profile of Seahorse OCR assay with a mitochondrial uncoupler. The minimal concentration (Cmin) of each compound under which OCR is induced in the presence of oligomycin, was determined. The following table (Table I) summarizes the mitochondrial activity of compounds.

TABLE I

Mitochondrial Uncoupling Activity Summary, categorized by Cmin (minimal concentration to induce ATP synthase- independent OCR increase)

| Compound Number | Activities[1] |
|---|---|
| 1 | *** |
| 2 | *** |
| 3 | *** |
| 8 | ** |
| 9 | * |
| 14 | *** |
| 15 | *** |
| 13 | *** |
| 14 | *** |
| 15 | *** |
| 16 | *** |
| 17 | *** |
| 21 | *** |
| 22 | *** |
| 23 | *** |
| 24 | *** |
| 25 | * |
| 26 | * |
| 27 | *** |
| 28 | *** |
| 29 | *** |
| 31 | *** |
| 32 | *** |
| 33 | *** |
| 34 | *** |
| 35 | *** |
| 36 | *** |
| 37 | *** |
| 38 | *** |
| 40 | *** |
| 41 | *** |
| 42 | * |
| 49 | * |
| 50 | *** |
| 51 | *** |
| 52 | *** |
| 53 | *** |
| 54 | *** |
| 56 | *** |
| 57 | * |
| 58 | * |
| 59 | * |
| 60 | * |

[1]Minimal concentration induce ATP synthase independent OCR:
*** <10 µM;
** ≥10 but ≤25 µM;
* >25 µM.

Example 62

Mitochondrial Membrane Potential Assay

Mitochondrial uncoupling may also lead to a reduction of mitochondrial membrane potential. We performed mitochondrial membrane potential assay using TMRE (tetramethylrhodamine ethyl ester) staining method with cultured mammalian cells, the NIH-3T3 cells, or HepG2 cells. Cells were seeded onto 6-well plates and cultured in DMEM medium supplemented with 10% fetal bovine serum and 2 mM glutamine. Cells were allowed to grow to logarithmic growth phase prior to experiments. The cells were treated with each individual compound at various concentrations for two hours, followed by staining with TMRE at final concentration of 100 nM for 15 minutes. The cells were then washed once with PBS, and examined under fluorescence microscopy. Cells treated with various concentrations of niclosamide ethanolamine were used as positive control. Reduction of mitochondrial TMRE staining was estimated as a quantification of mitochondrial uncoupling activity. $EC_{50}$ of an indicated compound is defined as the concentration at which the fluorescent intensity of mitochondrial TMRE staining in cells is reduced to about 50%. The following table (Table II) summarizes the activity of individual compounds in reducing mitochondrial membrane potential in cultured mammalian cells.

TABLE II

Relative activity on mitochondrial membrane potential reduction

| Compound Number | Activities[2] | Compound Number | Activities[2] |
|---|---|---|---|
| 1 | *** | 23 | *** |
| 8 | ** | 29 | *** |
| 9 | * | 31 | *** |
| 14 | *** | 32 | *** |
| 15 | *** | 33 | *** |
| 13 | *** | 34 | *** |
| 14 | *** | 35 | *** |
| 15 | *** | 36 | *** |
| 16 | *** | 37 | *** |
| 17 | *** | 38 | *** |
| 21 | *** | 40 | *** |
| 22 | *** | 41 | *** |
| 23 | *** | 42 | * |
| 24 | *** | 49 | * |
| 25 | * | 50 | *** |
| 26 | * | 51 | *** |
| 27 | *** | 58 | * |
| 28 | *** | | |

[2]EC50:
*** <10 µM;
** ≥10 but ≤25 µM;
* >25 µM.

Example 63

Figures 2A, 2B:
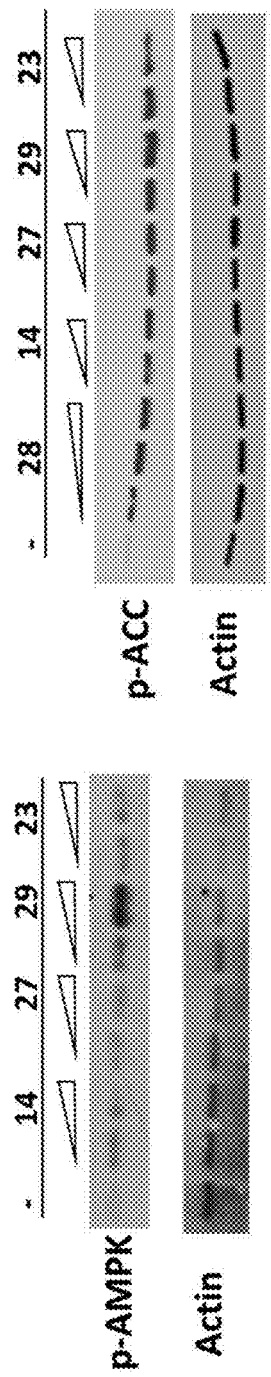
FIGS. 2A-2B show increase in phosphorylated AMPK (FIG. 2A, activation) and in phosphorylated ACC (inhibition of activity, FIG. 2B) upon treatment of indicated example compounds at concentrations that are efficacious for mitochondrial uncoupling.

AMPK (AMPK-Activated Kinase) Activation Assay and ACC (Acetyl-CoA Carboxylase) Inhibition Assay Mitochondrial uncoupling leads to a reduction in cell bioenergetic efficiency, usually leading to a slight decrease in ATP and an increase in AMP. Elevation of intracellular AMP activates AMPK. In cells where ACC is expressed such as liver cells, AMPK could in turn phosphorylate (inhibit) ACC. ACC is a master regulator of lipid metabolism. Inhibition of ACC inhibits lipid de novo synthesis and promotes fatty acid beta-oxidation. We measured AMPK activation (phosphorylated AMPK level) and ACC inhibition (phosphorylated ACC level) in fibroblast NIH3T3 cells and in liver HepG2 cells, respectively, by immunoblotting assay with antibody against p-AMPK and p-ACC, respectively (the Phospho-AMPKα (Thr172) mAb (#2535), Phospho-acetyl-CoA carboxylase (Ser79) antibody (#3661) are from Cell Signaling Technology). Cells were treated with varying concentrations of compounds for 3-6 hrs. Cell extracts were then obtained and subjected to sodium dodecyl sulfate-polyacrylamide gel electrophoresis (SDS-PAGE). Proteins were transferred to polyvinylidene difluoride (PVDF) membranes (Millipore, IPVH00010). Immunoblotting assays were performed with antibodies. FIGS. 2A-2B show increase in phosphorylated AMPK (FIG. 2A, activation) and in phosphorylated ACC (inhibition of activity, FIG. 2B) upon treatment of indicated example compounds at concentrations that are efficacious for mitochondrial uncoupling.

Example 64

Figure 3A:
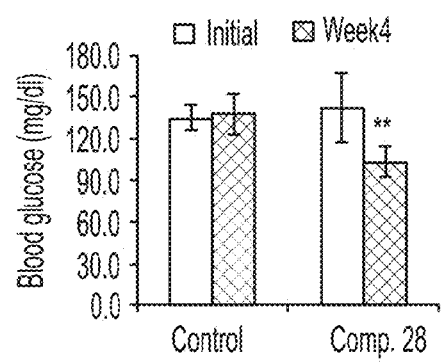
FIGS. 3A-3D show the effect of an example compound (Compound 28) on blood glucose (FIG. 3A), plasma insulin (FIG. 3B), insulin tolerance (FIG. 3C), and fatty liver weight caused by high fat diet (FIG. 3D).
Figure 3B:
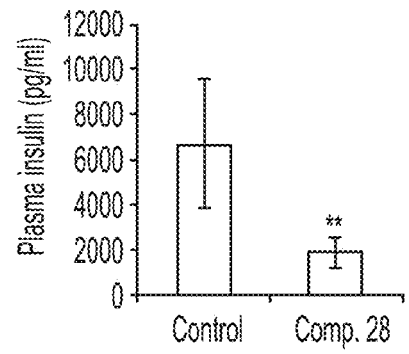
Figure 3C:
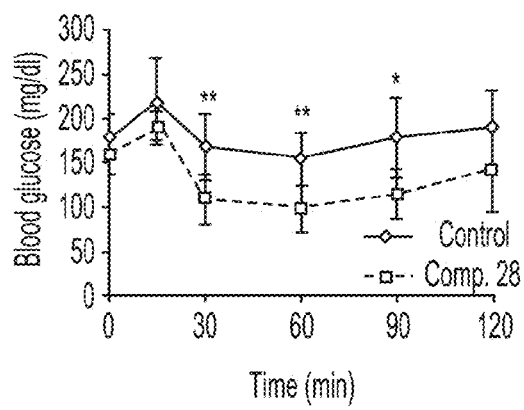
Figure 3D:
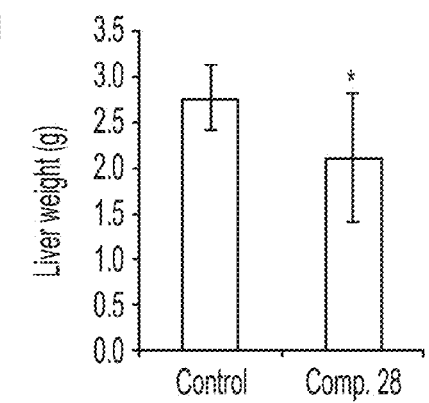
Figures 4A, 4B:
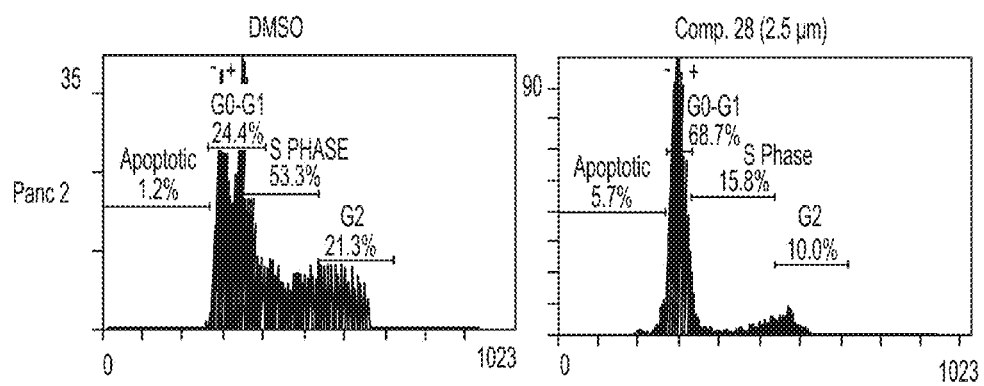
FIGS. 4A-4D show the effect of an example compound (Compound 28) on cell cycle progression. Panc 2 (FIGS. 4A and 4B) or Panc 1 (FIGS. 4C and 4D) cells were treated with compound 28 (2.5 µM) for 48 hrs, and cell cycle profiles were determined by flow cytometry.
Figures 4C, 4D:
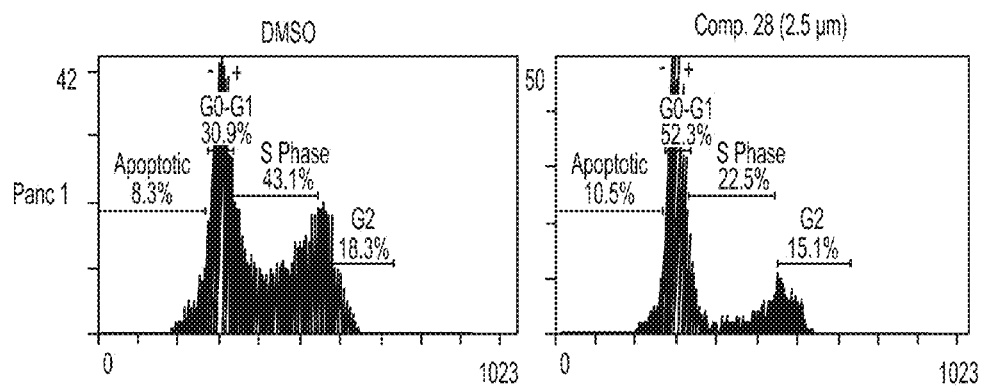

Efficacy on Type 2 Diabetes and Fatty Liver In Vivo: the Effect in Reducing Blood Glucose, Reducing Blood Insulin, Reducing in Insulin Tolerance, and Reduction in Fatty Liver in High-Fat Diet (HFD)-Induced Diabetic Mouse Model To test the efficacy of compounds in treating type 2 diabetes in vivo, we used Compound 28 as an example, and determined its effect in reducing blood glucose, reducing blood insulin concentration, improving insulin sensitivity and reducing fatty liver in a clinically relevant mouse model, the HFD-induced fatty liver and diabetic model. C57B6/J male mice were fed HFD (60% calorie from fat) for 4 months, starting at age of 2 months, to induce high blood glucose, high blood insulin, and insulin tolerance symptoms of type 2 diabetes as well as fatty liver. The mice then either continued with HFD or with HFD containing 600 ppm Compound 28. Blood glucose, blood insulin levels were measured and glucose tolerance assay was performed to measure insulin sensitivity. The mice were sacrificed and the effect of Compound 28 on fatty liver development was evaluated by comparing the liver weight. FIGS. 3A-C show that the treatment with Compound 28 markedly reduced blood glucose concentration, blood insulin concentration, and improves insulin sensitivity. FIG. 3D shows that Compound 28 reduced fatty liver weight caused by high fat diet. The plasma Compound 28 concentration was measured, and the levels were at an efficacious concentration that uncouples mitochondria.

Example 65

Effect on Cancer Cell Growth Inhibition

The effect of example compounds on cancer cell growth was evaluated. The cell growth inhibition assays were performed using a protocol standardized by National Cancer Institute (NCI) for evaluating anti-cancer drugs (https://dtp.cancer.gov/discovery_development/nci-60/methodology.htm). Human colon cancer HCT116 cell line and human lung cancer cell line H1299 were used for the assays. The human tumor cells were inoculated into 96 well microtiter plates. After cell inoculation, the microtiter plates were incubated for cell growth for 24 h prior to addition of compounds. After 24 h, two plates of each cell line were fixed in situ with TCA, to represent a measurement of the cell population for each cell line at the time of compound addition (Tz). Test compounds were solubilized in dimethyl sulfoxide, At the time of test compound addition, five 10-fold or ½ log serial dilutions were made to provide a total of five test compound concentrations plus control. Aliquots of 100 µl of these different test compound dilutions were added to the appropriate microtiter wells already containing 100 µl of medium, resulting in the required final test compound concentrations. Following test compound addition, the plates were incubated for an additional 48 h. The assay was terminated by the addition of cold TCA, Cells were fixed in situ with 50 µl of cold 50% (w/v) TCA (final concentration, 10% TCA), washed five times with tap water and air dried. Sulforhodamine B (SRB) solution (100 ul) at 0.4% (w/v) in 1% acetic acid was added to each well, and plates were incubated for 10 minutes at room temperature. After staining, unbound dye was removed by washing five times with 1% acetic acid and the plates were air dried. Bound stain was subsequently solubilized with 10 mM trizma base, and the absorbance was read on an automated plate reader at a wavelength of 515 nm. Using the seven absorbance measurements [time zero, (Tz), control growth, (C), and test growth in the presence of compound at the five concentration levels (Ti)], the percentage growth was calculated at each of the test compound concentrations levels. Growth inhibition of 50% (GI50) was calculated from [(Ti−Tz)/(C−Tz)]×100=50, which is the test compound concentration resulting in a 50% reduction in the net protein increase (as measured by SRB staining) in control cells during the compound incubation. Consistent results were obtained with both HCT116 cells and H1299 cells. Table III shows the $GI_{50}$ of the tested example compounds.

TABLE III

Cell growth inhibition activity of example compounds

| Compound Code | Activities[3] |
|---|---|
| 1 | *** |
| 23 | *** |
| 24 | *** |
| 27 | *** |
| 28 | *** |
| 29 | *** |
| 31 | *** |
| 38 | *** |
| 40 | *** |

[3]$GI_{50}$, 50% growth inhibition activity:
*** <10 µM;
** ≥10 but ≤25 µM;
* >25 µM.

Example 66

Effect on Cancer Cell Cycle Progression and on Clonogenicity of Cancer Cells

The effect of example compounds on cell cycle progression was analyzed. The tumor cells, mouse pancreatic cancer cell Panc 2 cells, or human pancreatic cancer Panc 1 cells, were treated with the individual compounds at concentrations that were efficacious for mitochondrial uncoupling for 48 h, whereas the control group was treated with vehicle DMSO. Cells were then fixed with ice-cold 70% ethanol on ice for 30 minutes. After that, 5 µl of propidium iodide (PI) (Sigma, P 4170, 1 mg/ml) solution and 50 µl of RNAse A (Sigma, R-4875) solutions were added to the fixed cells, which were then kept for 30 minutes in the dark at room temperature. The cell cycle profile of the cells was analyzed by flow cytometry. As shown in FIGS. 4A-4D, the example Compound 28 arrested cancer cells at G0/G1 phase. Table IV below summarizes the activity of other example compounds on inducing G0/G1 cell cycle arrest.

The impact of example compounds on clonogenicity was analyzed. Cancer cells were plated in 6-well plates at 200 cells per well. Cells were treated with individual compounds at various concentrations. Cells were maintained with changes of the medium plus compounds for 10 days. The colonies were then fixed in 1:3 Acetic acid—Methanol solution for 5 minutes, stained with 0.02% crystal violet for 20 minutes and counted. Table V shows that example compounds reduced clonogenicity of cancer cells at concentrations where the compounds uncouple mitochondria.

TABLE IV

Cell Cycle Arresting (G0/G1 arrest) Activity of example compounds

| Compound Code | Activities[4] |
|---|---|
| 1 | *** |
| 27 | *** |
| 28 | *** |
| 38 | *** |

[4]effective concentration that can arrest cell cycle at G0/G1 phase
*** <10 µM;
** ≥10 but ≤25 µM;
* >25 µM.

TABLE V

Clonogenicity inhibition activity of example compounds

| Compound Code | Activities[5] |
|---|---|
| 1 | *** |
| 27 | *** |
| 28 | *** |
| 29 | *** |
| 38 | *** |

[5]IC$_{95}$, Concentration that reduces clonogenicity by 95%:
*** <10 µM;
** ≥10 but ≤25 µM;
* >25 µM.

Example 67

Figure 6A:
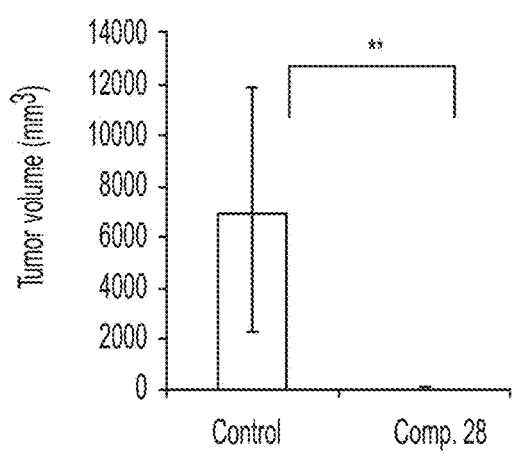
FIGS. 6A-6B show the quantification of the effect of the test compound (Compound 28) on hepatic metastasis of pancreatic cancer. Tumor volume (FIG. 6A) and number (FIG. 6B) were measured and compared. , P<0.01; *, P<0.001; n=6 each group, student t-test.
Figure 6B:
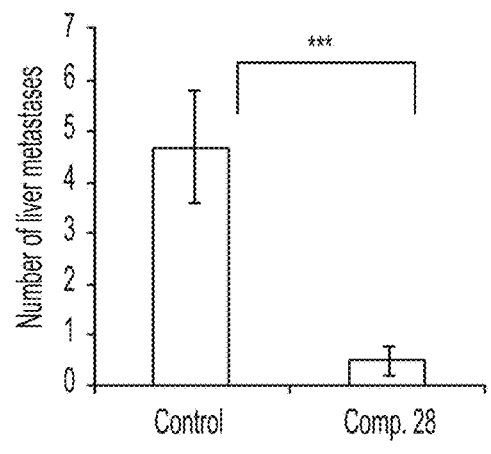

Efficacy on Metastatic Cancer: Effect on Metastasis of Pancreatic Cancer in Mouse Model The in vivo anti-cancer efficacy of an example compound, Compound 28, was examined using a well-established hepatic metastasis of pancreatic cancer mouse model. The mouse pancreatic cancer cells, Panc 2 cells (0.25 million cells), were injected into the spleen of immune compromised NOD-scid mice. The mice were randomized to two groups (n=6 each group), one group was fed normal chow, the second group was fed chow containing 750 ppm Compound 28. Three weeks later, mice were sacrificed and the hepatic metastasis of the pancreatic cancer was observed (FIGS. 5A-5B) and quantified (FIGS. 6A-6B) in control and Compound 28 treated mice. As shown in FIG. 5A, the untreated mice had massive hepatic tumor metastasis. In contrast, shown in FIG. 5B, the Compound 28 treated mice showed little or no hepatic tumor metastasis. The anti-tumor efficacy was quantified in FIGS. 6A-6B, treatment with Compound 28 dramatically reduced both the number of metastatic tumor nodules as well as metastatic tumor volume, demonstrating that Compound 28 has excellent anti-cancer activity in vivo. Importantly, the blood plasma concentrations of Compound 28 under the treatment dosage regimen was measured, which are in the range of efficacious concentration for uncoupling mitochondria.

Example 68

Anti-Bacterial Activities

Mitochondria are ancient bacteria that formed a symbiotic relationship with host cells. Bacterial plasma membrane contains electron transport chain and ATP synthase that are similar to those of mitochondria. Example compounds were tested for antibiotic activity. Tests to determine minimum inhibitory concentration (MIC) were performed. The test compounds and reference compounds were dissolved in DMSO to prepare the stock solutions (6.4 or 3.2 mg/ml), serial 2-fold compound dilutions were prepared at 100-fold of the final concentrations in a V-bottomed 96-well plate, total 11 dilutions ranging from 6.4 or 3.2 mg/ml to 0.0625 mg/ml. Aliquots of 2 µl 100× working solutions were transferred to column 1 to column 11 of the round-bottomed 96-well plate, and 2 µl DMSO to column 12 (as mock control). The prepared microdilution plate was used for the MIC test.

To prepare the inoculum, the strains were streaked out on corresponding agar plates one day before testing. For aerobic bacteria, the inoculum was prepared by picking a few colonies from a 24-hour-old subculture from the agar plate into sterile saline. The saline culture suspension was adjusted to the required turbidity followed by diluting in corresponding medium to obtain the final inoculum, i.e. ~1×10$^6$ CFU/ml for aerobic/anaerobic bacteria. Aliquots of 100 µl of the final inoculum were transferred to the microdilution plates as prepared as described above, which were pre-filled with 98 µl of the bacterial growth medium. MIC determination: The resulting plates were incubated at 37° C. for 20-24 hours (incubation temperature and time may be different according to the standard methods). MIC was recorded as the lowest concentration that completely or significantly inhibited the bacterial growth by visual inspection (FIG. 7).

Although the present disclosure has been described in considerable detail with reference to certain preferred versions thereof, other versions are possible. Therefore, the spirit and scope of the present disclosure should not be limited to the description of the preferred versions described herein.

Although compositions, materials, and methods similar or equivalent to those described herein can be used in the practice or testing of the present invention, suitable preparations, methods and materials are described herein. All publications mentioned herein are incorporated by reference in their entirety. In the case of conflict, the present specification, including definitions will control. In addition, the particular embodiments discussed below are illustrative only and not intended to be limiting.

All features disclosed in the specification, including the abstract and drawings, and all the steps in any method or process disclosed, may be combined in any combination, except combinations where at least some of such features and/or steps are mutually exclusive. Each feature disclosed in the specification, including abstract and drawings, can be replaced by alternative features serving the same, equivalent or similar purpose, unless expressly stated otherwise. Thus, unless expressly stated otherwise, each feature disclosed is one example only of a generic series of equivalent or similar features. Various modifications of the present disclosure, in addition to those described herein, will be apparent to those skilled in the art from the foregoing description. Such modifications are also intended to fall within the scope of the appended claims.

What is claimed is:

1. A compound of formula (I):

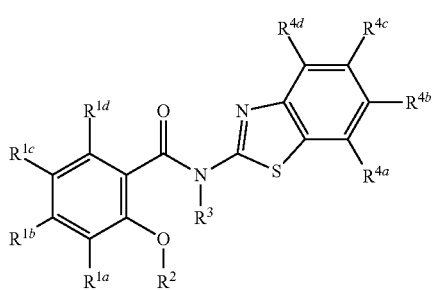

(I)

or a pharmaceutically acceptable salt, solvate, or prodrug thereof,
wherein:
  $R^{1a}$ is selected from the group consisting of hydrogen; optionally substituted $C_1$-$C_6$ alkyl; optionally substituted $C_2$-$C_6$ alkenyl; optionally substituted $C_2$-$C_6$ alkynyl; optionally substituted $C_3$-$C_{10}$ cycloalkyl; optionally substituted $C_3$-$C_{10}$ heterocyclyl; optionally substituted $C_3$-$C_{10}$ aryl; optionally substituted $C_3$-$C_{10}$ heteroaryl; $C_1$-$C_6$ perfluoroalkyl; halo; cyano; nitro; optionally substituted amino; —C(O)NHR$^5$; —C(O)NR$^5$R$^6$; —C(O)H; —C(O)R$^7$; —C(O)OH; and —C(O)OR$^5$;
  $R^{1b}$ and $R^{1d}$ at each instance are independently selected from the group consisting of: hydrogen; $C_1$-$C_6$ perfluoroalkyl; and halo;
  $R^{1c}$ is chloro;
  $R^2$ is selected from the group consisting of hydrogen; mono-saccharide; di-saccharide; C(O)NR$^5$R$^6$; and C(O)R$^7$; wherein the mono-saccharides and di-saccharide are attached to the phenolic oxygen at the anomeric center to form a glycosidic bond;
  $R^3$ is hydrogen, or alternatively, $R^2$ and $R^3$ taken together are a carbonyl group and together with the atoms to which they are attached, form a six-membered heterocyclic carbamate;
  $R^{4a}$, $R^{4b}$, $R^{4c}$ and $R^{4d}$ at each instance are independently selected from the group consisting of hydrogen; $C_1$-$C_6$ perfluoroalkyl; cyano; nitro; and halo;
  $R^5$ and $R^6$ at each instance are independently selected from the group consisting of optionally substituted $C_1$-$C_6$ alkyl; and $C_1$-$C_6$ alkylsulfonyl; alternatively $R^5$ and $R^6$ taken together with the nitrogen to which they are attached form an optionally substituted $C_3$-$C_6$ heterocyclyl; and $R^7$ is an optionally substituted $C_3$-$C_6$ heterocyclyl;
  with the following proviso: when $R^2$ is hydrogen, $R^{1a}$ is optionally substituted $C_{1-6}$ alkyl.

2. The compound of claim 1, according to formula (II):

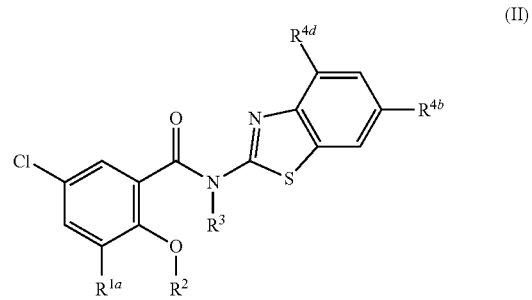

(II)

or a pharmaceutically acceptable salt, solvate, or prodrug thereof.

3. The compound of claim 1, wherein $R^{1a}$ is selected from the group consisting of hydrogen; $C_1$-$C_6$ alkyl; $C_3$-$C_6$ cycloalkyl, (N,N-dimethylamino)$C_1$-$C_6$ alkyl; and ((C$_1$-$C_6$ alkylsulfonyl)amino)$C_1$-$C_6$alkyl.

4. The compound of claim 1, wherein:
  $R^2$ is selected from; C(O)NR$^5$R$^6$; and C(O)R$^7$;
  alternatively, $R^2$ and $R^3$ taken together are a carbonyl group and together with the atoms to which they are attached, form a six-membered heterocyclic carbamate,
  $R^5$ and $R^6$ taken together with the nitrogen to which they are attached form an optionally substituted $C_3$-$C_6$ heterocyclyl; and
  $R^7$ is 2-pyrrolidine.

5. The compound of claim 1, wherein $R^{4b}$ and $R^{4d}$ at each instance are independently selected from the group consisting of: hydrogen; trifluoromethyl; cyano; nitro; and fluoro.

6. A compound selected from the group consisting of

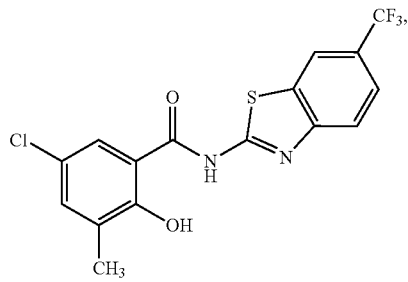

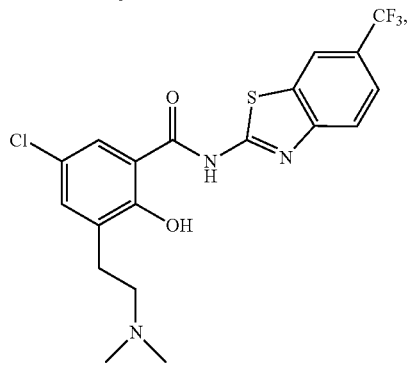

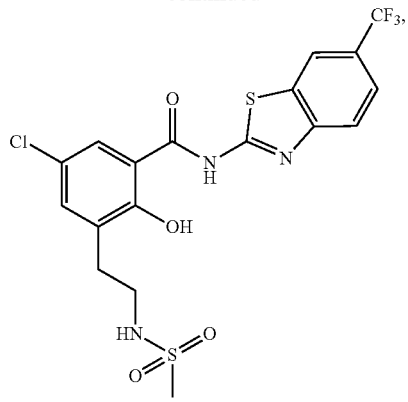
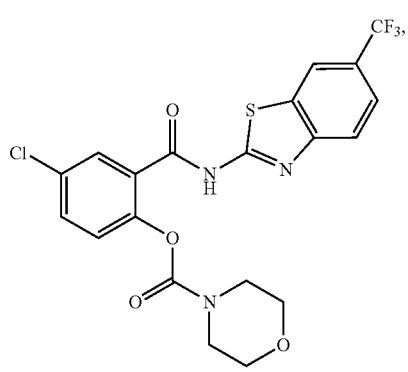
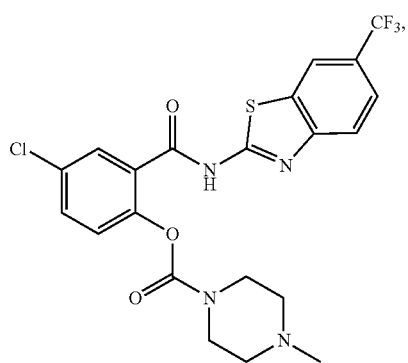
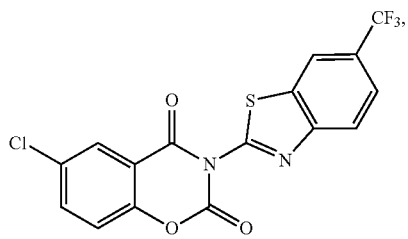
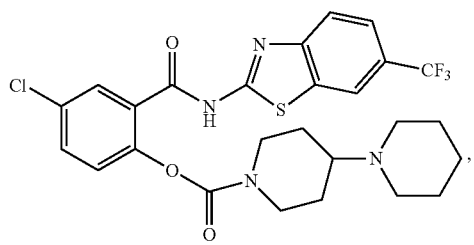
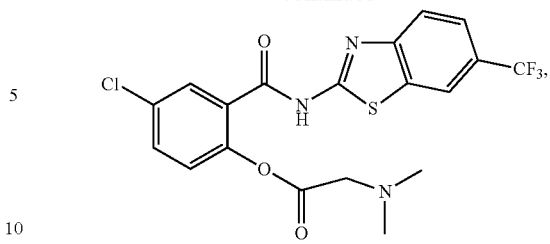
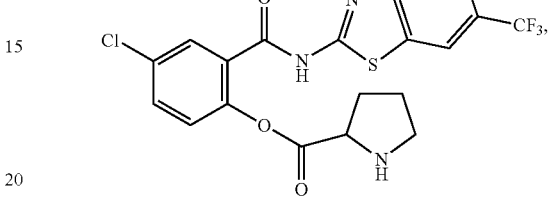
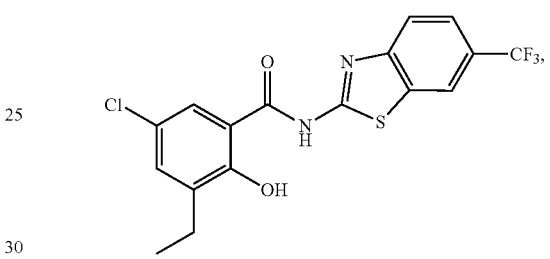
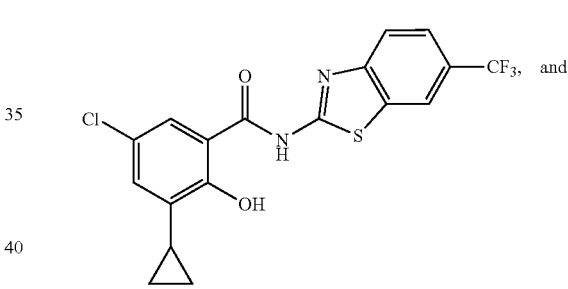
or a pharmaceutically acceptable salt, solvate, or prodrug thereof.
7. A compound selected from the group consisting of -continued

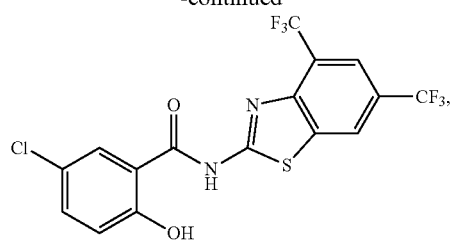

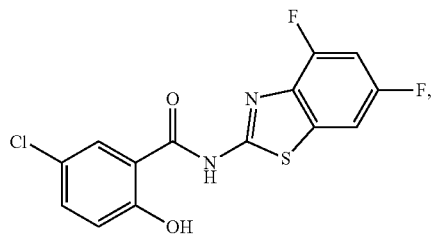

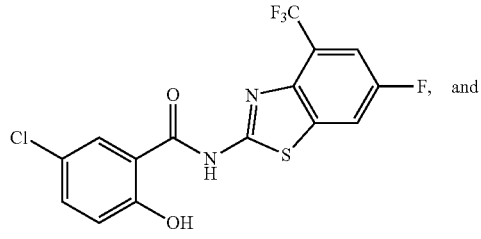

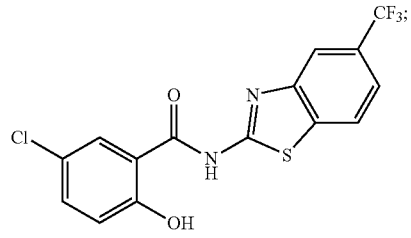

or a pharmaceutically acceptable salt, solvate, or prodrug thereof.

8. A pharmaceutical composition comprising a compound according to claim 1, or a pharmaceutically acceptable salt or prodrug thereof and a pharmaceutically acceptable carrier or diluent.

9. A pharmaceutical composition comprising a compound according to claim 2, or a pharmaceutically acceptable salt or prodrug thereof and a pharmaceutically acceptable carrier or diluent.

10. A pharmaceutical composition comprising a compound according to claim 7, or a pharmaceutically acceptable salt or prodrug thereof and a pharmaceutically acceptable carrier or diluent.

11. A compound selected from the group consisting of

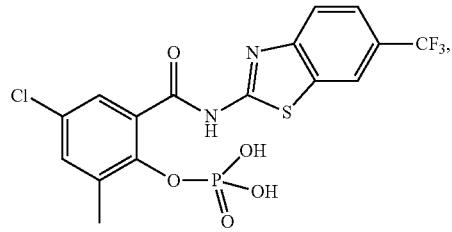

-continued

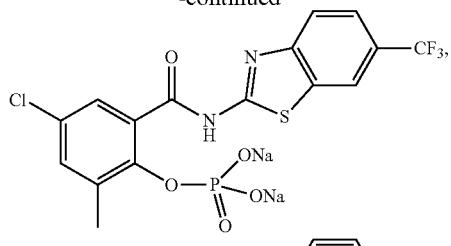

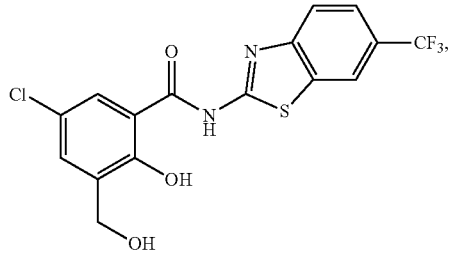

or a pharmaceutically acceptable salt, solvate, or prodrug thereof.

12. A compound selected from the group consisting of,

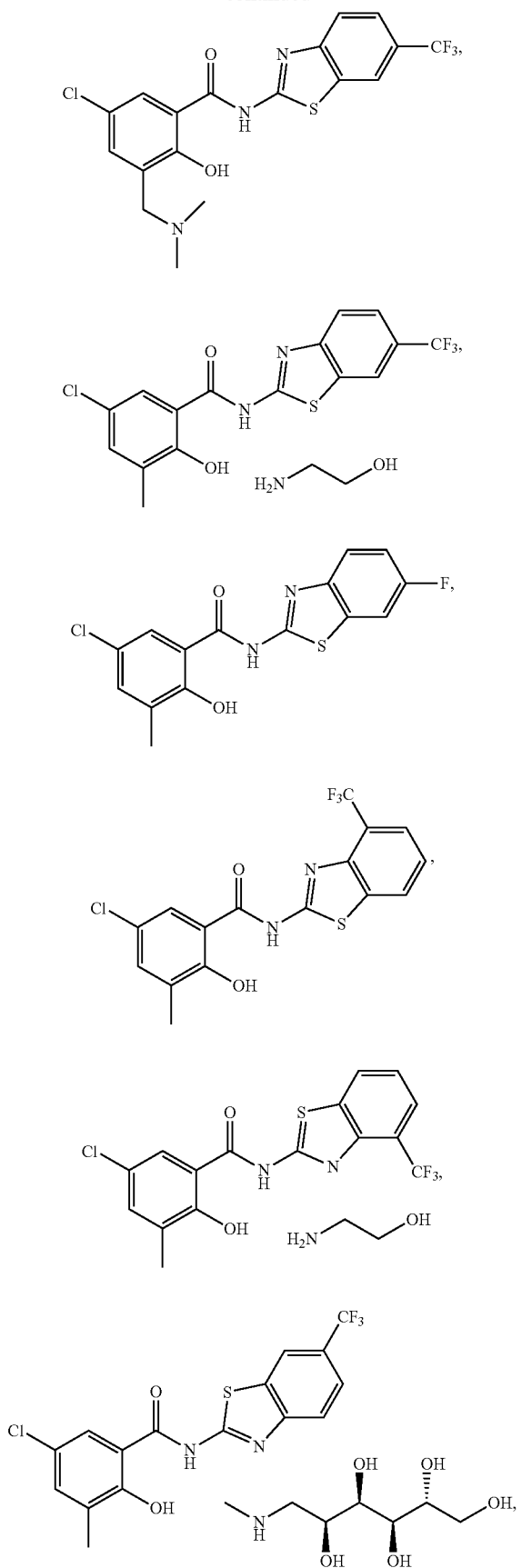
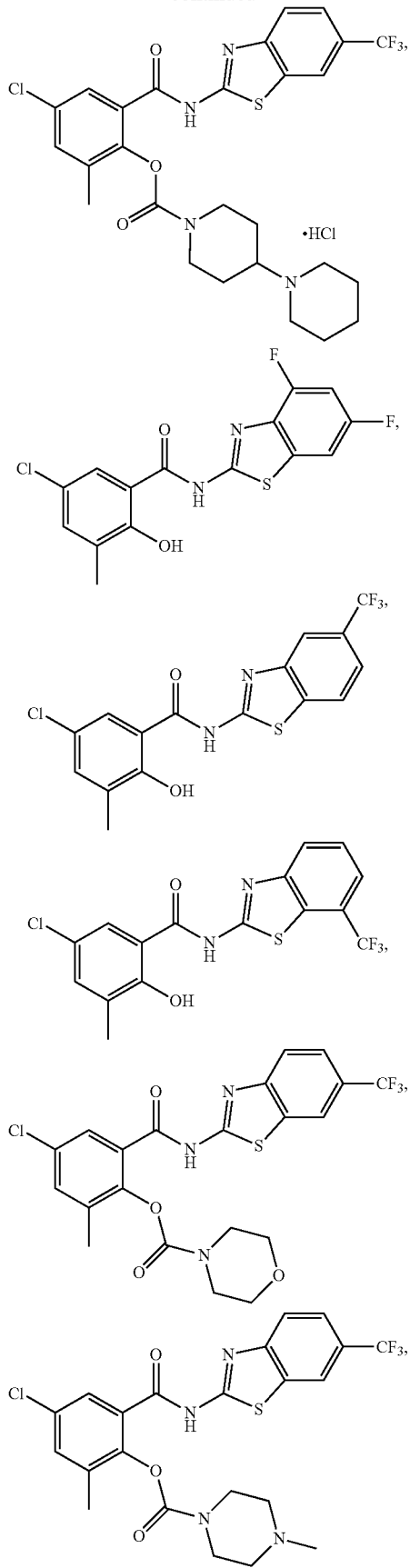

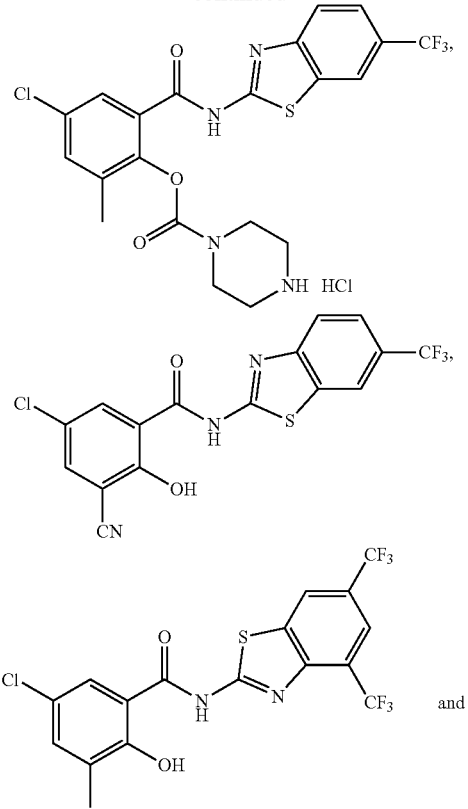

or a pharmaceutically acceptable salt, solvate, or prodrug thereof.

13. A pharmaceutical composition comprising a compound according to claim 11, or a pharmaceutically acceptable salt or prodrug thereof and a pharmaceutically acceptable carrier or diluent.

14. A pharmaceutical composition comprising a compound according to claim 12, or a pharmaceutically acceptable salt or prodrug thereof and a pharmaceutically acceptable carrier or diluent.

15. A pharmaceutical composition comprising a compound according to claim 7, or a pharmaceutically acceptable salt or prodrug thereof and a pharmaceutically acceptable carrier or diluent.

* * * * *